United States Patent [19]

Tamura et al.

[11] Patent Number: 5,310,874
[45] Date of Patent: May 10, 1994

[54] INTEGRIN ALPHA SUBUNIT CYTOPLASMIC DOMAIN POLYPEPTIDES AND ANTIBODIES

[75] Inventors: Richard N. Tamura, San Diego; Vito Quaranta, La Jolla, both of Calif.

[73] Assignee: The Scripps Research Institute, La Jolla, Calif.

[21] Appl. No.: 695,564

[22] Filed: May 3, 1991

[51] Int. Cl.$^5$ .......................... C07K 7/00; C07K 15/28
[52] U.S. Cl. .................................... 530/324; 530/325; 530/326; 530/388.2; 530/387.9; 436/536
[58] Field of Search ................................ 530/324–326, 530/350, 388.2, 387.9; 514/13

[56] References Cited

PUBLICATIONS

Hemler et al. "Association of the VLA $\alpha^6$ Subunit with a Novel Protein" J. Biol. Chemistry 264(11) 6529–6535, Apr. 1989.

*Primary Examiner*—Robert J. Hill, Jr.
*Assistant Examiner*—L. Spector
*Attorney, Agent, or Firm*—Douglas A. Bingham; Thomas Fitting; April C. Logan

[57] ABSTRACT

Diagnostic systems, methods, polypeptides and antibodies for detecting the presence of the cytoplasmic domain of the integrin $\alpha_{6B}$ or $\alpha_{3B}$ subunit in a body sample are disclosed

11 Claims, 9 Drawing Sheets

```
2924 TAACTGTAGCGTGAACGTGAACTGTGTGAACATCAGATGCCCGCTGCGGGGGCTGGACAG 2983
     ||||||||||||||||||||||||||||||||||||||||||||||||||||||||||||
   1 TAACTGTAGCGTGAACGTGAACTGTGTGAACATCAGATGCCCGCTGCGGGGGCTGGACAG   60

2984 CAAGGCGTCTCTTATTTTGCGCTCGAGGTTATGGAACAGCACATTTCTAGAGGAATATTC 3043
     ||||||||||||||||||||||||||||||||||||||||||||||||||||||||||||
  61 CAAGGCGTCTCTTATTTTGCGCTCGAGGTTATGGAACAGCACATTTCTAGAGGAATATTC  120

3044 CAAACTGAACTACTTGGACATTCTCATGCGAGCCTTCATTGATGTGACTGCTGCTGCCGA 3103
     ||||||||||||||||||||||||||||||||||||||||||||||||||||||||||||
 121 CAAACTGAACTACTTGGACATTCTCATGCGAGCCTTCATTGATGTGACTGCTGCTGCCGA  180

3104 AAATATCAGGCTGCCAAATGCAGGCACTCAGGTTCGAGTGACTGTGTTTCCCTCAAAGAC 3163
     ||||||||||||||||||||||||||||||||||||||||||||||||||||||||||||
 181 AAATATCAGGCTGCCAAATGCAGGCACTCAGGTTCGAGTGACTGTGTTTCCCTCAAAGAC  240

3164 TGTAGCTCAGTATTCGGGAGTACCTTGGTGGATCATCCTAGTGGCTATTCTCGCTGGGAT 3223
     ||||||||||||||||||||||||||||||||||||||||||||||||||||||||||||
 241 TGTAGCTCAGTATTCGGGAGTACCTTGGTGGATCATCCTAGTGGCTATTCTCGCTGGGAT  300

3224 CTTGATGCTTGCTTTATTAGTGTTTATACTATGGAAGTGTGGTTTCTTCAAGAGAAATAA 3283
     |||||||||||||||||||||||||||||||||||||
 301 CTTGATGCTTGCTTTATTAGTGTTTATACTATGGAAG........................  360

3284 GAAAGATCATTATGATGCCACATATCACAAGGCTGAGATCCATGCTCAGCCATCTGATAA 3343
 361 ............................................................  420

3344 AGAGAGGCTTACTTCTGATGCATAGTATTGATCTACTTCTGTAATTGTGTGGATTCTTTA 3403
                                                  ||||||||||||
 421 .........................................TGTGGATTCTTTA       480

3404 AACGCTCTAGGTACGATGACAGTGTTCCCCGATACCATGCTGTAAGGATCCG          3455
     ||||||||||||||||||||||||||||||||||||||||||||||||||||
 481 AACGCTCTAGGTACGATGACAGTGTTCCCCGATACCATGCTGTAAGGATCCG           532
```

FIG.5

```
                                1157                   1681
                     ─────────────────────▶  ─ ─ ─ ─ ─ ─ ─ ─▶
2901 GCTGAAAGAAAATACCAGACTCTTAACTGTAGCGTGAACGTGAACTGTGTGAACATCAGA 2960
      A  E  R  K  Y  Q  T  L  N  C  S  V  N  V  N  C  V  N  I  R

2961 TGCCCGCTGCGGGGGCTGGACAGCAAGGCGTCTCTTATTTTGCGCTCGAGGTTATGGAAC 3020
      C  P  L  R  G  L  D  S  K  A  S  L  I  L  R  S  R  L  W  N

3021 AGCACATTTCTAGAGGAATATTCCAAACTGAACTACTTGGACATTCTCATGCGAGCCTTC 3080
      S  T  F  L  E  E  Y  S  K  L  N  Y  L  D  I  L  M  R  A  F

3081 ATTGATGTGACTGCTGCTGCCGAAAATATCAGGCTGCCAAATGCAGGCACTCAGGTTCGA 3140
      I  D  V  T  A  A  A  E  N  I  R  L  P  N  A  G  T  Q  V  R

3141 GTGACTGTGTTTCCCTCAAAGACTGTAGCTCAGTATTCGGGAGTACCTTGGTGGATCATC 3200
      V  T  V  F  P  S  K  T  V  A  Q  Y  S  G  V  P  W  W  I  I

3201 CTAGTGGCTATTCTCGCTGGGATCTTGATGCTTGCTTTATTAGTGTTTATACTATGGAAG 3260
      L  V  A  I  L  A  G  I  L  M  L  A  L  L  V  F  I  L  W  K

3261 TGTGGTTTCTTCAAGAGAAATAAGAAAGATCATTATGATGCCACATATCACAAGGCTGAG 3320
      C  G  F  F  K  R  N  K  K  D  H  Y  D  A  T  Y  H  K  A  E

3321 ATCCATGCTCAGCCATCTGATAAAGAGAGGCTTACTTCTGATGCATAGTATTGATCTACT 3380
      I  H  A  Q  P  S  D  K  E  R  L  T  S  D  A  *
                                                        ◀─── 2002
3381 TCTGTAATTGTGTGGATTCTTTAAACGCTCTAGGTACGATGACAGTGTTCCCCGATACCA 3440
      C  G  F  F  K  R  S  R  Y  D  D  S  V  P  R  Y  H
                         1156
3441 TGCTGTAAGGATCCGGAAAGAAGAGCGAGAGATCAAAGATGAAAAGTATATTGATAACCT 3500
      A  V  R  I  R  K  E  E  R  E  I  K  D  E  K  Y  I  D  N  L

3501 TGAAAAAAAACAGTGGATCACAAAGTGGAACAGAAATGAAAGCTACTCATAGCGGGGGCC 3560
      E  K  K  Q  W  I  T  K  W  N  R  N  E  S  Y  S  *

3561 TAAAAAAAAAAAAGCTTCACAGTACCCAAACTGCTTTTTC 3600
```

FIG.6

```
                1157
           ─────────▶
         gactcttaactgtagcgtgaacgtgaggtgtgtgaacatcaggtgcccactgcgagggct    2976
         gactcttaactgtagcgtgaacgtgaggtgtgtgaacatcaggtgcccactgcgagggct
          T  L  N  C  S  V  N  V  R  C  V  N  I  R  C  P  L  R  G  L ggacagcaaggcctctctcgttcttcgttccaggttgtggaacagcacatttctagagga    3036
         ggacagcaaggcctctctcgttcttcgttccaggttgtggaacagcacatttctagagga
          D  S  K  A  S  L  V  L  R  S  R  L  W  N  S  T  F  L  E  E atattccaaactgaactacttggacattctcctgagggcttccatagatgtcaccgctgc    3096
         atattccaaactgaactacttggacattctcctgagggcttccatagatgtcaccgctgc
          Y  S  K  L  N  Y  L  D  I  L  L  R  A  S  I  D  V  T  A  A tgctcagaatatcaagctcctcaccgccggcactcaggttcgagtgacggtgtttccctc    3156
         tgctcagaatatcaagctcctcaccgccggcactcaggttcgagtgacggtgtttccctc
          A  Q  N  I  K  L  L  T  A  G  T  Q  V  R  V  T  V  F  P  S aaagactgtagctcagtattcaggagtagcttggtggatcatcctcctggctgttcttgc    3216
         aaagactgtagctcagtattcaggagtagcttggtggatcatcctcctggctgttcttgc
          K  T  V  A  Q  Y  S  G  V  A  W  W  I  I  L  L  A  V  L  A cgggattctgatgctggctctattagtgttttttactgtggaa................    3276
         cgggattctgatgctggctctattagtgttttttactgtggaagtgtggcttcttcaagag
          G  I  L  M  L  A  L  L  V  F  L  L  W  K ┌C  G  F  F  K  R┐

................................................          3336
         aaataagaaagatcattacgatgccacctatcacaaggctgagatccatactcagccgtc
          N  K  K  D  H  Y  D  A  T  Y  H  K  A  E  I  H  T  Q  P  S ............................................gtgtggat      3396
         tgataaagagaggcttacttccgatgcatagtattgatctacttccataattgtgtggat
          D  K  E  R  L  T  S  D  A  *                  ┌C  G  F
                                                        ◀───── tctttaagcgctctaggtacgatgacagcattccccgataccatgcggtgcggatccgga    3456
         tctttaagcgctctaggtacgatgacagcattccccgataccatgcggtgcggatccgga
         ┌F  K  R┐  S  R  Y  D  D  S  I  P  R  Y  H  A  V  R  I  R  K
          ─────── 1156
         aagaagagcgagagat   3516
         aagaagagcgagagat                    FIG.8
          E  E  R  E
```

INTEGRIN ALPHA SUBUNIT CYTOPLASMIC DOMAIN POLYPEPTIDES AND ANTIBODIES

TECHNICAL FIELD

The present invention relates to polypeptides that define the integrin $\alpha_6$ and $\alpha_3$ subunits, particularly the cytoplasmic domain of the $\alpha_6$ and $\alpha_3$ subunits. In addition, the invention describes antibodies immunoreactive with the cytoplasmic domain of $\alpha_6$ and $\alpha_3$, and methods for using the antibodies and polypeptides in assays for detecting $\alpha_6$ and $\alpha_3$ subunits in body samples.

BACKGROUND

The integrin family of cell surface receptors serve cellular adhesion functions. The receptors form a link between the extracellular matrix and the cytoskeleton through their binding to various extracellular components. Each integrin receptor is a heterodimer comprised of an $\alpha$ and a $\beta$ subunit. At least 11 $\alpha$ chains (Ruoslahti and Giancotti, 1989) and six $\beta$ chains (Sheppard et al., 1990) have been recognized in man. Each $\alpha$ subunit tends to associate with only one type of $\beta$ subunit, but there are several exceptions to this rule (Hemler et al., 1989; Cheresh et al., 1989; Holzmann et al., 1989; Freed et al., 1989).

The human heterodimer VLA-6 was identified using the monoclonal antibody GoH3, which is immunoreactive with the $\alpha_6$ subunit expressed on the surface of mouse and human cells. Hemler et al. *J. Biol. Chem.*, 263:7660-7665, (1988); and Sonnenberg et al. *J. Biol. Chem.*, 262:10376-10383, (1987). The amino terminal sequence of the human VLA-6 $\alpha_6$ subunit was determined from purified protein (Kajiji et al. *EMBO J.* 8:673-680,1989) and was used to design degenerate oligonucleotides for probing a cDNA library. The full length sequence of $\alpha_6$ cDNA, and its predicted amino acid sequence, were elucidated subsequent to cDNA cloning. Tamura, et al., *J. Cell Biol.*, 111:1593-1604 (1990). While Tamura et al., supra, also disclose multiple cDNA sequences encoding the VLA-6 $\beta_4$ subunit, there is provided no evidence that additional VLA-6 $\alpha_6$ subunits exist. European Patent Application Publication Number 279,669 (published Jul. 24, 1988) describes human $\alpha_6$ and $\beta_4$ subunits of an integrin receptor and the complex they associate to form on pancreatic and other cancer cells. The publication does not describe or suggest that an isoform of the $\alpha_6$ subunit exits.

The full length sequence of a hamster cDNA encoding the Gap b3 cell surface membrane glycoprotein was described by Tsuji et al., *J. Biol. Chem.*, 265:7016-7021 (1990). Based on the predicted amino acid sequence and predicted overall structure, it was suggested that Gap b3 is the hamster homolog of the $\alpha_3$ integrin subunit. The sequence of a cDNA encoding the partial sequence of chicken $\alpha_3$ protein was disclosed in Hynes et al. *J. Cell Biol.*, 109:409-420 (1989). The cytoplasmic regions of these clones do not share homology with the cytoplasmic region of $\alpha_{3B}$ disclosed herein, and are therefore assumed to encode $\alpha_{3A}$ subunit isoform. Furthermore, neither publication suggest the possibility of an $\alpha_{3B}$ subunit.

The N-terminal amino acid sequence of human $\alpha_3$ protein is provided in European Patent Application Publication Number 330,506 (published Jul. 3, 1989). That publication provides no suggestion that an isoform of the $\alpha_3$ protein, namely $\alpha_{3B}$, exists.

BRIEF SUMMARY OF THE INVENTION

A new species of alpha ($\alpha$) integrin subunit protein has been discovered, with representative members in both the $\alpha_6$ and $\alpha_3$ class of integrins corresponding to the laminin receptor and the laminin, collagen and fibronectin receptors, respectively. Specifically, it has been discovered that new $\alpha_6$ species and $\alpha_3$ species exist which differ from previously described $\alpha_6$ and $\alpha_3$ proteins in the cytoplasmic domain of the protein. Through a combination of cDNA sequencing studies and anti-synthetic peptide antibody immunoreactivity studies, it has been shown that the cytoplasmic domain of these new proteins, designated $\alpha_{6B}$ and $\alpha_{3B}$, are related between human and mouse isolates.

Thus the present invention describes polypeptides comprising an amino acid residue sequence that includes the amino acid residue sequence defining an antigenic determinant in the cytoplasmic domain of the human or mouse $\alpha_{6B}$ or $\alpha_{3B}$ protein. Preferably the polypeptide has a sequence corresponding to the whole cytoplasmic domain of either the human or mouse $\alpha_{6B}$ or $\alpha_{3B}$ protein. Alternatively, a polypeptide can correspond to all or substantially all of a native human or mouse $\alpha_{6B}$ or $\alpha_{3B}$ subunit in substantially isolated form.

The polypeptides or proteins are useful as immunogens for preparing polyclonal and monoclonal antibodies immunoreactive with the human or mouse $\alpha_{6B}$ or $\alpha_{3B}$ cytoplasmic domains, and as reagents for use in diagnostic assays for detecting the $\alpha_{6B}$ or $\alpha_{3B}$ proteins.

Thus, in a related embodiment the invention describes polyclonal and monoclonal antibodies having imunospecificities for antigenic determinants on the cytoplasmic domains of $\alpha_{6B}$ and $\alpha_{3B}$ proteins. These antibodies find use in in vitro and in situ immunoassays for detecting $\alpha_{6B}$ or $\alpha_{3B}$ cytoplasmic domain antigens in body samples such as tissues or fluids.

Another aspect of the invention is the diagnostic methods and kits therefor, for detecting $\alpha_{6B}$ or $\alpha_{3B}$ cytoplasmic domain antigenic determinants using an antibody of this invention.

Other features and benefits of the invention will become apparent from the following detailed description and specific examples describing the invention, its principles and preferred embodiments.

BRIEF DESCRIPTION OF THE DRAWINGS

In the drawings forming a portion of this disclosure:

FIG. 2 shows immunodepletion with NRS or with anit-$\alpha_6$ Mab, and FIG. 3 shows immunodepletion with anti-$\alpha_{6A}$ or with anti-$\alpha_{6B}$.

FIG. 5 compares the nucleotide sequences of the 540 bp and 410 bp amplification products described in FIG. 4. The 540 bp product shown on the top line is designated $\alpha_{6A}$, and the 410 bp product shown on the bottom line is designated $\alpha_{6B}$. Vertical bars denote where the two sequences are homologous. Horizontal dots denote a 130 nucleotide (nt) deletion in the $\alpha_{6B}$ sequence with respect to the $\alpha_{6A}$ sequence. The 130 nt deletion is in the region that encodes the $\alpha_{6A}$ cytoplasmic domain.

FIG. 6 provides and compares the predicted amino acid sequence for the $\alpha_6$ amplification products shown in FIG. 5. The solid arrows show the location of the outer PCR primers; the broken arrows show the location of the nested inner PCR primers. The underlined sequence represent the putative transmembrane domain. The open boxed area is the $\alpha_{6A}$ cytoplasmic domain; the shaded boxed area is the $\alpha_{6B}$ cytoplasmic domain. The bracketed area represents the 130 nt sequence deleted from the $\alpha_{6B}$ sequence.

FIG. 8 provides and compares the nucleotide and predicted amino acid sequences for the mouse $\alpha_6$ amplification products shown in FIG. 7. The $\alpha_{6B}$ sequence is on the top line; the $\alpha_{6A}$ sequence is on the bottom line. Predicted amino acid residues are noted below the nucleotide sequence. The solid arrows show the location of the PCR primers. The boxed regions encompass the start of cytoplasmic domain for the $\alpha_{6A}$ and $\alpha_{6B}$ proteins, respectively.

DETAILED DESCRIPTION OF THE INVENTION

A. Definitions

Figure 1A:
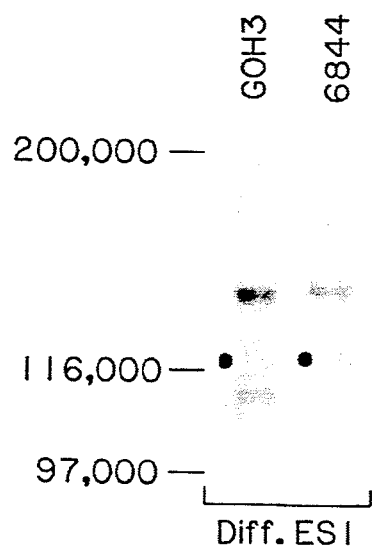
FIGS. 1A and 1B illustrates immunoprecipitation of polypeptides from mouse cells using antibodies specific for the $\alpha_6$ subunit. The differentiated (Diff.) ES1 and D3 cells are described in Example 2. Antibody GoH3 is a monoclonal antibody immunospecific for the extracellular domain of the $\alpha_{6A}$ subunit. Antisera 6844 was raised in rabbit against a synthetic peptide specific for the cytoplasmic domain of human $\alpha_{6A}$. The immunoprecipitated labeled proteins were visualized by SDS-PAGE. Molecular weight, in kilodaltons, is noted on the side of the gel.

Amino Acid Residue: An amino acid formed upon chemical digestion (hydrolysis) of a polypeptide at its peptide linkages. The amino acid residues described herein are preferred to be in the "L" isomeric form. However, residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature described in *J. Biol. Chem.*, 243:3552-59 (1969) and adopted at 37 C.F.R. 1.822(b) (2)), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus. In addition, the phrase "amino acid residue" is broadly defined to include the amino acids listed in the Table of Correspondence and modified and unusual amino acids, such as those listed in 37 C.F.R. 1.822(b)(4), and incorporated herein by reference. Furthermore, it should be noted that a dash at the beginning or end of an amino acid residue sequence indicates either a peptide bond to a further sequence of one or more amino acid residues or a covalent bond to a carboxyl or hydroxyl end group.

Polypeptide and Peptide: Polypeptide and peptide are terms used interchangeably herein to designate a linear series of amino acid residues connected one to the other by peptide bonds between the alpha-amino and carboxy groups of adjacent residues.

Protein: Protein is a term used herein to designate a linear series of greater than about 50 amino acid residues connected one to the other as in a polypeptide.

Synthetic peptide: refers to a chemically produced chain of amino acid residues linked together by peptide bonds that is free of naturally occurring proteins and fragments thereof.

Nucleotide: A monomeric unit of DNA or RNA consisting of a sugar moiety (pentose), a phosphate, and a nitrogenous heterocyclic base. The base is linked to the sugar moiety via the glycosidic carbon (1' of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus.

Base Pair (bp): A partnership of adenine (A) with thymine (T), or of cytosine (C) with guanine (G) in a double stranded DNA molecule. In RNA, uracil (U) is substituted for thymine.

Nucleic Acid: A polymer of nucleotides, either single or double stranded.

Polynucleotide: a polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, probes, RNA/DNA segments, oligonucleotides or "oligos" (relatively short polynucleotides), genes, vectors, plasmids, and the like.

Gene: A nucleic acid whose nucleotide sequence codes for an RNA or polypeptide. A gene can be either RNA or DNA.

Duplex DNA: a double-stranded nucleic acid molecule comprising two strands of substantially complementary polynucleotides held together by one or more hydrogen bonds between each of the complementary bases present in a base pair of the duplex. Because the nucleotides that form a base pair can be either a ribonucleotide base or a deoxyribonucleotide base, the phrase "duplex DNA" refers to either a DNA-DNA duplex comprising two DNA strands (ds DNA), or an RNA-DNA duplex comprising one DNA and one RNA strand.

Recombinant DNA (rDNA) molecule: a DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

Vector: a rDNA molecule capable of autonomous replication in a cell and to which a DNA segment, e.g., gene or polynucleotide, can be operatively linked so as to bring about replication of the attached segment. Vectors capable of directing the expression of genes encoding for one or more proteins are referred to herein as "expression vectors". Particularly important vectors allow cloning of cDNA (complementary DNA) from mRNAs produced using reverse transcriptase.

B. Integrin Alpha Subunit Polypeptides

The present invention relates to a previously undescribed species of integrin alpha subunit that is derived by splicing of the messenger RNA in the tissue in which the integrin alpha subunit is expressed, such that the amino acid sequence of the alpha subunit polypeptide has a sequence as defined herein.

Splicing as a form of regulation of gene expression is one means by which a cell regulates the structural gene products expressed in that cell type. According to the structures defined herein, it is now known that the $\alpha_6$ and $\alpha_3$ integrin subunits can each be expressed in two alternate forms (isoforms), designated herein as an "A" form and a "B" form depending upon the spliced product, and are referred to as $\alpha_{6A}$ or $\alpha_{6B}$, and as $\alpha_{3B}$ or $\alpha_{3B}$.

The newly described $\alpha_{6B}$ and $\alpha_{3B}$ subunits contain a carboxyterminal amino acid residue sequence defining their cytoplasmic domain that is different from their $\alpha_{6A}$ and $\alpha_{3A}$ counterparts. These new species of $\alpha_{6B}$ and $\alpha_{3B}$ provide, based on their sequence differences, novel polypeptide reagents based on (1) the antigenic determinants present in their cytoplasmic domains and (2) the structural role the cytoplasmic domain of these proteins play in the function of the integrins of which they are members.

1. $\alpha_{6B}$ Subunit Polypeptides

In one embodiment, the present invention contemplates a polypeptide based on the cytoplasmic domain of the $\alpha_{6B}$ species of the integrin $\alpha_6$ subunit. This polypeptide has an amino acid sequence that includes a sequence that corresponds, and preferably is identical to, the amino acid residue sequence of the cytoplasmic domain of the human or mouse $\alpha_{6B}$.

The cytoplasmic domain of human $\alpha_{6B}$ includes an amino acid residue sequence shown in SEQ ID NO 3 from residue 1068 to residue 1091 and of mouse $\alpha_{6B}$ has an amino acid residue sequence shown in SEQ ID NO 5 from residue 121 to residue 141.

Thus, in one embodiment, the present invention contemplates a polypeptide having an amino acid residue sequence that includes at least the sequence shown in SEQ ID NO 3 from residue 1068 to residue 1091 that defines the carboxy terminal portion of cytoplasmic domain of human $\alpha_{6B}$. Preferably a polypeptide has an amino acid residue sequence shown in SEQ ID NO 3 from residue 1068 to residue 1091, and more preferably has an amino acid residue sequence shown in SEQ ID NO 3 from residue 1045 to residue 1091. In a related embodiment the invention contemplates the whole human $\alpha_{6B}$ protein, in a substantially isolated form, having a sequence shown in SEQ ID NO 3 from residue 1 to residue 1091.

By substantially isolated is meant that the protein is present in a composition as a major constituent, typically in amount greater than 10%, and preferably greater than 90%, of the total protein in the composition. Human $\alpha_{6B}$ protein can be isolated by a variety of biochemical and immunological means from the tissue sources and cells described herein that contain $\alpha_{6B}$ subunit. Exemplary methods involve the use of a $\alpha_{6B}$ cytoplasmic domain specific antibody, such as 382 described herein, alone or in combination with the teachings of Kajiji et al., EMBO J., 8:673-680 (1989).

In a related embodiment, the present invention contemplates a polypeptide having an amino acid residue sequence that includes at least the sequence shown in SEQ ID NO 5 from residue 121 to residue 141 that defines a portion of the cytoplasmic domain of mouse $\alpha_{6B}$. Preferably a polypeptide has an amino acid residue sequence shown in SEQ ID NO 5 from residue 121 to residue 141. Also contemplated is the whole mouse $\alpha_{6B}$ protein in a substantially isolated form that included a sequence shown in SEQ ID NO 5 from residue 1 to residue 141, with the degree of isolation being the same as above for human $\alpha_{6B}$. Purification of mouse $\alpha_{6B}$ can similarly be accomplished using the methods described above, and particularly using the murine cells described herein as a source of protein and an anti-peptide antibody prepared using mouse $\alpha_{6B}$ cytoplasmic domain-derived polypeptides.

The native mouse $\alpha_{6B}$ subunit polypeptide is a protein of about 125,000 daltons in molecular weight when analysed by PAFE-SDS under reducing conditons as described in the Examples.

The native human $\alpha_{6B}$ subunit polypeptide is a protein of about 125,000 daltons in molecular weight when analysed by polyacrylamide-sodium dodecyl sulfate gel electrophoresis (PAGE-SDS) under reducing conditions as described in the Examples.

2. $\alpha_{3B}$ Subunit Polypeptides

In another embodiment, the present invention contemplates a polypeptide based on the cytoplasmic domain of the $\alpha_{3B}$ species of the integrin $\alpha_{3B}$ subunit. This polypeptide has an amino acid sequence that includes a sequence that corresponds, and preferably is identical to, the amino acid residue sequence of the cytoplasmic domain of the human or mouse $\alpha_{3B}$.

The cytoplasmic domain of mouse $\alpha_{3B}$ has an amino acid residue sequence shown in SEQ ID NO 9 from residue 113 to residue 153.

Thus, in one embodiment, the present invention contemplates a polypeptide having an amino acid residue sequence that includes at least the sequence shown in SEQ ID NO 9 from residue 113 to residue 153 that defines a portion of the cytoplasmic domain of $\alpha_{3B}$. Preferably a polypeptide has an amino acid residue sequence shown in SEQ ID NO 9 from residue 113 to residue 153, and more preferably has an amino acid residue sequence shown in SEQ ID NO 9 from residue 1 to residue 153.

In a related embodiment, the invention contemplates the whole mouse $\alpha_{3B}$ protein, in a substantially isolated form having a sequence that includes the sequence shown in SEQ ID NO 9 from residue 1 to residue 153. The degree of isolation for mouse $\alpha_{3B}$ is the same as is for human $\alpha_{6B}$ above, with methods for preparing the mouse $\alpha_{3B}$ similarly based on immunoprecipitation or immunoaffinity isolation methods using an antibody specific for mouse $\alpha_{3B}$ cytoplasmic domain as defined herein.

In preferred embodiments, a polypeptide of the present invention comprises about 20 to 1100 amino acid residues, and preferably comprises about 24 to 50 amino acid residues.

Preferably, a polypeptide of this invention is further characterized by its ability to immunologically mimic an epitope (antigenic determinant) expressed by the cytoplasmic domain of $\alpha_{6B}$ or $\alpha_{3B}$ as defined herein.

As used herein, the phrase "immunologically mimic" in its various grammatical forms refers to the ability of a polypeptide of this invention to immunoreact with an antibody of the present invention that recognizes an epitope on the cytoplasmic domain of $\alpha_{6B}$ or $\alpha_{3B}$ as defined herein.

It should be understood that a subject polypeptide need not be identical to the amino acid residue sequence of $\alpha_{6B}$ or $\alpha_{3B}$ so long as it includes a sequence that provides at least one epitope within the cytoplasmic domain of the $\alpha_{6B}$ or $\alpha_{3B}$ subunit and is able to immunoreact with antibodies of the present invention.

A subject polypeptide includes any analog, fragment or chemical derivative of a polypeptide whose amino acid residue sequence is shown h rein so long as the polypeptide is capable of immunologically mimicking a native epitope present in the cytoplasmic domain of $\alpha_{6B}$ or $\alpha_{3B}$. Therefore, a polypeptide can be subject to various changes, substitutions, insertions, and deletions where such changes provide for certain advantages in its use. The term "analog" includes any polypeptide having an amino acid residue sequence substantially identical to a sequence specifically shown herein in which one or more residues have been conservatively substituted with a functionally similar residue and which displays the ability to mimic the cytoplasmic domain of $\alpha_{6B}$ or $\alpha_{3B}$ as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form 0-acyl or 0-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

When a polypeptide of the present invention has a sequence that is not identical to the sequence of the cytoplasmic domain of $\alpha_{6B}$ or $\alpha_{3B}$ because one or more conservative or non-conservative substitutions have been made, usually no more than about 30 number percent, more usually no more than 20 number percent, and preferably no more than 10 number percent of the amino acid residues are substituted, except that additional residues can be added at either terminus for the purpose of providing a "linker" by which the polypeptides of this invention can be conveniently affixed to a label or solid matrix, or carrier, such that the linker residues do not form epitopes expressed by the cytoplasmic domain of $\alpha_{6B}$ or $\alpha_{3B}$ as defined herein. Labels, solid matrices and carriers that can be used with the polypeptides of this invention are described hereinbelow.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a subject polypeptide can differ, unless otherwise specified, from the natural sequence of an $\alpha_{6B}$ or $\alpha_{3B}$ cytoplasmic domain by the sequence being modified by terminal-$NH_2$ acylation, e.g., acetylation, or thioglycolic acid amidation, by terminal-carboxlyamidation, e.g., with ammonia, methylamine, and the like.

When coupled to a carrier to form what is known in the art as a carrier-hapten conjugate, a polypeptide of the present invention is capable of inducing antibodies that immunoreact with the cytoplasmic domain of either human or mouse α6B or mouse $α_{3B}$. Where the immunogen is an $α_{3B}$-derived polypeptide, the induced antibodies immunoreact with the cytopolasmic domain of either human or mouse $α_{3B}$. This cross-reactivity between human and mouse cytoplasmic domains is shown by the disclosures herein. In view of the well established principle of immunologic cross-reactivity, the present invention therefore contemplates antigenically related variants of the polypeptides of this invention. An "antigenically related variant" is a subject polypeptide that is capable of inducing antibody molecules that immunoreact with a subject polypeptide and with $α_{6B}$ or $α_{3B}$.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

A polypeptide of the present invention, also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W. H. Freeman Co., San Francisco, 1969; M. Bodanszky, et al., "Peptide Synthesis", John Wiley & Sons, Second Edition, 1976 and J. Meienhofer, "Hormonal Proteins and l'eptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

An $α_{6B}$ or $α_{3B}$-derived polypeptide can be used, inter alia, in the diagnostic methods and systems of the present invention to detect $α_{6B}$ or $α_{3B}$ present in a body sample, or can be used to prepare an inoculum as described herein for the preparation of antibodies that immunoreact with epitopes on the cytoplasmic domain of either $α_{6B}$ or $α_{3B}$.

C. DNA Segments

In living organisms, the amino acid residue sequence of a protein or polypeptide is directly related via the genetic code to the deoxyribonucleic acid (DNA) sequence of the structural gene that codes for the protein. Thus, a structural gene can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

In one embodiment the present invention contemplates an isolated DNA segment that comprises a nucleotide base sequence that encodes a polypeptide that includes the amino acid residue sequence defining the cytoplasmic domain of $α_{6B}$ or $α_{3B}$ as defined herein.

A DNA segment therefor has a nucleotide sequence encoding the human or mouse $α_{6B}$ or mouse $α_{3B}$ proteins, or at least encoding the cytoplasmic domain of those proteins. The nucleotide sequences are generally shown in SEQ ID NO 4 for human $α_{6B}$, NO 6 for mouse $α_{6B}$ and NO 10 for mouse $α_{3B}$.

Preferred DNA segments include a nucleotide base sequence represented by the base sequence contained in SEQ ID NO 4 from base 3279 to base 3418 and defining a coding sequence that translates into the cytoplasmic domain of $α_{6B}$. Particularly preferred is a nucleotide base sequence represented by the sequence contained in SEQ ID NO 4 from base 147 to base 3418 that defines the $α_{6B}$ integrin subunit. Corresponding nucleotide sequences for mouse $\alpha_{6B}$ in SEQ ID NO 6 are also contemplated.

In another embodiment, preferred DNA segments include a nucleotide base sequence represented by the base sequence contained in SEQ ID NO 10 from base 339 to base 463 and defining a coding sequence that translates into the cytoplasmic domain of $\alpha_{3B}$. Particularly preferred is a nucleotide base sequence represented by the sequence contained in SEQ ID NO 10 from base 1 to base 463 that defines the carboxy terminal portion of the $\alpha_{3B}$ integrin subunit, including the cytoplasmic domain of $\alpha_{3B}$.

In preferred embodiments, the length of the nucleotide base sequence is no more than about 3,000 bases, preferably no more than about 1,000 bases.

A purified DNA segment of this invention is substantially free of other nucleic acids that do not contain the nucleotide base sequences specified herein for a DNA segment of this invention, whether the DNA segment is present in the form of a composition containing the purified DNA segment, or as a solution suspension or particulate formulation. By substantially free is means that the DNA segment is present as at least 10% of the total nucleic acid present by weight, preferably greater than 50%, and more preferably greater than 90% of the total nucleic acid by weight.

In preferred embodiments, a DNA segment of the present invention is bound to a complementary DNA segment, thereby forming a double stranded DNA segment. In addition, it should be noted that a double stranded DNA segment of this invention preferably has a single stranded cohesive tail at one or both of its termini.

A DNA segment of the present invention can easily be synthesized by chemical techniques, for example, the phosphotriester method of Matteucci et al., *J. Am. Chem. Soc.*, 103:3185 (1981). (The disclosures of the art cited herein are incorporated herein by reference.) Of course, by chemically synthesizing the structural gene portion, any desired modifications can be made simply by substituting the appropriate bases for those encoding a native amino acid residue.

In addition, a DNA segment can be prepared by first synthesizing oligonucleonucleotides that correspond to portions of the DNA segment, which oligonucleotides are then assembled by hybridization and ligation into a complete DNA segment. Such methods are also well known in the art. See for example, Paterson et al., *Cell*, 48:441-452 (1987); and Lindley et al., *Proc. Natl. Acad. Sci.*, 85:9199-9203 (1988), where a recombinant peptide, neutrophil-activated factor, was produced from the expression of a chemically synthesized gene in *E. coli*.

A DNA expression vector of the present invention is a recombinant DNA (rDNA) molecule adapted for receiving and expressing translatable DNA sequences in the form of a fusion polypeptide of this invention. A DNA expression vector is characterized as being capable of expressing, in a compatible host, a structural gene product such as an $\alpha_{6B}$ or $\alpha_{3B}$ polypeptide of the present invention.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked.

As used herein, the term "operatively linked", in reference to DNA segments, describes that the nucleotide sequence is joined to the vector so that the sequence is under the transcriptional and/or translation control of the expression vector and can be expressed in a suitable host cell.

The choice of vector to which a structural gene is operatively linked depends directly, as is well known in the art, on the functional properties desired, e.g., vector replication and protein expression, and the host cell to be transformed, these being limitations inherent in the art of constructing recombinant DNA molecules.

In preferred embodiments, the vector utilized includes a prokaryotic replicon i.e., a DNA sequence having the ability to direct autonomous replication and maintenance of the recombinant DNA molecule extra chromosomally in a prokaryotic host cell, such as a bacterial host cell, transformed therewith. Such replicons are well known in the art. In addition, those embodiments that include a prokaryotic replicon also include a gene whose expression confers a selective advantage, such as drug resistance, to a bacterial host transformed therewith. Typical bacterial drug resistance genes are those that confer resistance to ampicillin or tetracycline. Vectors typically also contain convenient restriction sites for insertion of translatable DNA sequences. Exemplary vectors are the plasmids pUC8, pUC9, pBR322, and pBR329 available from BioRad Laboratories, (Richmond, Calif.) and pPL and pKK223 available from Pharmacia, (Piscataway, N.J.). Also contemplated are vctors for expressing a DNA segment of this invention in a yeast or mammalian host cell.

DNA expression control sequences include both 5' and 3' elements, as is well known, to form a cistron able to express a structural gene product. The 5' control sequences define a promoter for initiating transcription and a ribosome binding site operatively linked at the 5' terminus of the upstream translatable DNA sequence.

To achieve high levels of gene expression in E. coli, it is necessary to use not only strong promoters to generate large quantities of mRNA, but also ribosome binding sites to ensure that the mRNA is efficiently translated. In E. coli, the ribosome binding site includes an initiation codon (AUG) and a sequence 3-9 nucleotides long located 3-11 nucleotides upstream from the initiation codon [Shine et al., *Nature*, 254:34 (1975). The sequence, AGGAGGU, which is called the Shine-Dalgarno (SD) sequence, is complementary to the 3' end of *E. coli* 16S mRNA. Binding of the ribosome to mRNA and the sequence at the 3' end of the mRNA can be affected by several factors:

(i) The degree of complementarity between the SD sequence and 3' end of the 16S tRNA.

(ii) The spacing and possibly the DNA sequence lying between the SD sequence and the AUG [Roberts et al., *Proc. Natl. Acad. Sci. USA*. 76:760 (1979a); Roberts et al., *Proc. Natl. Acad. Sci. USA*, 76:5596 (1979b); Guarente et al., *Science*, 209:1428 (1980); and Guarente et al., *Cell*. 20:543 (1980).] Optimization is achieved by measuring the level of expression of genes in plasmids in which this spacing is systematically altered. Comparison of different mRNAs shows that there are statistically preferred sequences from positions −20 to +13 (where the A of the AUG is position 0) [Gold et al., *Annu. Rev. Microbiol.*, 35:365 (1981)]. Leader sequences have been shown to influence translation dramatically (Roberts et al., 1979 a, b supra).

(iii) The nucleotide sequence following the AUG, which affects ribosome binding [Taniguchi et al., *J. Mol. Biol.*, 118:533 (1978)].

D. Antibodies and Monoclonal Antibodies

The term "antibody" in its various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds (immunoreacts with) antigen. The term immunoreact in its various forms means specific binding between an antigenic determinant-containing molecule and a molecule containing an antibody combining site such as a whole antibody molecule or a portion thereof.

The phrase "antibody molecule" in its various grammatical forms as used herein contemplates both an intact immunoglobulin molecule and an immunologically active portion of an immunoglobulin molecule.

Exemplary antibody molecules for use in the diagnostic methods and systems of the present invention are intact immunoglobulin molecules, substantially intact immunoglobulin molecules and those portions of an immunoglobulin molecule that contain the paratope, including those portions known in the art as Fab, Fab', F(ab')$_2$ and F(v).

Fab and F(ab')$_2$ portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

An antibody of the present invention in one embodiment is an anti-cytoplasmic $\alpha_{6B}$ domain antibody characterized as being capable of immunoreacting with 1) human $\alpha_{6B}$, and 2) a polypeptide having a sequence shown in SEQ ID NO 3 from residue 1045 to residue 1091.

In another embodiment an antibody of this invention is an anti-cytoplasmic $\alpha_{6B}$ domain antibody characterized as being capable of immunoreacting with 1) human $\alpha_{6B}$, and 2) a polypeptide having a sequence shown in SEQ ID NO 3 from residue 1068-1091.

In another emobdiment an antibody of this invention is an anti-cytoplasmic $\alpha_{6B}$ domain antibody characterized as being capable of immunoreacting with 1) mouse $\alpha_{6B}$ and 2) a polypeptide having a sequence shown in SEQ ID NO 5 from residue 121 to residue 141.

In another embodiment, an anti-cytoplasmic $\alpha_{3B}$ domain antibody is contemplated that is characterized as being capable of immunoreacting with 1) mouse $\alpha_{3B}$, and 2) the polypeptide having a sequence shown in SEQ ID NO 9 from residue 113 to residue 153.

Antibody immunoreactivity with antigens containing a cytoplasmic domain as defined above can be measured by a variety of immunological assays known in the art.

Exemplary immunoreaction of a subject antibody with $\alpha_{6B}$ or $\alpha_{3B}$ polypeptides is described in Examples 2 and 4.

For example, immunoreaction with whole protein can be measured by the immunoprecipitation procedures described in Example 2. Immunoreaction of antibodies with polypeptides can be conveniently measured using ELISA as described in U.S. Pat. Nos. 3,643,090; No. 3,850,752; or No. 4,016,043, which are incorporated herein by reference, using the polypeptide in the solid phase, as is well know.

An antibody of the present invention is typically produced by immunizing a mammal with an inoculum containing a polypeptide of this invention and thereby induce in the mammal antibody molecules having immunospecificity for the polypeptide. Exemplary immunization procedures for preparing an antibody of this invention are described in Example 2. The antibody molecules are then collected from the mammal and isolated to the extent desired by well known techniques such as, for example, by using DEAE Sephadex to obtain the IgG fraction.

To enhance the specificity of the antibody, the antibodies may be purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

The antibody so produced can be used, inter alia, in the diagnostic methods and systems of the present invention to detect $\alpha_{6B}$ or $\alpha_{3B}$ subunits present in a body sample. See, for example, the methods described in Examples 2 and 4.

The word "inoculum" in its various grammatical forms is used herein to describe a composition containing a polypeptide of this invention as an active ingredient used for the preparation of antibodies against the cytoplasmic domain of an $\alpha_{6B}$ or $\alpha_{3B}$ polypeptide. When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, dialdehydes such as glutaraldehyde, Klipstein, et al., *J. Infect. Dis.*, 147:318–326 (1983) and the like, or the use of carbodiimide technology as in the use of a water-soluble carbodiimide to form amide links to the carrier. For a review of protein conjugation or coupling through activated functional groups, see Aurameas, et al., Scand. J. Immunol., 1:7-23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen as is well known in the art. Inocula typically contain polypeptide concentrations of about 10 micrograms to about 500 milligrams per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

The techniques of polypeptide conjugation or coupling through activated functional groups presently known in the art are particularly applicable. See, for example, Aurameas, et al., Scand. J. Immunol., Vol 8, Suppl. 7:7-23 (1978) and U.S. Pat. Nos. 4,493,795, No. 3,791,932 and No. 3,839,153. In addition, a site directed coupling reaction can be carried out so that any loss of activity due to polypeptide orientation after coupling can be minimized. See, for example, Rodwell et al., Biotech., 3:889-894 (1985), and U.S. Pat. No. 4,671,958.

One or more additional amino acid residues may be added to the amino- or carboxy-termini of the polypeptide to assist in binding the polypeptide to form a conjugate. Cysteine residues, usually added at the carboxy-terminus of the polypeptide, have been found to be particularly useful for forming conjugates via disulfide bonds, but other methods well-known in the art for preparing conjugates may be used.

A preferred antibody of this invention is a monoclonal antibody.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

A monoclonal antibody is typically composed of antibodies produced by clones of a single cell called a hybridoma that secretes (produces) but one kind of antibody molecule. The hybridoma cell is formed by fusing an antibody-producing cell and a myeloma or other self-perpetuating cell line. The preparation of such antibodies was first described by Kohler and Milstein, Nature 256:495-497 (1975), which description is incorporated by reference. The hybridoma supernates so prepared can be screened for the presence of antibody molecules that immunoreact with a polypeptide of this invention, or for inhibition of the natural function of an $\alpha_{6B}$ or $\alpha_{3B}$ subunit.

Briefly, to form the hybridoma from which the monoclonal antibody composition is produced, a myeloma or other self-perpetuating cell line is fused with lymphocytes obtained from the spleen of a mammal hyperimmunized with an antigen containing the cytoplasmic domain of $\alpha_{6B}$ or $\alpha_{3B}$, such as is present in a polypeptide of this invention. The polypeptide-induced hybridoma technology is described by Niman et al., Proc. Natl. Sci., U.S.A., 80:4949-4953 (1983), which description is incorporated herein by reference.

It is preferred that the myeloma cell line used to prepare a hybridoma be from the same species as the lymphocytes. Typically, a mouse of the strain 129 G1X+ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using an immunoassay such as the immunoprecipitation protocol described in Example 3.

A monoclonal antibody of the present invention can also be produced by initiating a monoclonal hybridoma culture comprising a nutrient medium containing a hybridoma that secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., Virol. 8:396 (1959)) supplemented with 4.5 gm/1 glucose, 20 mm glutamine, and 20% fetal calf serum. An exemplary inbred mouse strain is the Balb/c.

The monoclonal antibodies of this invention can be used in the same manner as disclosed herein for antibodies of the present invention.

For example, the monoclonal antibody can be used in the diagnostic methods and systems disclosed herein where formation of a cytoplasmic $\alpha_{6B}$ or $\alpha_{3B}$ domain-containing immunoreaction product is desired.

Other methods of producing a monoclonal antibody, a hybridoma cell, or a hybridoma cell culture are also well known. See, for example, the method of isolating monoclonal antibodies from an immunological repertoire as described by Sastry, et al., Proc. Natl. Acad. Sci., 86:5728–5732 (1989); Huse et al., Science, 246:1275–1281 (1989); and Mullinax et al, Proc.Natl.Acad.Sci.USA, 87:8095–8099 (1990).

Also contemplated by this invention is the hybridoma cell, and cultures containing a hybridoma cell that produce a monoclonal antibody of this invention.

D. Diagnostic Systems

The present invention also describes a diagnostic system, preferably in kit form, for assaying for the presence of antigen having the cytoplasmic domain of $\alpha_{6B}$ or $\alpha_{3B}$ in a body sample such as a tissue, body fluid or the like body sample. A diagnostic system includes, in an amount sufficient for at least one assay, a subject polypeptide and/or a subject antibody or monoclonal antibody, as a separately packaged immunochemical reagent. Instructions for use of the packaged reagent are also typically included.

As used herein, the term "package" refers to a solid matrix or material such as glass, plastic, paper, foil and the like capable of holding within fixed limits a polypeptide, polyclonal antibody or monoclonal antibody of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system for assaying for the presence of or to quantitate $\alpha_{6B}$ or $\alpha_{3B}$ in a sample, such as blood, plasma or serum, comprises a package containing at least one $\alpha_{6B}$ or $\alpha_{3B}$ derived polypeptide of this invention depending on whether $\alpha_{6B}$ or $\alpha_{3B}$ is to be detected, respectively. In another embodiment, a diagnostic system of the present invention for assaying for the presence or amount of $\alpha_{6B}$ or $\alpha_{3B}$ in a sample further includes an antibody composition of this invention. An exemplary diagnostic system is described in Example 4.

In preferred embodiments, a diagnostic system of the present invention further includes a label or indicating means capable of signaling the formation of an immunocomplex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in Antibody As a Tool, Marchalonis, et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emissionproducing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted pr duce gamma rays upon encounters with electrons present in the animal's body. Also useful is a beta emitter, such $^{111}$indium of $^3H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., Meth. Enzymol., 73:3–46 (1981). The techniques of protein conjugation or coupling through activated functional groups are particularly applicable. See, for example, Aurameas, et al., Scand. J. Immunol., Vol. 8 Suppl.

7:7–23 (1978), Rodwell et al., Biotech., 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of $\alpha_{6B}$ or $\alpha_{3B}$ subunit in a vascular fluid sample such as blood, serum, or plasma. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; No. 3,850,752; and No. 4,016,043, which are all incorporated herein by reference.

Thus, in preferred embodiments, a polypeptide or an antibody of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides well known to those skilled in the art, can be used.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

The term "package" refers to a solid matrix or material such as glass, plastic (e.g., polyethylene, polypropylene and polycarbonate), paper, foil and the like capable of holding within fixed limits a diagnostic reagent such as a polypeptide, antibody or monoclonal antibody of the present invention. Thus, for example, a package can be a bottle, vial, plastic and plastic-foil laminated envelope or the like container used to contain a contemplated diagnostic reagent or it can be a microtiter plate well to which microgram quantities of a contemplated diagnostic reagent have been operatively affixed, i.e., linked so as to be capable of being immunologically bound by an antibody or polypeptide to be detected.

F. Assay Methods

The present invention contemplates various immunoassay methods for determining the amount of $\alpha_{6B}$ or $\alpha_{3B}$ in a biological sample using a polypeptide, polyclonal antibody or monoclonal antibody of this invention as an immunochemical reagent to form an immunoreaction product whose amount relates, either directly or indirectly, to the amount of $\alpha_{6B}$ or $\alpha_{3B}$ in the sample.

Those skilled in the art will understand that there are numerous well known clinical diagnostic chemistry procedures in which an immunochemical reagent of this invention can be used to form an immunoreaction product whose amount relates to the amount of $\alpha_{6B}$ or $\alpha_{3B}$ present in a body sample. Thus, while exemplary assay methods are described herein, the invention is not so limited.

Various heterogeneous and homogeneous protocols, either competitive or noncompetitive, can be employed in performing an assay method of this invention, including radioimmunoprecipitation (RIP), solid phase immunoassay such as ELISA, in situ immunoreaction assays for direct binding of antigen in tissue samples, and the like immunoassay protocols.

Generally, to detect the presence of an $\alpha_{6B}$ or $\alpha_{3B}$ subunit or polypeptide in a patient, an aliquot (i.e., a predetermined amount) of a body fluid sample, such as urine or a vascular fluid, namely blood, plasma or serum from the patient, or a tissue sample prepared for immunoreaction, is contacted by admixture (admixed), with an antibody composition of the present invention to form an immunoreaction admixture. The admixture is then maintained under biological assay conditions (immunoreaction conditions) for a period of time sufficient for the $\alpha_{6B}$ or $\alpha_{3B}$ antigen present in the sample to immunoreact with (immunologically bind) a portion of the antibody combining sites present in the antibody composition to form a antigen-antibody molecule immunoreaction product (immunocomplex). The complex can then be detected as described herein. The presence of the complex is indicative of $\alpha_{6B}$ or $\alpha_{3B}$ subunit or polypeptide in the sample.

Maintenance time periods sufficient for immunoreaction are well known and are typically from about 10 minutes to about 16–20 hours at a temperature of about 4° C. to about 45° C., with the time and temperature typically being inversely related. For example, longer maintenance times are utilized at lower temperatures, such as 16 hours at 4° C., and shorter times for higher temperatures, such as 1 hour at room temperature.

Biological assay conditions are those that maintain the biological activity of the immunochemical reagents of this invention and the $\alpha_{6B}$ or $\alpha_{3B}$ subunit or polypeptide sought to be assayed such that the reagents retain their ability to form an immunoreaction product. Those conditions include a temperature range of about 4° C. to about 45° C., a pH value of about 5 to about 9 and an ionic strength varying from that of distilled water to that of about one molar sodium chloride. Methods for optimizing such maintenance time periods and biological assay conditions are well known in the art.

Determining the presence or amount of an $\alpha_{6B}$ or $\alpha_{3B}$ containing immunoreaction product formed by the above maintenance step, either directly or indirectly, can be accomplished by assay techniques well known in the art, and typically depend on the type of indicating means used.

In a direct binding assay format for detecting $\alpha_{6B}$ or $\alpha_{3B}$ in a tissue sample such as a tissue section, the antibody is reacted with the target antigen in situ to form the immunoreaction complex. thereafter, the immunocomplex is detected thereby indicating the presence of the antigen in the tissue. Exemplary and preferred in situ immunoassay formats are described in Example 4. Alternatively, the direct binding assay can be practiced with a fluid body sample believed to contain $\alpha_{6B}$ or $\alpha_{3B}$ subunits or polypeptides.

Thus, in this embodiment, the direct assay comprises the steps of:

(a) admixing a tissue sample or body fluid sample with an antibody composition of this invention immunospecific for a cytoplasmic domain of either $\alpha_{6B}$ or $\alpha_{3B}$ as described herein to form an immunoreaction admixture;

(b) maintaining said immunoreaction admixture under biological assay conditions for a time period sufficient to form an immunoreaction product; and (c) detecting the presence, and preferably amount, of the immunoreaction product formed phase in step (b), and thereby the amount of presence/amount of $\alpha_{6B}$ or $\alpha_{3B}$ in the sample.

More preferably, detecting in step (c) is performed by the steps of:

(i) admixing the immunoreaction product formed in step (b) with an indicating means to form a second reaction admixture;

(ii) maintaining the second reaction admixture for a time period sufficient for said indication means to bind the immunoreaction product formed in step (b) and form a second reaction product; and, (iii) determining the presence and/or amount of indicating means in the second reaction product, and thereby the presence of the immunoreaction product formed in step (b). Particularly preferred is the use of a labeled second antibody, immunospecific for the first antibody, as the indicating means, and preferably the label is horseradish peroxidase. In one embodiment, it is particularly preferred to use (1) mouse anti-cytoplasmic domain $\alpha_{6B}$ polypeptide antibody in the antibody composition, and (2) goat anti-mouse IgG antibodies labeled with horseradish peroxidase as the indicating means.

In a preferred competition assay method, the immunoreaction admixture described above further contains a solid phase having affixed thereto a solid phase antigen comprising an $\alpha_{6B}$ or $\alpha_{3B}$ subunit or polypeptide having an amino acid residue sequence that includes the cytoplasmic domain of $\alpha_{6B}$ or $\alpha_{3B}$, respectively, of this invention. Thus, in this embodiment, the assay comprises the steps of:

(a) admixing a body fluid sample with 1) an antibody composition of this invention and 2) a solid support having affixed thereto (operatively linked) an antigen comprising an $\alpha_{6B}$ or $\alpha_{3B}$ subunit or polypeptide having an amino acid residue sequence that includes the cytoplasmic domain of $\alpha_{6B}$ or $\alpha_{3B}$ of this invention, or both, to form an immunoreaction admixture having both a liquid phase and a solid phase;

(b) maintaining said immunoreaction admixture under biological assay conditions for a time period sufficient to form an immunoreaction product in the solid phase; and (c) detecting the presence, and preferably amount, of the immunoreaction product formed in the solid phase in step (b), and thereby the amount of presence/amount of one or both of $\alpha_{6B}$ and $\alpha_{3B}$ in the body fluid sample.

In another competition assay format the immunoreaction admixture contains (1) a body fluid sample, preferably cell free, (2) an antibody of this invention and (3) a labeled antigen comprising the cytoplasmic domain of $\alpha_{6B}$ or $\alpha_{3B}$, wherein the antibody is present in the solid phase, being affixed to a solid support, to form a liquid and a solid phase. In this embodiment, the admixed body fluid sample competes with the labeled reagent for immunoreaction with the solid phase antibody to form a solid phase immunoreaction product. Thereafter, the detection of label in the solid phase correlates with the amount of $\alpha_{6B}$ or $\alpha_{3B}$ in the admixed fluid sample.

In one embodiment, the detection of a polypeptide of this invention in a body sample is utilized as a means to monitor the fate of therapeuticallly administered $\alpha_{6B}$ or $\alpha_{3B}$ derived polypeptides according to the therapeutic methods disclosed herein.

Also contemplated are immunological assays capable of detecting the presence of immunoreaction product formation without the use of a label. Such methods employ a "detection means", which means are themselves well-known in clinical diagnostic chemistry and constitute a part of this invention only insofar as they are utilized with otherwise novel polypeptides, methods and systems. Exemplary detection means include methods known as biosensors and include biosensing methods based on detecting changes in the reflectivity of a surface, changes in the absorption of an evanescent wave by optical fibers or changes in the propagation of surface acoustical waves.

EXAMPLES

The following Examples illustrate, but do not limit, the present invention.

1. Polypeptides

Polypeptides were synthesized using the classical solid-phase technique described by Merrifield, *Adv. Enzymol.*, 32:221–96 (1969) as adapted for use with a Model 430A automated peptide synthesizer (Applied Biosystems, Foster City, Calif.). Polypeptide resins were cleaved by hydrogen fluoride, extracted and analyzed for purity by high-performance liquid chromatograph using a reverse-phase C18 column. (Waters Associates, Milford, Mass.).

The amino acid residue sequence of the polypeptides and their designations are as follows:

p$\alpha_6A$1  CIHAQPSDKERLTSDA
p$\alpha_6B$1  CDEKYIDNLEKKQWITKWNRNESYS

Polypeptide p$\alpha_{6A}$ has a sequence from the cytoplasmic domain of $\alpha_{6A}$ and is shown in SEQ ID NO 1 from residue 1059 to residue 1073 to which an additional cysteine residue was included at the N-terminus for coupling the peptide to a protein carrier (KLH) for immunization. Polypeptide $p\alpha_{6B}$ has a sequence from the cytoplasmic domain of $\alpha_{6B}$ and is shown in SEQ ID NO 3 from residue 1068 to residue 1091 to which an additional cysteine residue was included at the N-terminus for coupling the peptide to a protein carrier (KLH) for immunization.

2. Preparation of Polyclonal Antisera a. Conjugation of KLH

Briefly, as a generalized procedure for each polypeptide, 4 milligrams of KLH in 0.25 milliliters (ml) of 10 millimolar (mM) sodium phosphate buffer (pH 7.2) is reacted with 0.7 milligrams (mg) of MBS dissolved in DMF, and the resulting admixture is stirred for 30 minutes at room temperature. The MBS solution is added dropwise to ensure that the local concentration of DMF was not too high, as KLH is insoluble at DMF concentrations of about 30% or higher. The reaction product, KLH-MB, is passed through a chromatography column prepared with Sephadex G-25 (Pharmacia Fine Chemicals, Piscataway, N.J.) equilibrated with 50 mM sodium phosphate buffer (pH 6.0) to remove free MBS. KLH recovery from peak fractions of the column eluate, monitored at 280 nanometers, is typically approximately 80%.

The KLH-MB so prepared is then reacted with 5 mg of polypeptide dissolved in 1 ml of buffer. The pH value of the resulting reaction composition is adjusted to 7-7.5, and the reaction composition is stirred at room temperature for 3 hours to provide a polypeptide-carrier conjugate.

b. Immunization and Harvesting of Polyclonal Antisera

Inoculum stock solutions are prepared with CFA, IFA or alum as follows: An amount of the synthetic polypeptide-conjugate sufficient to provide the desired amount of polypeptide per inoculation is dissolved in phosphate-buffered saline (PBS) at a pH value of 7.2. Equal volumes of CFA, IFA or alum are then mixed with the polypeptide solution to provide an inoculum containing polypeptide, water and adjuvant in which the water-to-oil ratio is about 1:1. The mixture is thereafter homogenized to provide the inoculum stock solution.

Rabbits used herein to raise anti-polypeptide antibodies were injected subcutaneously with an inoculum comprising 200 micrograms (ug) of a polypeptide conjugate (polypeptide plus carrier) emulsified in complete Freund's adjuvant (CFA); 200 ug of polypeptide conjugate, incomplete in Freund's adjuvant (IFA); and 200 ug of polypeptide conjugate with 4 mg alum injected intraperitoneally on days 0, 14 and 21, respectively, of the immunization schedule. Each inoculation (immunization) consisted of four injections of the inoculum. Mice may be immunized in a similar way using about one tenth of the above dose per injection.

Animals are typically bled 4 and 15 weeks after the first injection. Control re-immune serum was obtained from each animal by bleeding just before the initial immunization.

Control inoculum stock solutions can also be prepared with keyhole limpet hemocyanin (KLH), KLH in IFA (incomplete Freund's adjuvant), KLH-alum absorbed, KLH-alum absorbed-pertussis, edestin, thyroglobulin, tetanus toxoid, tetanus toxoid in IFA, cholera toxoid and cholera toxoid in IFA.

Upon injection or other introduction of the antigen or inoculum into the host animal, the immune system of the animal responds by producing large amounts of antibody to the antigen. Since the specific antigenic determinant of the manufactured antigen; i.e., the antigen formed form the synthetic polypeptide linked to the carrier corresponds to the determinant of the natural antigen of interest, the host animal manufactures antibodies not only to the synthetic polypeptide to which the synthetic polypeptide antigen corresponds; i.e., to the $\alpha_{6B}$ protein.

c. Immunoreactivity of Anti-peptide Antisera With Native $\alpha_6$ Proteins

1. Protocols and Reagents

The rabbit polyclonal anti-$\alpha_6$ cytoplasmic domain antiserum designated 6844 was raised against the last 15 amino acids (SEQ ID NO 1, residue 1059 to residue 1073) (IHAQPSDKERLTSDA) of the reported human $\alpha_6$ ($\alpha_{6A}$) sequence (Tamura et al., *J. Cell. Biol.*, 111:1593-1604, 1990), to which an additional cystine residue was included at the N-terminus for coupling the peptide to a protein carrier (KLH) for immunization.

The rat monoclonal antibody, GoH3, is specific for an extracellular epitope on both the human and murine $\alpha_6$ subunits (Sonnenberg et al., *J. Biol. Chem.*, 262:10376-83, 1987). The isotype-matched control antibody, B3B4, recognizes the B lymphocyte specific antigen, CD23.

The anti-$\alpha_6$ specific monoclonal antibody, 35.13c, and the isotype matched control antibody, 439.9b, specific for the human $\beta_4$ integrin subunit, have been previously described (Kennel et al., *J. Biol. Chem.*, 264:15515-21, 1989).

Anti-peptide antisera to the cytoplasmic domains of rat $\alpha_1$, chicken $\alpha_3$, human $\alpha_4$, human $\alpha_5$ and human $\beta_1$ sequences were shown to be cross-reactive with the respective were shown to be cross-reactive with the of B16F1 melanoma, STO fibroblast and MMT carcinoma murine cell lines.

Antisera to the cytoplasmic domain of human $\alpha_{6B}$ were prepared by immunizations of rabbits with the peptide $p\alpha_{6B}1$ having the sequence (SEQ ID NO 3, residue 1068 to residue 1091 beginning at the second residue of the following sequence) CDEKYIDNLEKKQWITKWNRNESYS as described above to which an additional cysteine residue was included at the N-terminus for coupling the peptide to a protein carrier (KLH) for immunization. This antisera is designated 382.

The ES cells and B16F1 cell line were used in these immunoreaction studies. The ES cell line, CCE (Schwartzberg et al., *Science.* 246:799-803, 1989) was initially cultured on murine embryonic fibroblasts (STO cells) to prevent differentiation. However, in order to study the expression and function of integrins in this ES cell line it was necessary to remove the STO cells from the culture system. Therefore, the CCE ES cell line was subcloned into LIF ($10^3$ units/ml) (Amrad Co. Australia) containing media (DMEM; 10% FCS, 100mM $\beta$-mercaptoethanol, 2mM glutamine). LIF has been shown to prevent ES cell differentiation (Moreau et al.,*Nature*, 336:690-92, 1988; Smith et al.,*Nature.* 336:688-90, 1988; Williams et al.,*Nature*, 336:684-687, 1988). The sublines were cultured on gelatin (0.1%) coated plates. Several subclones were expanded and continually cultured in LIF containing media. The subline ES1 was chosen for the studies described here. ES1 cells were allowed to differentiate on gelatin (0.1%) coated plates over a period of 8-9 days in the absence of LIF.

The murine B16FI melanoma line, obtained from Dr. Ralph Reisfeld (Scripps Clinic, La Jolla, Calif.), was derived from a C57Bl/6 melanoma and cultured in DMEM, 5% FCS, 2mM glutamine and penicillin-streptomycin (50 IU/ml-50ug/ml).

Undifferentiated ES cells ($1-2 \times 10^7$ cells) were surface labeled with Na$^{125}$I using the lactoperoxidase procedure (Roth, *Methods Enzymol.*, 37(B):223-33, 1975). Differentiated ES cells proved to be significantly more fragile than undifferentiated ES cells and did not survive the more rigorous washing steps required during the iodination procedure. Therefore, differentiated ES cells were metabolically labeled with [$^{35}$S]methionine as described previously by Kajiji et al, *EMBO J.*, 8:673-680 (1989). Preparation of non-ionic detergent cell lysates, immunoprecipitations and analysis by SDS-PAGE were performed as described by Kajiji et al (1989), supra.

Immunoprecipitation is conducted generally by first admixing the rabbit polyclonal antisera produced above with a cell lystate and maintaining the admixture for a time period sufficient for immunocomplexes to form. Thereafter, the immunoadsorbent Pansorbin (Sigma Chemical Co., St. Louis, Mo.) is added to the admixture containing the innunocomplexes and maintained to allow the Pansorbin to complex with (bind) the immunocomplex. Thereafter the Pansorbin-containing bound immunocomplexes are removed from the lysate admixture by centrifugation, washed several times and the washed immunocomplexes are released from the Pansorbin and analyzed by SDS-PAGE.

Sequential immunoprecipitation was also performed to identify the presence of multiple immunoreactive species in a single lystate. After a first immunoprecipitation as above the lysate is retained and subjected to a second immunoprecipitation with unbound Pansorbin. The resulting lysate from the second immunoprecipitation is again retained and subjected to a third immunoprecipitation with unbound Pansorbin. Thus by the successive rounds of sequential immunoprecipitation of a lysate using the same antibody species, that lysate becomes depleted of antigen immunoreactive with that antibody species. Thereafter, the depleted lysate is divided into aliquots and each aliquot is separately immunoprecipitated (re-IP or re-immunoprecipitated) using different antibodies. Antigens in the depleteld lysate that immunoprecipitate with the second antibody different from the depleting first antibody are not immunoreactive with the first antibody. By sequential immunoprecipitation, two non-cross reacting antigen species can be identified. As described herein, the cytoplasmic domains of $\alpha_{6A}$ and $\alpha_{6B}$ are not cross reactive.

Mouse $\alpha_6$

Separate immunoprecipitations were carried out on undifferentiated murine ES1 cells with antiserum 382 raised against a synthetic peptide corresponding to the sequence of the cytoplasmic tail of human $\alpha_{6B}$, with control preimmune serum from the same rabbit, and with antisera 6844 directed to the cytoplasmic tail of human 6A. Only antisera 382 precipitated protein bands virtually identical to those reactive with anti-$\alpha_6$ monoclonal GoH3 which is specific for both $\alpha_{6A}$ and $\alpha_{6B}$. These data indicated that ES1 cells do express $\alpha_{6B}$ protein, probably complexed with $\beta_1$, and antisera 382 is capable of recognizing the $\alpha_{6B}$ protein.

In contrast to the immunoprecipitation data from undifferentiated ES1 cells, the anti-$\alpha_{6A}$ cytoplasmic domain polyclonal antiserum, 6844, could immunoprecipitate the $\alpha_{6A}$ isoform from $^{35}$S-methionine labelled lysates obtained from differentiated ES1 cells. Thus, differentiation of ES1 cells is accompanied by the induction of expression of the $\alpha_{6A}$ isoform.

Figure 1B:
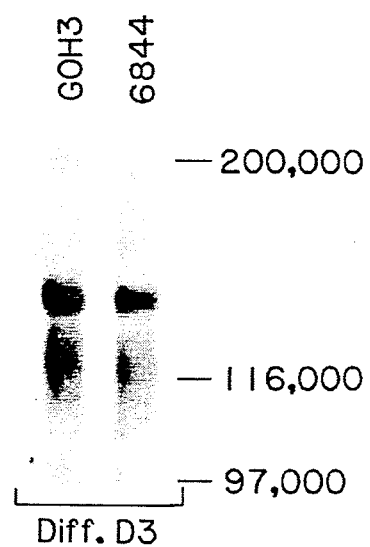

The absence of the $\alpha_{6A}$ isoform in differentiated ES1 cells can be seen by immunoprecipitations using GoH3 or 6844, which is shown in FIG. 1. Whereas the GoH3 antibody detects the lower molecular weight species corresponding to $\alpha_6$, the 6844 antibody, immunospecific for $\alpha_{6A}$, does not detect any $\alpha_6$ species, indicating that the GoH3-reactive form is an isoform, namely $\alpha_{6B}$.

Similar immunoprecipitation assays were carried out on the D3 ES cell line (see FIG. 1). The D3 embryonic stem cell line was derived by Doetschman et al., *J. Embryol. Exp. Morph.*, 87:27-45, (1985). D3 cells were cultured in LIF containing medium as described above except that 15% FCS was used. Immunoprecipitations of [$^{35}$S]methionine-labelled lysates showed that the $\alpha_{6B}$ isoform is expressed at the protein level in both undifferentiated and differentiated D3 cells while the $\alpha_{6A}$ isoform was found only in the differentiated cells. This would suggest that the ability to switch on $\alpha_{6A}$ expression upon differentiation may be a general property of ES cells.

Because the 382 antisera was raised to a human $\alpha_{6B}$ cytoplasmic domain-derived polypeptide and yet is shown above to immunoreact with the mouse $\alpha_{6B}$ protein, the above data also shows that an anti-$\alpha_{6B}$ antibody, whether raised to human or mouse varieties of $\alpha_{6B}$ can be used to immunoreact with both human or mouse $\alpha_{6B}$.

Human $\alpha_6$

Figure 2:
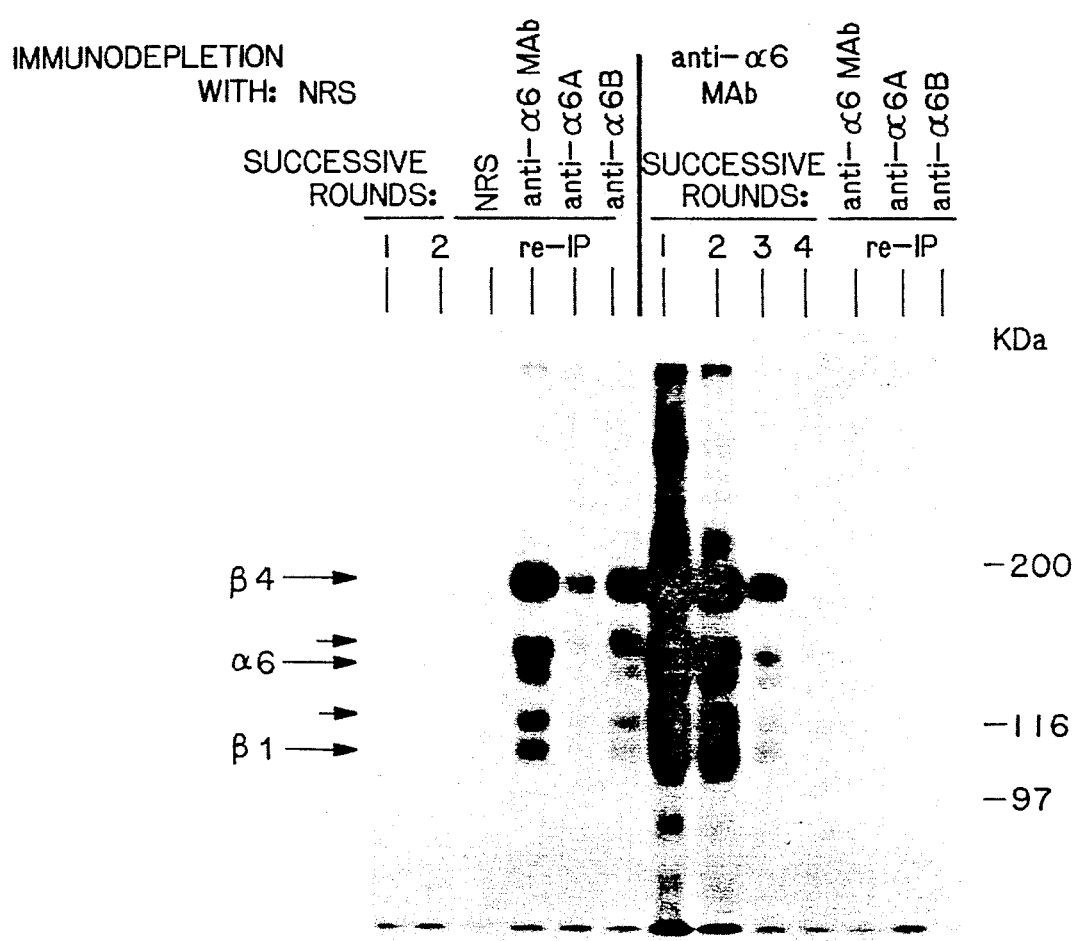
FIGS. 2 and 3 illustrate a sequential immunoprecipitation analysis of $\alpha_6$ subunits in human JAR cell lysates as described in Example 2. NRS is normal rabbit preimmune sera, anti-$\alpha_6$ Mab is GoH3, anti-$\alpha_{6A}$ is sera 6844 and anti-$\alpha_{6B}$ is sera 382. The molecular weight of standard protein markers is shown on the right side of the gel and is expressed in kilodaltons (KDa).

Antisera 382 to a synthetic peptide corresponding to the last 25 residues of human $\alpha_{6B}$ immunoprecipitated from radiolabeled detergent lysates of the human choriocarcinoma cell line JAR (see Example 4 for description of JAR cells) a pattern of bands similar or identical to those obtained with 6844, an anti-peptide antiserum to the $\alpha_{6A}$ cytoplasmic domain, and GoH3, a monoclonal antibody to the extracellular domain of $\alpha_6$ (see FIG. 2). The bands corresponded in molecular weight to $\alpha_6$, $\beta_1$ and $\beta_4$, and were positively identified as such with specific antibodies. This result is compatible with JAR cells expressing both $\alpha_6\beta_1$ and $\alpha_6\beta_4$ heterodimers, and with PCR amplifications detecting both $\alpha_{6A}$ and $\alpha_{6B}$ isoform bands in JAR cells (see Example 3).

Figure 3:
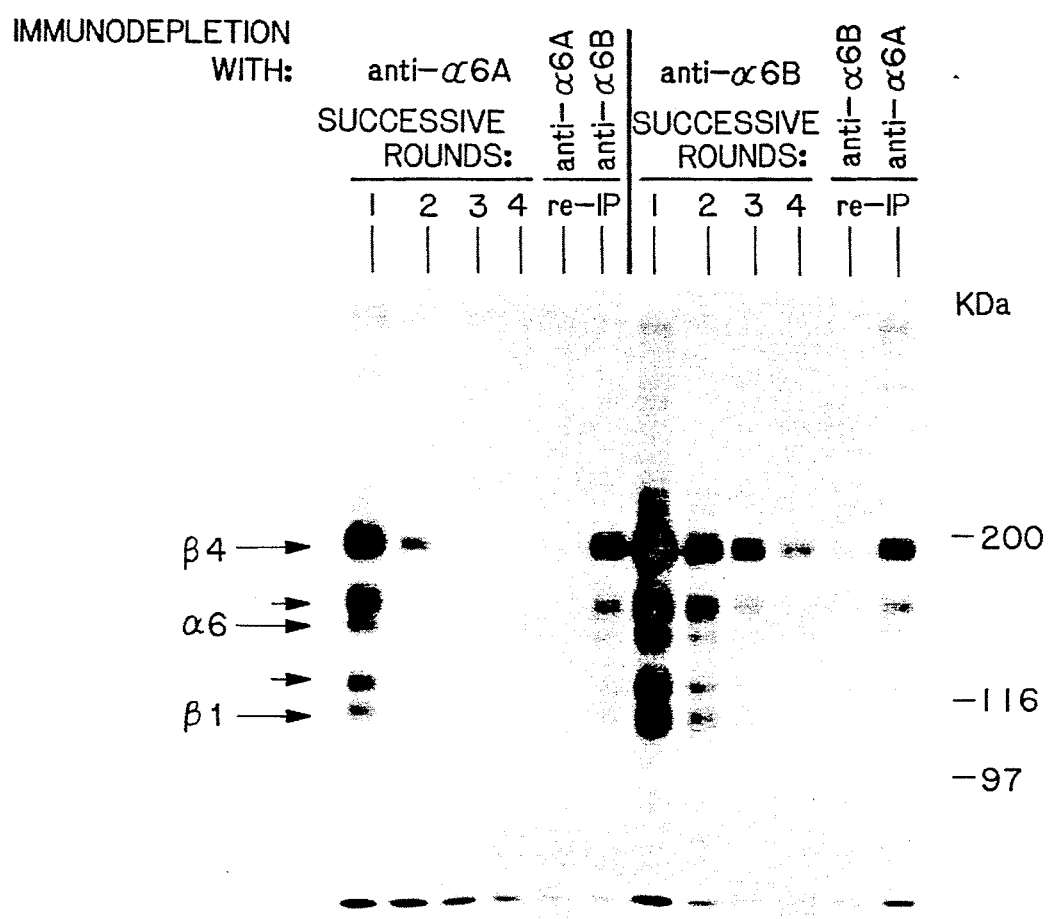

Sequential immunoprecipitations (FIG. 3) showed that antibody GoH3 completely depleted the JAR lysates of antigen reactive with antisera 382 (anti-$\alpha_{6B}$) or 6844 (anti-$\alpha_{6A}$). The 382 antiserum did not remove any material reactive with 6844, and 6844 did not remove any 382-reactive material, while both antisera reduced, but did not completely remove GoH3 reactivity (FIG. 2). These results indicate that JAR cells express both $\alpha_{6A}$ and $\alpha_{6B}$ proteins, each of which is paired with either $\beta_1$ or $\beta_4$. These results also indicate that antisera raised to a mouse protein, namely the cytoplasmic domain of mouse $\alpha_{6B}$, immunoreacts with its human counterpart protein, human $\alpha_{6B}$.

3. Identification and Cloning of $\alpha_{6B}$ and $_{3B}$ cDNAs cDNA molecules encoding human and mouse $\alpha_{6B}$ and mouse $\alpha_{3B}$ cytoplasmic regions were prepared and fragments of the cDNA molecules were selectively amplified using the polymerase chain reaction (PCR) in the presence of specific oligonucleotide primers in order to characterize gene expression of the $\alpha_{6B}$ and $\alpha_{3B}$ proteins.

a. Procotols

Poly-A+mRNA was isolated from human JAR cells (Ameriacan Tissue Type Collection, ATCC, Bethesda, Md., ATCC HTB 144), human U937 cells (ATCC CRL 1591), human FG cells (Dr. P. Meitner, Brown University) and both differentiated and undifferentiated cell lines using the Invitrogen Fastrack Kit (Invitrogen, La Jolla, Calif.). Single stranded cDNA was synthesized from 10 ug of mRNA using AMV reverse transcriptase (20U; Molecular Genetics Resources, Tampa, Fla.) and one ug of random hexamer primers (Pharmacia). The cDNAs were extracted with phenol/chloroform, then ethanol precipitated and about 0.5 to 10 ug cDNA was resuspended in 50-70ul of sterile water.

One ul of the resuspended cDNA was amplified per 50 ul PCR reaction mixture (2.5mM MgCl2, 50mM KCl, 10 mM $\beta$-mercaptoethanol, 66 mM Tris.HCl; pH8.3) using 0.1 uM oligonucleotide primers, 0.25 mM each of dATP, dTTP, dCTP, and dGTP, and 1.25U of TAQ 1 polymerase (AmpliTaq; Perkin Elmer/Cetus, Ca.). The PCR program consisted of 2 steps: (a) 40 cycles of 1 min at 94° C, 2 min at 55° C., and 3 min at 72° C. with a 5 sec/cycle extension on the 72° C. segment, (b) 10 min at 72° C. and a final shift to 4° C. Second round PCR was carried out on one ul of the reaction mixture generated from the first round PCR.

Nested pairs of PCR primers were employed to ensure that $\alpha_6$ specific fragments were amplified. Both sets of $\alpha_6$ primers were derived from the human $\alpha_{6A}$ cDNA sequence as determined by Tamura et al., *J. Cell. Biol.*, 111:1593-1604, (1990). The first set corresponded to bp 2918-2937 (primer 1157) and 3454-3473 (primer 1156) of the human $\alpha_{6A}$ sequence while the nested primer pair corresponded to bp 2942-2960 (primer 1681) and 3433-3452 (primer 2002). The sequence of these four primers are shown in SEQ ID NOS 11-14, respectively. $\alpha_3$ PCR primers designated primer 2032 and 2033 were derived from the hamster cDNA sequence as determined by Tsuji et al., *J. Biol. Chem.*, 265:7016-7021 (1990). The sequence of primers 2032 and 2033 are shown in SEQ ID NOS 15 and 16, respectively.

Oligonucleotide primers were chemically synthesized by using a "Gene Assembler" automated synthesizer (Pharmacia, Piscataway, N.J.).

Amplified fragments from first round PCR were purified using Gene Clean (Bio 101, La Jolla, Calif.), treated with DNA polymerase I and T4 polynucleotide kinase, again purified with Gene Clean, and the blunt-ended fragments were subcloned into the EcoRV site of Bluescript-pKS+(Stratagene,La Jolla, Calif.). Clones containing insert were sequenced manually (Sequenase kit; USB, Cleveland, Ohio) according to the manufacturer's instructions using T3 and T7 polymerase vector primer sequences. Sequences were analyzed on a VAX-VMS, version 5.2 computer, with programs of the University of Wisconsin Genetics Computer Group (Devereux et al, *Nucl. Acids Res.*, 12:387-395, 1984).

b. Results i. Human $\alpha_6$

Figure 4:
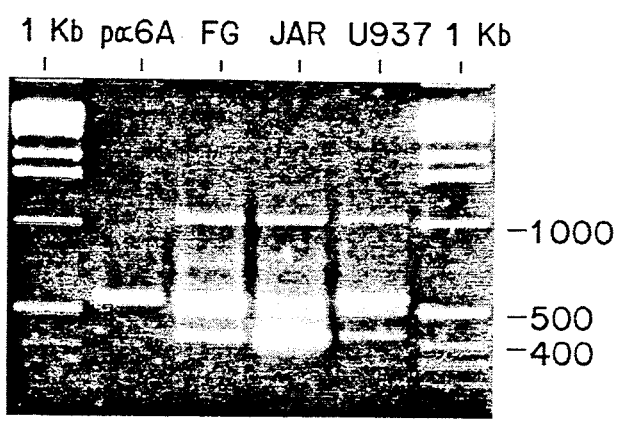
FIG. 4 shows $\alpha_{6A}$ and $\alpha_{6B}$ PCR amplification products visualized on an ethidium stained gel. Single-stranded cDNA was generated from human PG, JAR and U937 cells and was amplified with a set of primers, 1156 and 1157, specific for the human $\alpha_{6A}$ sequence as described in Example 3. The primers were also used to amplify the cloned human $\alpha_{6A}$ cDNA sequence, which yielded an amplification product of about 540 bp. The amplification products from the tested cell lines were either 540 bp or 410 bp, or both.

Oligonucleotides 1156 and 1157 flanking the 3' end of the coding region of integrin $\alpha_6$ mRNA were used as primers in polymerase chain reactions (PCR). Two products, of 540 bp and 410 bp, were obtained using first strand cDNAs from various cell lines as templates (FIG. 4). These same products were obtained in second-round PCR with a nested set of primers, indicating their specificity.

Both the 540bp and the 410bp PCR products were subcloned and sequenced. The nucleotide sequence of the 540 bp fragment (designated $\alpha_{6A}$ in FIG. 5) matches exactly the sequence of $\alpha_{6A}$ mRNA recently reported by Tamura et al., *J. Cell. Biol.*, 15 111:1593-1604, 1990, and encodes the 3' portion of the end of the extracellular domain, the transmembrane and the cytoplasmic domains, followed by the initial part of the 3' untranslated region (3' UT).

The sequence of the 410 bp band matches the 540 bp sequence, with the exception of a 130 bp gap shown in the lower sequence of FIG. 5, which lower sequence corresponds to the nucleotide sequence of $\alpha_{6B}$. This gap corresponds to the region encoding the predicted $\alpha_{6A}$ cytoplasmic domain, from the boundary with the transmembrane domain to 25 bp past the stop codon. Without this 130 bp segment, however, the open reading frame continues in the previous 3' UT, resulting in an $\alpha_{6B}$ protein with an alternative cytoplasmic domain (FIG. 6). This alternative domain is 17 amino acid longer than, and bears no sequence homology with, the reported $\alpha$6A cytoplasmic domain, but it does contain the sequence GFFKR, a motif present at the upstream border of all mammalian integrin $\alpha$ chains sequenced. For convenience, the published $\alpha_6$ sequence is referred to as $\alpha_{6A}$, and the $\alpha_6$ having the isoform cytoplasmic domain identified herein is referred to as $\alpha_{6B}$.

ii. Mouse $\alpha_6$

Figure 7A:
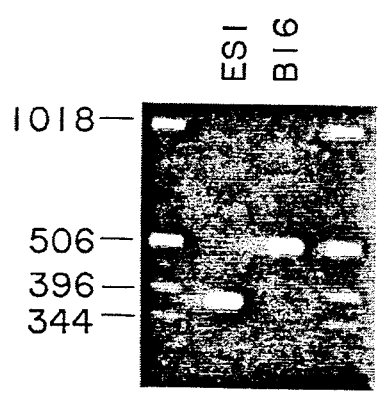
FIG. 7A and 7B depicts an ethidium bromide-stained gel of the PCR amplification products generated from (A) undifferentiated ES1 and B16 cells and (B) undifferentiated and differentiated ES1 cells as described in Example 3. The same priming oligonucleotides were used to amplify cDNA from these cells.

Amplification of mouse $\alpha_6$ cDNA expressed by undifferentiated ES1 and B16F1 cells was performed on first strand cDNA derived from these mouse cells using the polymerase chain reaction (PCR). The nested sets of PCR primers, pairs 1157/1156 and 1681/2002 described above, were employed. FIG. 7A shows the PCR products obtained.

The PCR fragment amplified from B16F1 ("B16") cDNA correspond to the size expected (510 bp) for the murine homologue of the human $\alpha_6$ (FIG. 7A; lane 2). However, the PCR fragment obtained from the amplification of the ES1 cell cDNA was significantly smaller. Amplification of cDNAs derived from four independent ES1 mRNA preparations yielded only the smaller fragment and never the larger fragment amplified from B16F1 cDNA.

The PCR fragments from the ES1 and B16F1 cells were subcloned into the Bluescript-pKS+vector and sequenced. FIG. 8 shows the nucleotide sequences of the two PCR fragments. The sequence of the larger B16F1 fragment was shown to be 89% identical to the human $\alpha_{6A}$ sequence at the nucleotide level and 91% identical at the amino acid level, Tamura et al., *J. Cell Biol.*, 111:1593-1604 (1990). Thus the larger frament's sequence represents the murine homologue of the human $\alpha$6A subunit. The B16FI PCR fragment (FIG. 8) encodes the C-terminal portion of the extracellular domain as well as the transmembrane and cytoplasmic domains of the $\alpha_6$ subunit. Due to the selection of primers, additional coding sequences 3' to the terminus of the sequence shown in FIG. 8 were not detected. Thus, additional amino acid residues not shown in FIG. 8 are present in the native mouse $\alpha_{6B}$ protein.

The sequence of the smaller PCR fragment (FIG. 8) was identical to the B16F1 sequence except that an internal deletion of 130 bp was observed. The location of the 130 bp deletion observed in the ES1 $\alpha_6$ PCR fragment exactly matched that of the human $\alpha_{6B}$ sequence. Therefore, ES1 cells expressed the murine equivalent of the $\alpha_{6B}$ isoform.

iii. Mouse $\alpha_3$

Expression of the $\alpha_3$ isoforms was also investigated in various mouse tissues including muscle, heart, brain, lung and ovary. Using the PCR procedure described above with the hamster $\alpha_3$ primers, a larger band corresponding to $\alpha_{3A}$ was amplified from most tissues except heart, kidney, liver, thymus and spleen (Table 2;Example 4). A smaller band corresponding to $\alpha_{3B}$ was detected in heart and brain. Cloning and sequencing of these bands showed that the larger band corresponds exactly to the reported $\alpha_3$ sequence ($\alpha_{3A}$), while the smaller band lacks a 144 bp segment and, like $\alpha_{6B}$, encodes an $\alpha_3$ with an alternative cytoplasmic tail ($\alpha_{3B}$). The amino acid residue and nucleotide sequences of the mouse $\alpha_{3B}$ cDNA-derived PCR fragments are shown in SEQ ID NOS 9 and 10, respectively.

4. Tissue distribution of $\alpha_{6A}$, $\alpha_{6B}$, $\alpha_{3A}$ and $\alpha hd$ 3B a. PCR Amplification The distribution of the $\alpha_6$ isoforms in cultured cell lines and mouse tissue was assessed by PCR as described in Example 3. The majority of the cells tested contained both $\alpha_{6A}$ and $\alpha_{6B}$ mRNA (see Tables 1 and 2). However, the two isoforms were reproducibly found at ratios characteristic of a cell line. Interestingly, two carcinoma cell lines and three lines of mouse embryonic fibroblasts (immortalized, non-tranformed) contained exclusively $\alpha_{6A}$, while embryonic stem cells and F9 teratocarcinoma cells contained exclusively $\alpha_{6B}$ (Table 1).

TABLE 1

| CELL LINE | CELL TYPE | $\alpha_{6A}$ | | $\alpha_{6B}$ | $\alpha_{3A}$ | $\alpha_{3B}$ |
|---|---|---|---|---|---|---|
| FG | Pancreatic Carcinoma | + | > | + | + | − |
| 1320 Met | " | + | > | + | ND | ND |
| Panc-1 | " | + | > | + | + | − |
| SGR | " | + | > | + | ND | ND |
| JAR | Choriocarcinoma | + | < | + | + | − |
| JEG-3 | " | + | < | + | ND | ND |
| BeWo | " | + | < | + | ND | ND |
| LoVo | Colon Carcinoma | + | < | + | ND | ND |
| Colo 396 | " | + | < | + | + | − |
| CaCo-2 | " | + | | + | + | − |
| HT-29 | " | + | > | + | + | − |
| HeLa | Cervical Carcinoma | + | > | + | ND | ND |
| UCLA-P3 | Lung Carcinoma | + | > | + | + | − |
| A431 | Epidermoid Carcinoma | + | | − | ND | ND |
| K562 | Erythroleukemia | + | | + | ND | ND |
| U937 | Histiocytic Lymphoma | + | > | + | + | − |
| 804G(Rat) | Bladder Carcinoma | + | | − | + | − |
| 3T3 (M) | Embryonic Fibroblast | + | | − | + | − |
| F9 (M) | Teratocarcinoma | − | | + | + | − |
| ES (M) | Embryonic Stem | − | | + | + | − |
| ES (M) | (Differentiated) | + | | + | ND | ND |

Cells were analysed by PCR amplification of $\alpha_6$ and $\alpha_3$ isoforms using the following human or mouse cells, with the cell sources indicated in parenthesis: pancreatic carcinoma: FG, SGR and 1320 Met cells (Dr. P. Meitner, Brown University); Panc-1 cells (ATCC CRL 1469); choriocarcinoma: JAR cells (ATCC HTB 144); JEG-3 cells (ATCC HTB 36); BeWo cells (ATCC CCL 98); colon carcinoma: LoVo cells (ATCC CCL 229 ); Colo 396 cells (Dr. T. Edgington, Scripps Clinic, La Jolla, Calif.); CaCo-2 cells (ATCC HTB 37); HT-29 cells (ATCC HTB 38); Hela cervical carcinoma cells (ATCC CCL 2); UCLA-P3 lung carcinoma cells (L. Walker, Scripps); A431 epidermoid carcinoma cells (ATCC CRL 1555); K562 erythroleukemia cells (ATCC CCL 243); U937 histiocytic lymphoma cells (ATCC CCL 1593); 8049 rat bladder carcinoma cells (J. Jones, Northwestern University, Evanston, Ill.); NIH/3T3 mouse embryo fibroblasts (ATCC CRL 1658); F9 mouse teratocarcinoma cells ATCC CRL 1720); ES mouse embryonic stem cells (E. Robertson, Columbia University, N.Y.).

Table 1 illustrates the distinction of $\alpha_{6A}$ and $\alpha_{6B}$, and $\alpha_{3A}$ and $\alpha_{3B}$ subunit-encoding mRNAs in human and mouse cultured cell lines. PCR amplification was performed on single-stranded cDNA generated from each cell type, using oligonucleotides specific for the $\alpha_6$ or $\alpha_3$ subunit, respectively. The (+) symbol represents the presence of subunit-specific amplification product in the tested sample, the (−) symbol represents its absence, and (ND) indicates that analysis was not conducted on that tissue type. The (>) is used when the $\alpha_{6A}$ subunit mRNA predominates over the $\alpha_{6B}$ subunit mRNA, and the (<) symbol is used when the $\alpha_{6B}$ subunit mRNA is the predominant species in the tissue.

By the same PCR assay, normal mouse lung, liver, spleen and cervix tissues were solely $\alpha_{6A}$, brain, ovary and kidney were solely $\alpha_{6B}$, while all other tissues tested contained both $\alpha_6$ isoforms (Table 2).

TABLE 2

| TISSUE | $\alpha_{6A}$ | | $\alpha_{6B}$ | $\alpha_{3A}$ | | $\alpha_{3B}$ |
|---|---|---|---|---|---|---|
| Muscle | + | > | + | + | | − |
| Heart | + | > | + | − | | + |
| Kidney | − | | + | − | | − |
| Liver | + | | − | − | | − |
| Brain | − | | + | + | < | + |
| Lung | + | | − | + | | − |
| Stomach | + | < | + | ND | | ND |
| Intestine | + | < | + | ND | | ND |
| Cervix | + | | − | ND | | ND |
| Submax | + | | + | ND | | ND |
| Ovary | − | | + | + | | − |
| Thymus | + | > | + | − | | − |
| Spleen | + | | − | − | | − |

Table 2 illustrates the distribution of $\alpha_{6A}$ and B and $\alpha_{3A}$ and B subunit-encoding mRNAs in mouse tissues. The symbols in Table 2 are the same as in Table 1.

Figure 7B:
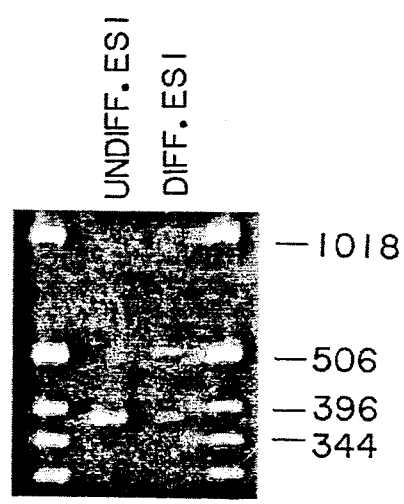

Primary and nested PCR reactions were carried out on differentiated cell lines as described in Example 3. ES1 cells were allowed to differentiate over a period of 8–9 days in the absence of Leukemia Inhibitory Factor (LIF). The morphology of the differentiated cells was dramatically different from that of undifferentiated ES1 cells maintained in LIF. PCR amplification on cDNA from undifferentiated ES1 cells, using $\alpha_6$ specific primers, produced the 380 bp fragment corresponding to the $\alpha_{6B}$ cytoplasmic sequence (FIG. 7B, lane 1). However, similar amplification of cDNA from the differentiated cells produced two distinct fragments of 510 bp and 380 bp (FIG. 7B, lane 2), shown by nucleotide sequencing to be the $\alpha_{6A}$ and $\alpha_{6B}$ isoforms, respectively.

b. In Situ Immunostaining of Tissues to Detect Tissue Distribution

Kidney biopsy materials were obtained by percutaneous needle biopsies using modified Vim-Silverman needles in patients with glomerulonephritis. A small portion of kidney biopsy materials were fixed with 4% paraformaldehyde for 4 hours at 4.C and embedded in paraffin using an automatic processor (Tissue-Tek$^R$ Rotary Tissue Processor). The tissue was cut in 4 micron thickness with an AO rotary microtome, and deparafinized with xylene or Histoclear (Baxter) and rehydrated with graded alchohol. The rehydrated sections were washed with 0.1 M glycine in TBS (0.005 M Tris-HCl; 0.9% NaCl, pH 7.5) for 5 minutes, treated with 0.1% Triton X-100 for 2 min at room temperature (RT), and trypsinized (0.1% trypsin for 5 min at 37° C.). Nonspecific binding sites were saturated by a blocking solution (5% dry milk solids, 1% heat inactivated horse serum in TBS) for 30 minutes. Serially diluted primary antibodies [1 ug/ul of 33% saturated ammonium sulfate (SAS) cut of antisera 6844 and 382; 1:10 to 1:1000 dilutions in reagent diluent: i.e. 2.5% bovine serum albumin in TBS] and normal control (SAS cut of normal rabbit serum, 1ug/ul, 1:10 to 1:1000 dilution in reagent diluent) were incubated on sections in humidified chambers at room temperature for 1 hr. Tissue sections were further incubated with peroxidase conjugated goat anti-rabbit antibody (Jackson Immunology) in reagent diluent (1:200) for 30 minutes. After this, 0.02% AEC (3-Amino-α-ethylcarbozole, Aldrich) was applied for 30 minutes at room temperature. Each step was followed by 3-minute washes in 0.005 M Tris-HCl, 0.9% NaCl pH 7.5 (TBS wash). Washed tissue sections were counterstained with Mayor's hematoxylin for 30 sec, mounted in Gel Mount (Biomeda) and observed under a light microscope.

Figure 9A:
FIGS. 9A and 9B illustrates the results of in situ immunostaining of diseased human kidney tissue. Panel A is stained with polyclonal antisera 6488 specific for the $\alpha_{6A}$ cytoplasmic region. Panel B is stained with polyclonal antisera 382 specific for the $\alpha_{6B}$ cytoplasmic region.
Figure 9B:

The results of the in situ immunostained kidney sections using the anti-peptide antisera specific for $\alpha_{6A}$ (6844) or specific for $\alpha_{6B}$ (382) are shown in FIG. 9. Panel A shows anti-$\alpha_{6A}$ antibody molecules staining podocytes in the glomelular structure of the kidney but no staining in the tubules of the kidney. Panel B shows anti-$\alpha_{6B}$ antibody molecules staining the epithelial cells of the distal or collecting tubules of the kidney but not the glomerular cells.

Additional kidney samples were similarly analysed and the results are shown in Table 3.

TABLE 3[1]

| Patient | Sera 6488 | | Sera 382 | |
|---|---|---|---|---|
| | G | T | G | T |
| Normal | − | − | − | − |
| 1 | + | − | − | + |
| 2 | ++ | ± | − | ++ |
| 3 | +++ | − | − | +++ |
| 4 | +++ | − | − | ++++ |
| 5 | ++++ | − | − | ++++ |

[1]"G" indicates the immunostaining pattern observed in glomerular epithelial cells of the kidney, whereas "T" indicates the immunostaining pattern observed in the tubular epithelial cells, where (−) indicates no staining and + to ++++ indicates increasing intensities of stain. Patients 1-5 are patients that all have glomerular nephritis clinically indicated as to require kidney biopsy.

The results in Table 3 indicate that in all patients exhibiting symptoms of kidney dysfunction a distinct staining pattern is observed, namely that antisera immunospecific for $\alpha_{6A}$ cytoplasmic domain (6488) reacts with glomerular cells and antisera immunospecific for 2246B cytoplasmic domain (382) reacts with the tubular epithelial cells.

These results show that antibodies immunoreactive with the cytoplasmic domain of $\alpha_{6B}$ are useful for distinguishing cell types in kidney sections, and particularly to identify distal and collecting tubular epithelial cells in patients having conditions of kidney dysfunction such as glomerular nephritis.

Although the present invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

SEQUENCE LISTINGS

SEQ ID NO 1 is the 1073 residue amino acid sequence of the human $\alpha_{6A}$ protein. The putative transmembrane region is encompassed by amino acids 1012-1037. The mature protein is cleaved from the signal sequence between amino acids 23-24. Potential sites of N-linked glycosylation are at positions 223, 284, 370, 513, 731, 748, 891, 927 and 958. Putative cation binding domains are at positions 230-238, 324-332, 386-394 and 441-449. The cytoplasmic sequence GFFKR, which is conserved in virtually all of the integrin α chains, begins at amino acid position 1040. The sequence encoded by the fragment of $\alpha_{6A}$ cDNA amplified using primers 1156/1157 is encompassed by residues 927-1073.

SEQ ID NO 1:

| 1 | | | | |
|---|---|---|---|---|
| MAAAGQLCLL | YLSAGLLSRL | GAAFNLDTRE | DNVIRKYGDP | GSLFGFSLAM |
| 51 | | | | |
| HWQLQPEDKR | LLLVGAPRGE | ALPLQRAFRT | GGLYSCDITA | RGPCTRIEFD |
| 101 | | | | |
| NDADPTSESK | EDQWMGVTVQ | SQGPGGKVVT | CAHRYEKRQH | VNTKQESRDI |
| 151 | | | | |
| FGRCYVLSQN | LRIEDDMDGG | DWSFCDGRLR | GHEKFGSCQQ | GVAATFTKDF |
| 201 | | | | |
| HYIVFGAPGT | YNWKGIVRVE | QKNNTFFDMN | IFEDGPYEVG | GETEHDESLV |
| 251 | | | | |
| PVPANSYLGF | SLDSGKGIVS | KDEITFVSGA | PRANHSGAVV | LLKRDMKSAH |

| 301 | | | | |
|---|---|---|---|---|
| LLPEHIFDGE | GLASSFGYDV | AVMDLNKDGW | QDIVIGAPQY | FDRDGEVGGA |
| 351 | | | | |
| VYVYMNQQGR | WNNVKPIRLN | GTKDSMFGIA | VKNIGDINQD | GYPDIAVGAP |
| 401 | | | | |
| YDDLGKVFIY | HGSANGINTK | PTQVLKGISP | YFGYSIAGNM | DLDRNSYPDV |
| 451 | | | | |
| AVGSLSDSVT | IFRSRPVINI | QKTITVTPNR | IDLRQKTACG | APSGICLQVK |
| 501 | | | | |
| SCFEYTANPA | GYNPSISIVG | TLEAEKERRK | SGLSSRVQFR | NQGSEPKYTQ |
| 551 | | | | |
| ELTLKRQKQK | VCMEETLWLQ | DNIRDKLRPI | PITASVEIQE | PSSRRRVNSL |
| 601 | | | | |
| PEVLPILNSD | EPKTAHIDVH | FLKEGCGDDN | VCNSNLKLEY | KFCTREGNQD |
| 651 | | | | |
| KFSYLPIQKG | VPELVLKDQK | DIALEITVTN | SPSNPRNPTK | DGDDAHEAKL |
| 701 | | | | |
| IATFPDTLTY | SAYRELRAFP | EKQLSCVANQ | NGSQADCELG | NPFKRNSNVT |
| 751 | | | | |
| FYLVLSTTEV | TFDTPYLDIN | LKLETTSNQD | NLAPITAKAK | VVIELLLSVS |
| 801 | | | | |
| GVAKPSQVYF | GGTVVGEQAM | KSEDEVGSLI | EYEFRVINLG | KPLTNLGTAT |
| 851 | | | | |
| LNIQWPKEIS | NGKWLLYLVK | VESKGLEKVT | CEPQKEINSL | NLTESHNSRK |
| 901 | | | | |
| KREITEKQID | DNRKFSLFAE | RKYQTLNCSV | NVNCVNIRCP | LRGLDSKASL |
| 951 | | | | |
| ILRSRLWNST | FLEEYSKLNY | LDILMRAFID | VTAAAENIRL | PNAGTQVRVT |
| 1001 | | | | |
| VFPSKTVAQY | SGVPWWIILV | AILAGILMLA | LLVFILWKCG | FFKRNKKDHY |
| 1051 | | | | |
| DATYHKAEIH | AQPSDKERLT | SDA | | |

SEQ ID NO 2 is the 5629 base nucleotide sequence of the human $\alpha_{6A}$ cDNA. The initiating ATG is at nucleotide position 147. The mature coding sequence begins at nucleotide position 216 and ends at position 3365. The cytoplasmic sequence GFFKR is encoded by nucleotides 3264–3278. The 130 nucleotide sequence present in SEQ ID NO 2 but deleted from SEQ ID NO 4 is encompassed by nucleotides 3261–3390. The sequence of the $\alpha_{6A}$ cDNA amplified using primers 1156/1157 is encompassed by nucleotides 2924–3455.

SEQ ID NO 2:
1
GCGCGACCGT CCCGGGGGTG GGGCCGGGCG CAGCGGCGAG AGGAGGCGAA

51
GGTGGCTGCG GTAGCAGCAG CGCGGCAGCC TCGGACCCAG CCCGGAGCGC

101
AGGGCGGCCG CTGCAGGTCC CCGCTCCCCT CCCCGTGCGT CCGCCCATGG

151
CCGCCGCCGG GCAGCTGTGC TTGCTCTACC TGTCGGCGGG GCTCCTGTCC

201
CGGCTCGGCG CAGCCTTCAA CTTGGACACT CGGGAGGACA ACGTGATCCG

251
GAAATATGGA GACCCCGGGA GCCTCTTCGG CTTCTCGCTG GCCATGCACT

301
GGCAACTGCA GCCCGAGGAC AAGCGGCTGT TGCTCGTGGG GGCCCCGCGC

351
GGAGAAGCGC TTCCACTGCA GAGAGCCTTC AGAACGGGAG GGCTGTACAG

401

-continued

```
     CTGCGACATC ACCGCCCGGG GGCCATGCAC GCGGATCGAG TTTGATAACG
451
     ATGCTGACCC CACGTCAGAA AGCAAGGAAG ATCAGTGGAT GGGGGTCACC
501
     GTCCAGAGCC AAGGTCCAGG GGGCAAGGTC GTGACATGTG CTCACCGATA
551
     TGAAAAAAGG CAGCATGTTA ATACGAAGCA GGAATCCCGA GACATCTTTG
601
     GGCGGTGTTA TGTCCTGAGT CAGAATCTCA GGATTGAAGA CGATATGGAT
651
     GGGGGAGATT GGAGCTTTTG TGATGGGCGA TTGAGAGGCC ATGAGAAATT
701
     TGGCTCTTGC CAGCAAGGTG TAGCAGCTAC TTTTACTAAA GACTTTCATT
751
     ACATTGTATT TGGAGCCCCG GGTACTTATA ACTGGAAAGG GATTGTTCGT
801
     GTAGAGCAAA AGAATAACAC TTTTTTTGAC ATGAACATCT TTGAAGATGG
851
     GCCTTATGAA GTTGGTGGAG AGACTGAGCA TGATGAAAGT CTCGTTCCTG
901
     TTCCTGCTAA CAGTTACTTA GGTTTTTCTT TGGACTCAGG GAAAGGTATT
951
     GTTTCTAAAG ATGAGATCAC TTTTGTATCT GGTGCTCCCA GAGCCAATCA
1001
     CAGTGGAGCC GTGGTTTTGC TGAAGAGAGA CATGAAGTCT GCACATCTCC
1051
     TCCCTGAGCA CATATTCGAT GGAGAAGGTC TGGCCTCTTC ATTTGGCTAT
1101
     GATGTGGCGG TGATGGACCT CAACAAGGAT GGGTGGCAAG ATATAGTTAT
1151
     TGGAGCCCCA CAGTATTTTG ATAGAGATGG AGAAGTTGGA GGTGCAGTGT
1201
     ATGTCTACAT GAACCAGCAA GGCAGATGGA ATAATGTGAA GCCAATTCGT
1251
     CTTAATGGAA CCAAAGATTC TATGTTTGGC ATTGCAGTAA AAAATATTGG
1301
     AGATATTAAT CAAGATGGCT ACCCAGATAT TGCAGTTGGA GCTCCGTATG
1351
     ATGACTTGGG AAAGGTTTTT ATCTATCATG GATCTGCAAA TGGAATAAAT
1401
     ACCAAACCAA CACAGGTTCT CAAGGGTATA TCACCTTATT TTGGATATTC
1451
     AATTGCTGGA AACATGGACC TTGATCGAAA TTCCTACCCT GATGTTGCTG
1501
     TTGGTTCCCT CTCAGATTCA GTAACTATT .TCAGATCCCG GCCTGTGATT
1551
     AATATTCAGA AAACCATCAC AGTAACTCCT AACAGAATTG ACCTCCGCCA
1601
     GAAAACAGCG TGTGGGGCGC CTAGTGGGAT ATGCCTCCAG GTTAAATCCT
1651
     GTTTTGAATA TACTGCTAAC CCCGCTGGTT ATAATCCTTC AATATCAATT
1701
     GTGGGCACAC TTGAAGCTGA AAAAGAAAGA AGAAAATCTG GCTATCCTC
1751
     AAGAGTTCAG TTTCGAAACC AAGGTTCTGA GCCCAAATAT ACTCAAGAAC
```

-continued

1801
TAACTCTGAA GAGGCAGAAA CAGAAAGTGT GCATGGAGGA AACCCTGTGG

1851
CTACAGGATA ATATCAGAGA TAAACTGCGT CCCATTCCCA TAACTGCCTC

1901
AGTGGAGATC CAAGAGCCAA GCTCTCGTAG GCGAGTGAAT TCACTTCCAG

1951
AAGTTCTTCC AATTCTGAAT TCAGATGAAC CCAAGACAGC TCATATTGAT

2001
GTTCACTTCT TAAAAGAGGG ATGTGGAGAC GACAATGTAT GTAACAGCAA

2051
CCTTAAACTA GAATATAAAT TTTGCACCCG AGAAGGAAAT CAAGACAAAT

2101
TTTCTTATTT ACCAATTCAA AAAGGTGTAC CAGAACTAGT TCTAAAAGAT

2151
CAGAAGGATA TTGCTTTAGA ATAACAGTG ACAAACAGCC CTTCCAACCC

2201
AAGGAATCCC ACAAAAGATG GCGATGACGC CCATGAGGCT AAACTGATTG

2251
CAACGTTTCC AGACACTTTA ACCTATTCTG CATATAGAGA ACTGAGGGCT

2301
TTCCCTGAGA AACAGTTGAG TTGTGTTGCC AACCAGAATG GCTCGCAAGC

2351
TGACTGTGAG CTCGGAAATC CTTTTAAAAG AAATTCAAAT GTCACTTTTT

2401
ATTTGGTTTT AAGTACAACT GAAGTCACCT TTGACACCCC ATATCTGGAT

2451
ATTAATCTGA AGTTAGAAAC AACAAGCAAT CAAGATAATT TGGCTCCAAT

2501
TACAGCTAAA GCAAAAGTGG TTATTGAACT GCTTTTATCG GTCTCGGGAG

2551
TTGCTAAACC TTCCCAGGTG TATTTTGGAG GTACAGTTGT TGGCGAGCAA

2601
GCTATGAAAT CTGAAGATGA AGTGGGAAGT TTAATAGAGT ATGAATTCAG

2651
GGTAATAAAC TTAGGTAAAC CTCTTACAAA CCTCGGCACA GCAACCTTGA

2701
ACATTCAGTG GCCAAAAGAA ATTAGCAATG GGAAATGGTT GCTTTATTTG

2751
GTGAAAGTAG AATCCAAAGG ATTGGAAAAG GTAACTTGTG AGCCACAAAA

2801
GGAGATAAAC TCCCTGAACC TAACGGAGTC TCACAACTCA GAAAGAAAC

2851
GGGAAATTAC TGAAAAACAG ATAGATGATA ACAGAAAATT TTCTTTATTT

2901
GCTGAAAGAA AATACCAGAC TCTTAACTGT AGCGTGAACG TGAACTGTGT

2951
GAACATCAGA TGCCCGCTGC GGGGCTGGA CAGCAAGGCG TCTCTTATTT

3001
TGCGCTCGAG GTTATGGAAC AGCACATTTC TAGAGGAATA TTCCAAACTG

3051
AACTACTTGG ACATTCTCAT GCGAGCCTTC ATTGATGTGA CTGCTGCTGC

3101
CGAAAATATC AGGCTGCCAA ATGCAGGCAC TCAGGTTCGA GTGACTGTGT

3151
TTCCCTCAAA GACTGTAGCT CAGTATTCGG GAGTACCTTG GTGGATCATC

```
3201
CTAGTGGCTA TTCTCGCTGG GATCTTGATG CTTGCTTTAT TAGTGTTTAT

3251
ACTATGGAAG TGTGGTTTCT TCAAGAGAAA TAAGAAAGAT CATTATGATG

3301
CCACATATCA CAAGGCTGAG ATCCATGCTC AGCCATCTGA TAAAGAGAGG

3351
CTTACTTCTG ATGCATAGTA TTGATCTACT TCTGTAATTG TGTGGATTCT

3401
TTAAACGCTC TAGGTACGAT GACAGTGTTC CCCGATACCA TGCTGTAAGG

3451
ATCCGGAAAG AAGAGCGAGA GATCAAAGAT GAAAAGTATA TTGATAACCT

3501
TGAAAAAAAA CAGTGGATCA CAAAGTGGAA CAGAAATGAA AGCTACTCAT

3551
AGCGGGGGCC TAAAAAAAAA AAAGCTTCAC AGTACCCAAA CTGCTTTTTC

3601
CAACTCAGAA ATTCAATTTG GATTTAAAAG CCTGCTCAAT CCCTGAGGAC

3651
TGATTTCAGA GTGACTACAC ACAGTACGAA CCTACAGTTT TAACTGTGGA

3701
TATTGTTACG TAGCCTAAGG CTCCTGTTTT GCACAGCCAA ATTTAAAACT

3751
GTTGGAATGG ATTTTTCTTT AACTGCCGTA ATTTAACTTT CTGGGTTGCC

3801
TTTGTTTTTG GCGTGGCTGA CTTACATCAT GTGTTGGGGA AGGGCCTGCC

3851
CAGTTGCACT CAGGTGACAT CCTCCAGATA GTGTAGCTGA GGAGGCACCT

3901
ACACTCACCT GCACTAACAG AGTGGCCGTC CTAACCTCGG GCCTGCTGCG

3951
CAGACGTCCA TCACGTTAGC TGTCCCACAT CACAAGACTA TGCCATTGGG

4001
GTAGTTGTGT TTCAACGGAA AGTGCTGTCT TAAACTAAAT GTGCAATAGA

4051
AGGTGATGTT GCCATCCTAC CGTCTTTTCC TGTTTCCTAG CTGTGTGAAT

4101
ACCTGCTCAC GTCAAATGCA TACAAGTTTC ATTCTCCCTT TCACTAAAAA

4151
CACACAGGTG CAACAGACTT GAATGCTAGT TATACTTATT TGTATATGGT

4201
ATTTATTTTT TCTTTTCTTT ACAAACCATT TTGTTATTGA CTAACAGGCC

4251
AAAGAGTCTC CAGTTTACCC TTCAGGTTGG TTTAATCAAT CAGAATTAGA

4301
ATTAGAGCAT GGGAGGGTCA TCACTATGAC CTAAATTATT TACTGCAAAA

4351
AGAAAATCTT TATAAATGTA CCAGAGAGAG TTGTTTTAAT AACTTATCTA

4401
TAAACTATAA CCTCTCCTTC ATGACAGCCT CCACCCCACA ACCCAAAAGG

4451
TTTAAGAAAT AGAATTATAA CTGTAAAGAT GTTTATTTCA GGCATTGGAT

4501
ATTTTTTACT TTAGAAGCCT GCATAATGTT TCTGGATTTA CATACTGTAA

4551
```

-continued

```
CATTCAGGAA TTCTTGGAGA AGATGGGTTT ATTCACTGAA CTCTAGTGCG
4601
GTTTACTCAC TGCTGCAAAT ACTGTATATT CAGGACTTGA AAGAAATGGT
4651
GAATGCCTAT GGAACTAGTG GATCCAAACT GATCCAGTAT AAGACTACTG
4701
AATCTGCTAC CAAAACAGTT AATCAGTGAG TCGAGTGTTC TATTTTTTGT
4751
TTTGTTTCCT CCCCTATCTG TATTCCCAAA AATTACTTTG GGGCTAATTT
4801
AACAAGAACT TTAAATTGTG TTTTAATTGT AAAAATGGCA GGGGGTGGAA
4851
TTATTACTCT ATACATTCAA CAGAGACTGA ATAGATATGA AAGCTGATTT
4901
TTTTTAATTA CCATGCTTCA CAATGTTAAG TTATATGGGG AGCAACAGCA
4951
AACAGGTGCT AATTTGTTTT GGATATAGTA TAAGCAGTGT CTGTGTTTTG
5001
AAAGAATAGA ACACAGTTTG TAGTGCCACT GTTGTTTTGG GGGGGGCTTT
5051
TTTTCTTTTT CCGGAAAATC CTTAAACCTT AAGATACTAA GGACGTTGTT
5101
TTGGTTGTAC TTGGAATTCT TAGTCACAAA ATATATTTTG TTTACAAAAA
5151
TTTCTGTAAA ACAGGTTATA ACAGTGTTTA AAGTCTCAGT TTCTTGCTTG
5201
GGGAACTTGT GTCCCTAATG TGTTAGATTG CTAGATTGCT AAGGAGCTGA
5251
TACTTGACAG TTTTTTAGAC CTGTGTTACT AAAAAAAAGA TGAATGTCGG
5301
AAAAGGGTGT TGGGAGGGTG GTCAACAAAG AAACAAAGAT GTTATGGTGT
5351
TTAGACTTAT GGTTGTTAAA AATGTCATCT CAAGTCAAGT CACTGGTCTG
5401
TTTGCATTTG ATACATTTTT GTACTAACTA GCATTGTAAA ATTATTTCAT
5451
GATTAGAAAT TACCTGTGGA TATTTGTATA AAAGTGTGAA ATAAATTTTT
5501
TATAAAAGTG TTCATTGTTT CGTAACACAG CATTGTATAT GTGAAGCAAA
5551
CTCTAAAATT ATAAATGACA ACCTGAATTA TCTATTTCAT CAAAAAAAAA
5601
AAAAAAAAAA ACTTTATGGG CACAACTGG
```

SEQ ID NO 3 is the 1091 residue amino acid sequence of the human α6B protein. The sequence of SEQ ID NO 3 is identical to SEQ ID NO 1 between amino acids 1 and 1044. The sequence encoded by the fragment of α6B cDNA amplified using primers 1156/1157 is encompassed by residue 927 through 1060.

SEQ ID NO 3:
1
MAAAGQLCLL YLSAGLLSRL GAAFNLDTRE DNVIRKYGDP GSLFGFSLAM

51
HWQLQPEDKR LLLVGAPRGE ALPLQRAFRT GGLYSCDITA RGPCTRIEFD

101
NDADPTSESK EDQWMGVTVQ SQGPGGKVVT CAHRYEKRQH VNTKQESRDI

151
FGRCYVLSQN LRIEDDMDGG DWSFCDGRLR GHEKFGSCQQ GVAATFTKDF

201
HYIVFGAPGT YNWKGIVRVE QKNNTFFDMN IFEDGPYEVG GETEHDESLV

251
PVPANSYLGF SLDSGKGIVS KDEITFVSGA PRANHSGAVV LLKRDMKSAH

301
LLPEHIFDGE GLASSFGYDV AVMDLNKDGW QDIVIGAPQY FDRDGEVGGA

351
VYVYMNQQGR WNNVKPIRLN GTKDSMFGIA VKNIGDINQD GYPDIAVGAP

401
YDDLGKVFIY HGSANGINTK PTQVLKGISP YFGYSIAGNM DLDRNSYPDV

451
AVGSLSDSVT IFRSRPVINI QKTITVTPNR IDLRQKTACG APSGICLQVK

501
SCFEYTANPA GYNPSISIVG TLEAEKERRK SGLSSRVQFR NQGSEPKYTQ

551
ELTLKRQKQK VCMEETLWLQ DNIRDKLRPI PITASVEIQE PSSRRRVNSL

601
PEVLPILNSD EPKTAHIDVH FLKEGCGDDN VCNSNLKLEY KFCTREGNQD

651
KFSYLPIQKG VPELVLKDQK DIALEITVTN SPSNPRNPTK DGDDAHEAKL

701
IATFPDTLTY SAYRELRAFP EKQLSCVANQ NGSQADCELG NPFKRNSNVT

751
FYLVLSTTEV TFDTPYLDIN LKLETTSNQD NLAPITAKAK VVIELLLSVS

801
GVAKPSQVYF GGTVVGEQAM KSEDEVGSLI EYEFRVINLG KPLTNLGTAT

851
LNIQWPKEIS NGKWLLYLVK VESKGLEKVT CEPQKEINSL NLTESHNSRK

901
KREITEKQID DNRKFSLFAE RKYQTLNCSV NVNCVNIRCP LRGLDSKASL

951
ILRSRLWNST FLEEYSKLNY LDILMRAFID VTAAAENIRL PNAGTQVRVT

1001
VFPSKTVAQY SGVPWWIILV AILAGILMLA LLVFILWKCG FFKRSRYDDS

1051
VPRYHAVRIR KEEREIKDEK YIDNLEKKQW ITKWNRNESY S

SEQ ID NO 4 is the 5499 base nucleotide sequence of the human $\alpha_{6B}$ cDNA. The sequence of SEQ ID NO 4 is identical to SEQ ID NO 2 between nucleotides 1 and 3260. Nucleotides 3261–5499 of SEQ ID NO 4 are identical to nucleotides 3391–5629 of SEQ ID NO 2. SEQ ID NO 4 has a 130 nucleotide deletion in relation to SEQ ID NO 2. The sequence of the $\alpha_{6B}$ cDNA amplified using primers 1156/1157 is encompassed by nucleotides 2924–3325.

SEQ ID NO 4:
1
GCGCGACCGT CCCGGGGGTG GGGCCGGGCG CAGCGGCGAG AGGAGGCGAA

51
GGTGGCTGCG GTAGCAGCAG CGCGGCAGCC TCGGACCCAG CCCGGAGCGC

101
AGGGCGGCCG CTGCAGGTCC CCGCTCCCCT CCCCGTGCGT CCGCCCATGG

151
CCGCCGCCGG GCAGCTGTGC TTGCTCTACC TGTCGGCGGG GCTCCTGTCC

201
CGGCTCGGCG CAGCCTTCAA CTTGGACACT CGGGAGGACA ACGTGATCCG

251
GAAATATGGA GACCCCGGGA GCCTCTTCGG CTTCTCGCTG GCCATGCACT

301

-continued

```
     GGCAACTGCA GCCCGAGGAC AAGCGGCTGT TGCTCGTGGG GGCCCCGCGC
351
     GGAGAAGCGC TTCCACTGCA GAGAGCCTTC AGAACGGGAG GGCTGTACAG
401
     CTGCGACATC ACCGCCCGGG GGCCATGCAC GCGGATCGAG TTTGATAACG
451
     ATGCTGACCC CACGTCAGAA AGCAAGGAAG ATCAGTGGAT GGGGGTCACC
501
     GTCCAGAGCC AAGGTCCAGG GGGCAAGGTC GTGACATGTG CTCACCGATA
551
     TGAAAAAAGG CAGCATGTTA ATACGAAGCA GGAATCCCGA GACATCTTTG
601
     GGCGGTGTTA TGTCCTGAGT CAGAATCTCA GGATTGAAGA CGATATGGAT
651
     GGGGGAGATT GGAGCTTTTG TGATGGGCGA TTGAGAGGCC ATGAGAAATT
701
     TGGCTCTTGC CAGCAAGGTG TAGCAGCTAC TTTTACTAAA GACTTTCATT
751
     ACATTGTATT TGGAGCCCCG GGTACTTATA ACTGGAAAGG GATTGTTCGT
801
     GTAGAGCAAA AGAATAACAC TTTTTTTGAC ATGAACATCT TTGAAGATGG
851
     GCCTTATGAA GTTGGTGGAG AGACTGAGCA TGATGAAAGT CTCGTTCCTG
901
     TTCCTGCTAA CAGTTACTTA GGTTTTTCTT TGGACTCAGG GAAAGGTATT
951
     GTTTCTAAAG ATGAGATCAC TTTTGTATCT GGTGCTCCCA GAGCCAATCA
1001
     CAGTGGAGCC GTGGTTTTGC TGAAGAGAGA CATGAAGTCT GCACATCTCC
1051
     TCCCTGAGCA CATATTCGAT GGAGAAGGTC TGGCCTCTTC ATTTGGCTAT
1101
     GATGTGGCGG TGATGGACCT CAACAAGGAT GGGTGGCAAG ATATAGTTAT
1151
     TGGAGCCCCA CAGTATTTTG ATAGAGATGG AGAAGTTGGA GGTGCAGTGT
1201
     ATGTCTACAT GAACCAGCAA GGCAGATGGA ATAATGTGAA GCCAATTCGT
1251
     CTTAATGGAA CCAAAGATTC TATGTTTGGC ATTGCAGTAA AAAATATTGG
1301
     AGATATTAAT CAAGATGGCT ACCCAGATAT TGCAGTTGGA GCTCCGTATG
1351
     ATGACTTGGG AAAGGTTTTT ATCTATCATG GATCTGCAAA TGGAATAAAT
1401
     ACCAAACCAA CACAGGTTCT CAAGGGTATA TCACCTTATT TTGGATATTC
1451
     AATTGCTGGA ACATGGACC TTGATCGAAA TTCCTACCCT GATGTTGCTG
1501
     TTGGTTCCCT CTCAGATTCA GTAACTATTT TCAGATCCCG GCCTGTGATT
1551
     AATATTCAGA AAACCATCAC AGTAACTCCT AACAGAATTG ACCTCCGCCA
1601
     GAAAACAGCG TGTGGGCGC CTAGTGGGAT ATGCCTCCAG GTTAAATCCT
1651
     GTTTTGAATA TACTGCTAAC CCCGCTGGTT ATAATCCTTC AATATCAATT
```

-continued

1701
GTGGGCACAC TTGAAGCTGA AAAAGAAAGA AGAAAATCTG GGCTATCCTC

1751
AAGAGTTCAG TTTCGAAACC AAGGTTCTGA GCCCAAATAT ACTCAAGAAC

1801
TAACTCTGAA GAGGCAGAAA CAGAAAGTGT GCATGGAGGA AACCCTGTGG

1851
CTACAGGATA ATATCAGAGA TAAACTGCGT CCCATTCCCA TAACTGCCTC

1901
AGTGGAGATC CAAGAGCCAA GCTCTCGTAG GCGAGTGAAT TCACTTCCAG

1951
AAGTTCTTCC AATTCTGAAT TCAGATGAAC CCAAGACAGC TCATATTGAT

2001
GTTCACTTCT TAAAAGAGGG ATGTGGAGAC GACAATGTAT GTAACAGCAA

2051
CCTTAAACTA GAATATAAAT TTTGCACCCG AGAAGGAAAT CAAGACAAAT

2101
TTTCTTATTT ACCAATTCAA AAAGGTGTAC CAGAACTAGT TCTAAAAGAT

2151
CAGAAGGATA TTGCTTTAGA ATAACAGTG ACAAACAGCC CTTCCAACCC

2201
AAGGAATCCC ACAAAAGATG GCGATGACGC CCATGAGGCT AAACTGATTG

2251
CAACGTTTCC AGACACTTTA ACCTATTCTG CATATAGAGA ACTGAGGGCT

2301
TTCCCTGAGA AACAGTTGAG TTGTGTTGCC AACCAGAATG GCTCGCAAGC

2351
TGACTGTGAG CTCGGAAATC CTTTTAAAAG AAATTCAAAT GTCACTTTTT

2401
ATTTGGTTTT AAGTACAACT GAAGTCACCT TTGACACCCC ATATCTGGAT

2451
ATTAATCTGA AGTTAGAAAC AACAAGCAAT CAAGATAATT TGGCTCCAAT

2501
TACAGCTAAA GCAAAAGTGG TTATTGAACT GCTTTTATCG GTCTCGGGAG

2551
TTGCTAAACC TTCCCAGGTG TATTTTGGAG GTACAGTTGT TGGCGAGCAA

2601
GCTATGAAAT CTGAAGATGA AGTGGGAAGT TTAATAGAGT ATGAATTCAG

2651
GGTAATAAAC TTAGGTAAAC CTCTTACAAA CCTCGGCACA GCAACCTTGA

2701
ACATTCAGTG GCCAAAAGAA ATTAGCAATG GGAAATGGTT GCTTTATTTG

2751
GTGAAAGTAG AATCCAAAGG ATTGGAAAAG GTAACTTGTG AGCCACAAAA

2801
GGAGATAAAC TCCCTGAACC TAACGGAGTC TCACAACTCA AGAAAGAAAC

2851
GGGAAATTAC TGAAAAACAG ATAGATGATA ACAGAAAATT TTCTTTATTT

2901
GCTGAAAGAA AATACCAGAC TCTTAACTGT AGCGTGAACG TGAACTGTGT

2951
GAACATCAGA TGCCCGCTGC GGGGGCTGGA CAGCAAGGCG TCTCTTATTT

3001
TGCGCTCGAG GTTATGGAAC AGCACATTTC TAGAGGAATA TTCCAAACTG

3051
AACTACTTGG ACATTCTCAT GCGAGCCTTC ATTGATGTGA CTGCTGCTGC

```
3101
CGAAAATATC AGGCTGCCAA ATGCAGGCAC TCAGGTTCGA GTGACTGTGT

3151
TTCCCTCAAA GACTGTAGCT CAGTATTCGG GAGTACCTTG GTGGATCATC

3201
CTAGTGGCTA TTCTCGCTGG GATCTTGATG CTTGCTTTAT TAGTGTTTAT

3251
ACTATGGAAG TGTGGATTCT TTAAACGCTC TAGGTACGAT GACAGTGTTC

3301
CCCGATACCA TGCTGTAAGG ATCCGGAAAG AAGAGCGAGA GATCAAAGAT

3351
GAAAAGTATA TTGATAACCT TGAAAAAAAA CAGTGGATCA CAAAGTGGAA

3401
CAGAAATGAA AGCTACTCAT AGCGGGGGCC TAAAAAAAAA AAAGCTTCAC

3451
AGTACCCAAA CTGCTTTTTC CAACTCAGAA ATTCAATTTG GATTTAAAAG

3501
CCTGCTCAAT CCCTGAGGAC TGATTTCAGA GTGACTACAC ACAGTACGAA

3551
CCTACAGTTT TAACTGTGGA TATTGTTACG TAGCCTAAGG CTCCTGTTTT

3601
GCACAGCCAA ATTTAAAACT GTTGGAATGG ATTTTTCTTT AACTGCCGTA

3651
ATTTAACTTT CTGGGTTGCC TTTGTTTTTG GCGTGGCTGA CTTACATCAT

3701
GTGTTGGGGA AGGGCCTGCC CAGTTGCACT CAGGTGACAT CCTCCAGATA

3751
GTGTAGCTGA GGAGGCACCT ACACTCACCT GCACTAACAG AGTGGCCGTC

3801
CTAACCTCGG GCCTGCTGCG CAGACGTCCA TCACGTTAGC TGTCCCACAT

3851
CACAAGACTA TGCCATTGGG GTAGTTGTGT TTCAACGGAA AGTGCTGTCT

3901
TAAACTAAAT GTGCAATAGA AGGTGATGTT GCCATCCTAC CGTCTTTTCC

3951
TGTTTCCTAG CTGTGTGAAT ACCTGCTCAC GTCAAATGCA TACAAGTTTC

4001
ATTCTCCCTT TCACTAAAAA CACACAGGTG CAACAGACTT GAATGCTAGT

4051
TATACTTATT TGTATATGGT ATTTATTTTT TCTTTTCTTT ACAAACCATT

4101
TTGTTATTGA CTAACAGGCC AAAGAGTCTC CAGTTTACCC TTCAGGTTGG

4151
TTTAATCAAT CAGAATTAGA ATTAGAGCAT GGGAGGGTCA TCACTATGAC

4201
CTAAATTATT TACTGCAAAA AGAAAATCTT TATAAATGTA CCAGAGAGAG

4251
TTGTTTTAAT AACTTATCTA TAAACTATAA CCTCTCCTTC ATGACAGCCT

4301
CCACCCCACA ACCCAAAAGG TTTAAGAAAT AGAATTATAA CTGTAAAGAT

4351
GTTTATTTCA GGCATTGGAT ATTTTTTACT TTAGAAGCCT GCATAATGTT

4401
TCTGGATTTA CATACTGTAA CATTCAGGAA TTCTTGGAGA AGATGGGTTT

4451
```

-continued

```
     ATTCACTGAA CTCTAGTGCG GTTTACTCAC TGCTGCAAAT ACTGTATATT
4501
     CAGGACTTGA AAGAAATGGT GAATGCCTAT GGAACTAGTG GATCCAAACT
4551
     GATCCAGTAT AAGACTACTG AATCTGCTAC CAAAACAGTT AATCAGTGAG
4601
     TCGAGTGTTC TATTTTTTGT TTTGTTTCCT CCCCTATCTG TATTCCCAAA
4651
     AATTACTTTG GGGCTAATTT AACAAGAACT TTAAATTGTG TTTTAATTGT
4701
     AAAAATGGCA GGGGGTGGAA TTATTACTCT ATACATTCAA CAGAGACTGA
4751
     ATAGATATGA AAGCTGATTT TTTTTAATTA CCATGCTTCA CAATGTTAAG
4801
     TTATATGGGG AGCAACAGCA AACAGGTGCT AATTTGTTTT GGATATAGTA
4851
     TAAGCAGTGT CTGTGTTTTG AAAGAATAGA ACACAGTTTG TAGTGCCACT
4901
     GTTGTTTTGG GGGGGGCTTT TTTTCTTTTT CCGGAAAATC CTTAAACCTT
4951
     AAGATACTAA GGACGTTGTT TTGGTTGTAC TTGGAATTCT TAGTCACAAA
5001
     ATATATTTTG TTTACAAAAA TTTCTGTAAA ACAGGTTATA ACAGTGTTTA
5051
     AAGTCTCAGT TTCTTGCTTG GGGAACTTGT GTCCCTAATG TGTTAGATTG
5101
     CTAGATTGCT AAGGAGCTGA TACTTGACAG TTTTTTAGAC CTGTGTTACT
5151
     AAAAAAAAGA TGAATGTCGG AAAAGGGTGT TGGGAGGGTG GTCAACAAAG
5201
     AAACAAAGAT GTTATGGTGT TTAGACTTAT GGTTGTTAAA AATGTCATCT
5251
     CAAGTCAAGT CACTGGTCTG TTTGCATTTG ATACATTTTT GTACTAACTA
5301
     GCATTGTAAA ATTATTTCAT GATTAGAAAT TACCTGTGGA TATTTGTATA
5351
     AAAGTGTGAA ATAAATTTTT TATAAAAGTG TTCATTGTTT CGTAACACAG
5401
     CATTGTATAT GTGAAGCAAA CTCTAAAATT ATAAATGACA ACCTGAATTA
5451
     TCTATTTCAT CAAAAAAAAA AAAAAAAAAA ACTTTATGGG CACAACTGG
```

SEQ ID NO 5 is the 141 amino acid sequence predicted from the nucleic acid product which results from amplification of the mouse $\alpha_{6B}$ cDNA with primers 1157/1156. The putative transmembrane domain begins at amino acid 88 and continues through amino acid 113. SEQ ID NO 5 is identical to SEQ ID NO 7 at amino acid position 1 through 120; the two sequences diverge at amino acid 121.

```
SEQ ID NO 5:
1
TLNCSVNVRC  VNIRCPLRGL  DSKASLVLRS  RLWNSTFLEE  YSKLNYLDIL

51
LRASIDVTAA  AQNIKLLTAG  TQVRVTVFPS  KTVAQYSGVA  WWIILLAVLA

101
GILMLALLVF  LLWKCGFFKR  SRYDDSIPRY  HAVRIRKEERE
```

SEQ ID NO 6 is the 426 base nucleotide sequence corresponding to the mouse $\alpha_{6B}$ amino acid sequence in SEQ ID NO 5. The putative transmembrane region is encoded by nucleotides 262 through 337. SEQ ID NO 6 is identical to SEQ ID NO 8 except for 130 nucleotides present in SEQ ID NO 8 but deleted between nucleotides 342 and 343 of SEQ ID NO 6.

SEQ ID NO 8 is the 556 base nucleotide sequence corresponding to the mouse α6A amino acid sequence in SEQ ID NO 7, plus the first 109 nucleotides in the 3' noncoding region. SEQ ID NO 8 is identical to SEQ ID NO 6 except it has a 130 base insertion (nucleotides 342–472 of SEQ ID NO 8) between nucleotides 352 and 353 of SEQ ID NO 6.

SEQ ID NO 6:
```
1
GACTCTTAAC TGTAGCGTGA ACGTGAGGTG TGTGAACATC AGGTGCCCAC

51
TGCGAGGGCT GGACAGCAAG GCCTCTCTCG TTCTTCGTTC CAGGTTGTGG

101
AACAGCACAT TTCTAGAGGA ATATTCCAAA CTGAACTACT TGGACATTCT

151
CCTGAGGGCT TCCATAGATG TCACCGCTGC TGCTCAGAAT ATCAAGCTCC

201
TCACCGCCGG CACTCAGGTT CGAGTGACGG TGTTTCCCTC AAAGACTGTA

251
GCTCAGTATT CAGGAGTAGC TTGGTGGATC ATCCTCCTGG CTGTTCTTGC

301
CGGGATTCTG ATGCTGGCTC TATTAGTGTT TTTACTGTGG AAGTGTGGAT

351
TCTTTAAGCG CTCTAGGTAC GATGACAGCA TTCCCCGATA CCATGCGGTG

401
CGGATCCGGA AAGAAGAGCG AGAGAT
```

SEQ ID NO 7 is the 149 amino acid sequence predicted from the product which results from amplification of the mouse α6A cDNA with primers 1157/1156. SEQ ID NO 7 is identical to SEQ ID NO 5 at amino acid positions 1 through 120; the sequences diverge at amino acid 121.

SEQ ID NO 7:
```
1
TLNCSVNVRC VNIRCPLRGL DSKASLVLRS RLWNSTFLEE YSKLNYLDIL

51
LRASIDVTAA AQNIKLLTAG TQVRVTVFPS KTVAQYSGVA WWIILLAVLA

101
GILMLALLVF LLWKCGFFKR NKKDHYDATY HKAEIHTQPS DKERLTSDA
```

SEQ ID NO 8:
```
1
GACTCTTAAC TGTAGCGTGA ACGTGAGGTG TGTGAACATC AGGTGCCCAC

51
TGCGAGGGCTG GACAGCAAG GCCTCTCTCG TTCTTCGTTC CAGGTTGTGG

101
AACAGCACAT TTCTAGAGGA ATATTCCAAA CTGAACTACT TGGACATTCT

151
CCTGAGGGCT TCCATAGATG TCACCGCTGC TGCTCAGAAT ATCAAGCTCC

201
TCACCGCCGG CACTCAGGTT CGAGTGACGG TGTTTCCCTC AAAGACTGTA

251
GCTCAGTATT CAGGAGTAGC TTGGTGGATC ATCCTCCTGG CTGTTCTTGC

301
CGGGATTCTG ATGCTGGCTC TATTAGTGTT TTTACTGTGG AAGTGTGGCT

351
TCTTCAAGAG AAATAAGAAA GATCATTACG ATGCCACCTA TCACAAGGCT

401
GAGATCCATA CTCAGCCGTC TGATAAAGAG AGGCTTACTT CCGATGCATA

451
GTATTGATCT ACTTCCATAA TTGTGTGGAT TCTTTAAGCG CTCTAGGTAC
```

```
501
GATGACAGCA   TTCCCCGATA   CCATGCGGTG   CGGATCCGGA   AAGAAGAGCG

551
AGAGAT
```

SEQ ID NO 9 is the 153 amino acid sequence predicted from the product which results from amplification of the mouse $\alpha_{3B}$ cDNA with primers 2032/2033. The cytoplasmic sequence CDFFK begins at amino acid position 108.

```
SEQ ID NO 9:
1
ARCVWLECPL   PDTSNITNVT   VKARVWNSTF   IEDYKDFDRV   RVDGWATLFL

51
RTSIPTINME   NKTTCFSVNI   DSKLLEELPA   EIELWLVLVA   VGAGLLLLGL

101
IIILLWKCDF   FKPTRYYRIM   PKYHAVRIRE   EDRYPPPGST   LPTKKHWVTS

151
WQI
```

SEQ ID NO 10 is the 463 base nucleotide sequence corresponding to the mouse $\alpha_{3B}$ amino acid sequence in SEQ ID NO 9. The cytoplasmic sequence CDFFK is encoded by nucleotides 324–338.

```
SEQ ID NO 10:
1
GTGCCCGCTG   TGTGTGGCTG   GAGTGCCCCC   TTCCAGACAC   CTCCAACATT

51
ACCAATGTGA   CCGTGAAAGC   ACGGGTGTGG   AACAGCACCT   TCATTGAGGA

101
CTACAAAGAC   TTTGACAGAG   TCAGGGTAGA   TGGCTGGGCT   ACCCTGTTCC

151
TGAGAACCAG   CATCCCTACC   ATCAACATGG   AGAACAAGAC   CACATGTTTC

201
TCTGTGAACA   TTGACTCAAA   GCTGTTGGAG   GAGCTGCCCG   CTGAGATTGA

251
GCTGTGGTTG   GTGCTTGTGG   CCGTGGGTGC   TGGGTTGCTG   CTGCTGGGGC

301
TCATCATCAT   CCTCTTGTGG   AAGTGTGACT   TCTTTAAGCC   GACCCGCTAC

351
TACCGGATTA   TGCCCAAGTA   CCATGCAGTG   CGTATCCGGG   AGGAGGACCG

401
CTACCCACCT   CCAGGGAGCA   CGCTACCCAC   CAAGAAGCAC   TGGGTCACCA

451
GCTGGCAGAT   TCG
```

SEQ ID NO 11 is the outer 5' PCR primer 1157, corresponding to bp 2918–2937 of the $\alpha_{6A}$ cDNA sequence of Sequence ID NO 2.

SEQ ID NO 11:
5' - GACTCTTAAC TGTAGCGTGA - 3'

SEQ ID NO 12 is the outer 3' PCR primer 1156, corresponding to the complement of bp 3454–3473 of the $\alpha_{6A}$ cDNA sequence of SEQ ID NO 2.

SEQ ID NO 12:
5' - ATCTCTCGCT CTTCTTTCCG - 3'

SEQ ID NO 13 is the inner 5' nested PCR primer 1681, corresponding to bp 2942–2960 of the $\alpha_{6A}$ cDNA sequence of SEQ ID NO 2.

SEQ ID NO 13:
5' - GAACTGTGTG AACATCAGA - 3'

SEQ ID NO 14 is the inner 3' nested PCR primer 2002, corresponding to the complement of bp 3433–3452 of the $\alpha_{6A}$ cDNA sequence of SEQ ID NO 2.

SEQ ID NO 14:
5' - ATCCTTACAG CATGGTATCG - 3'

SEQ ID NO 15 is the 5' PCR primer 2032, corresponding to the hamster $\alpha_{3,4}$ cDNA sequence of Tsuji et al., *J. Biol. Chem.*, 265:7016-7021 (1990).

SEQ ID NO 15:
5' - AAGCCAAATC TGAGACTGTG - 3'

SEQ ID NO 16 is the 3' PCR primer 2033, corresponding to the hamster $\alpha_{3,4}$ cDNA sequence of Tsuji et al., *J. Biol. Chem.*, 265:7016-7021 (1990).

SEQ ID NO 16:
5' - GTAGTATCGG TCCCGAATCT - 3'

What is claimed is:

1. An antibody molecule that immunoreacts with a polypeptide consisting of an amino acid residue sequence shown in SEQ ID NO 3 from residue 1068-1091.

2. The antibody molecule of claim 1 wherein said antibody molecule is a monoclonal antibody molecule.

3. An antibody molecule that immunoreacts with a polypeptide consisting of an amino acid residue sequence shown in SEQ ID NO 3 from residue 1045 to residue 1091.

4. The antibody molecule of claim 3 wherein said antibody molecule is a monoclonal antibody molecule.

5. An antibody molecule that immunoreacts with a polypeptide consisting of an amino acid residue sequence shown in SEQ ID NO 5 from residue 121 to residue 141.

6. The antibody molecule of claim 5 wherein said antibody molecule is a monoclonal antibody molecule.

7. An antibody molecule that immunoreacts with a polypeptide consisting of an amino acid residue sequence shown in SEQ ID NO 9 from residue 113 to residue 153.

8. The antibody molecule of claim 7 wherein said antibody molecule is a monoclonal antibody molecule.

9. A method for detecting the presence of antigen having the cytoplasmic domain of $\alpha_{6B}$ in a body sample comprising the steps of:

a) admixing the body sample with a composition containing antibody molecules that immunoreact with the $\alpha_{6B}$ protein and with a polypeptide consisting essentially of an amino acid residue sequence shown in SEQ ID NO 3 from residue 1045 to residue 1091 to form an immunoreaction admixture;

b) maintaining said immunoreaction admixture under immunoreaction conditions for a time period sufficient for said antibody molecules to immunoreact with any $\alpha_{6B}$ present in said body sample and form an immunoreaction complex; and c) detecting the presence of any immunoreaction complex formed in step (b) and thereby detecting the presence of said antigen in said body sample.

10. An isolated polypeptide comprising the $\alpha_{6B}$ cytoplasmic domain sequence which consists essentially of an amino acid residue sequence shown in SEQ ID NO 5 from residue 121 to residue 141.

11. An isolated polypeptide that comprising the $\alpha_{3B}$ cytoplasmic domain sequence which consists essentially of an amino acid residue sequence shown in SEQ ID NO 9 from residue 113 to residue 153.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 1073 amino acids
( B ) TYPE: amino acid
( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
( A ) ORGANISM: Homo sapiens ( i x ) FEATURE:
( A ) NAME/KEY: Domain
( B ) LOCATION: 1012..1037
( D ) OTHER INFORMATION: /label=TRANSMEMBRANE
/ note="The putative transmembrane region is
encompassed by amino acids 1012-1037."

( i x ) FEATURE:
( A ) NAME/KEY: Cleavage-site
( B ) LOCATION: (23 24)
( D ) OTHER INFORMATION: /note="The mature protein is
cleaved from the signal sequence between amino
acids 23- 24."

( i x ) FEATURE:
( A ) NAME/KEY: Modified-site
( B ) LOCATION: 223
( D ) OTHER INFORMATION: /label=GLYCOSYLATION
/ note="Potential site of N-linked glycosylation."

( i x ) FEATURE:
( A ) NAME/KEY: Modified-site
( B ) LOCATION: 284
( D ) OTHER INFORMATION: /label=GLYCOSYLATION
/ note="Potential site of N-linked glycosylation."

( i x ) FEATURE:
( A ) NAME/KEY: Modified-site
( B ) LOCATION: 370
( D ) OTHER INFORMATION: /label=GLYCOSYLATION
/ note="Potential site of N-linked glycosylation."

( i x ) FEATURE:
( A ) NAME/KEY: Modified-site
( B ) LOCATION: 513
( D ) OTHER INFORMATION: /label=GLYCOSYLATION
/ note="Potential site of N-linked glycosylation."

( i x ) FEATURE:
( A ) NAME/KEY: Modified-site
( B ) LOCATION: 731
( D ) OTHER INFORMATION: /label=GLYCOSYLATION
/ note="Potential site of N-linked glycosylation."

( i x ) FEATURE:
( A ) NAME/KEY: Modified-site
( B ) LOCATION: 748
( D ) OTHER INFORMATION: /label=GLYCOSYLATION
/ note="Potential site of N-linked glycosylation."

( i x ) FEATURE:
    ( A ) NAME/KEY: Modified-site
    ( B ) LOCATION: 891
    ( D ) OTHER INFORMATION: /label=GLYCOSYLATION
        / note="Potential site of N-linked glycosylation."

( i x ) FEATURE:
    ( A ) NAME/KEY: Modified-site
    ( B ) LOCATION: 927
    ( D ) OTHER INFORMATION: /label=GLYCOSYLATION
        / note="Potential site of N-linked glycosylation."

( i x ) FEATURE:
    ( A ) NAME/KEY: Modified-site
    ( B ) LOCATION: 958
    ( D ) OTHER INFORMATION: /label=GLYCOSYLATION
        / note="Potential site of N-linked glycosylation."

( i x ) FEATURE:
    ( A ) NAME/KEY: Binding-site
    ( B ) LOCATION: 230..238
    ( D ) OTHER INFORMATION: /note="Represents a putative
        cation binding domain."

( i x ) FEATURE:
    ( A ) NAME/KEY: Binding-site
    ( B ) LOCATION: 324..332
    ( D ) OTHER INFORMATION: /note="Represents a putative
        cation binding domain."

( i x ) FEATURE:
    ( A ) NAME/KEY: Binding-site
    ( B ) LOCATION: 386..394
    ( D ) OTHER INFORMATION: /note="Represents a putative
        cation binding domain."

( i x ) FEATURE:
    ( A ) NAME/KEY: Binding-site
    ( B ) LOCATION: 441..449
    ( D ) OTHER INFORMATION: /note="Represents a putative
        cation binding domain."

( i x ) FEATURE:
    ( A ) NAME/KEY: Domain
    ( B ) LOCATION: 1040..1044
    ( D ) OTHER INFORMATION: /label=CYTOPLASMIC
        / note="The cytoplasmic sequence, which is
        conserved in virtually all of the integrin ALPHA
        chains."

( i x ) FEATURE:
    ( A ) NAME/KEY: Region
    ( B ) LOCATION: 927..1073
    ( D ) OTHER INFORMATION: /note="The sequence encoded by the
        fragment of ALPHA 6A cDNA amplified using primers
        1156/1157."

( x i ) SEQUENCE DESCRIPTION: SEQ ID NO:1:

```
Met Ala Ala Ala Gly Gln Leu Cys Leu Leu Tyr Leu Ser Ala Gly Leu
 1               5                  10                  15

Leu Ser Arg Leu Gly Ala Ala Phe Asn Leu Asp Thr Arg Glu Asp Asn
            20                  25                  30

Val Ile Arg Lys Tyr Gly Asp Pro Gly Ser Leu Phe Gly Phe Ser Leu
        35                  40                  45

Ala Met His Trp Gln Leu Gln Pro Glu Asp Lys Arg Leu Leu Leu Val
        50                  55                  60

Gly Ala Pro Arg Gly Glu Ala Leu Pro Leu Gln Arg Ala Phe Arg Thr
65                  70                  75                  80

Gly Gly Leu Tyr Ser Cys Asp Ile Thr Ala Arg Gly Pro Cys Thr Arg
                85                  90                  95

Ile Glu Phe Asp Asn Asp Ala Asp Pro Thr Ser Glu Ser Lys Glu Asp
                100                 105                 110

Gln Trp Met Gly Val Thr Val Gln Ser Gln Gly Pro Gly Gly Lys Val
```

|     |     |     |     |     | 115 |     |     |     | 120 |     |     |     |     | 125 |
| --- | --- | --- | --- | --- | --- | --- | --- | --- | --- | --- | --- | --- | --- | --- |

Val Thr Cys Ala His Arg Tyr Glu Lys Arg Gln His Val Asn Thr Lys
130                135              140

Gln Glu Ser Arg Asp Ile Phe Gly Arg Cys Tyr Val Leu Ser Gln Asn
145              150              155                   160

Leu Arg Ile Glu Asp Met Asp Gly Asp Trp Ser Phe Cys Asp
                165              170                  175

Gly Arg Leu Arg Gly His Glu Lys Phe Gly Ser Cys Gln Gln Gly Val
            180              185                   190

Ala Ala Thr Phe Thr Lys Asp Phe His Tyr Ile Val Phe Gly Ala Pro
        195              200              205

Gly Thr Tyr Asn Trp Lys Gly Ile Val Arg Val Glu Gln Lys Asn Asn
    210              215              220

Thr Phe Phe Asp Met Asn Ile Phe Glu Asp Gly Pro Tyr Glu Val Gly
225              230              235                        240

Gly Glu Thr Glu His Asp Glu Ser Leu Val Pro Val Pro Ala Asn Ser
                245              250              255

Tyr Leu Gly Phe Ser Leu Asp Ser Gly Lys Gly Ile Val Ser Lys Asp
            260              265              270

Glu Ile Thr Phe Val Ser Gly Ala Pro Arg Ala Asn His Ser Gly Ala
        275              280              285

Val Val Leu Leu Lys Arg Asp Met Lys Ser Ala His Leu Leu Pro Glu
290                  295              300

His Ile Phe Asp Gly Glu Gly Leu Ala Ser Ser Phe Gly Tyr Asp Val
305              310              315                        320

Ala Val Met Asp Leu Asn Lys Asp Gly Trp Gln Asp Ile Val Ile Gly
                325              330              335

Ala Pro Gln Tyr Phe Asp Arg Asp Gly Glu Val Gly Gly Ala Val Tyr
            340              345              350

Val Tyr Met Asn Gln Gln Gly Arg Trp Asn Asn Val Lys Pro Ile Arg
        355              360              365

Leu Asn Gly Thr Lys Asp Ser Met Phe Gly Ile Ala Val Lys Asn Ile
370              375              380

Gly Asp Ile Asn Gln Asp Gly Tyr Pro Asp Ile Ala Val Gly Ala Pro
385              390              395                        400

Tyr Asp Asp Leu Gly Lys Val Phe Ile Tyr His Gly Ser Ala Asn Gly
            405              410              415

Ile Asn Thr Lys Pro Thr Gln Val Leu Lys Gly Ile Ser Pro Tyr Phe
        420              425              430

Gly Tyr Ser Ile Ala Gly Asn Met Asp Leu Asp Arg Asn Ser Tyr Pro
        435              440              445

Asp Val Ala Val Gly Ser Leu Ser Asp Ser Val Thr Ile Phe Arg Ser
450              455              460

Arg Pro Val Ile Asn Ile Gln Lys Thr Ile Thr Val Thr Pro Asn Arg
465              470              475                        480

Ile Asp Leu Arg Gln Lys Thr Ala Cys Gly Ala Pro Ser Gly Ile Cys
            485              490              495

Leu Gln Val Lys Ser Cys Phe Glu Tyr Thr Ala Asn Pro Ala Gly Tyr
            500              505              510

Asn Pro Ser Ile Ser Ile Val Gly Thr Leu Glu Ala Glu Lys Glu Arg
        515              520              525

Arg Lys Ser Gly Leu Ser Ser Arg Val Gln Phe Arg Asn Gln Gly Ser
    530              535              540

Glu Pro Lys Tyr Thr Gln Glu Leu Thr Leu Lys Arg Gln Lys Gln Lys
545              550              555                        560

-continued

| | | | | | | | | | | | | | | |
|---|---|---|---|---|---|---|---|---|---|---|---|---|---|---|
|Val|Cys|Met|Glu|Glu 565|Thr|Leu|Trp|Leu 570|Gln|Asp|Asn|Ile|Arg 575|Asp|Lys|
|Leu|Arg|Pro|Ile 580|Pro|Ile|Thr|Ala|Ser 585|Val|Glu|Ile|Gln 590|Glu|Pro|Ser|
|Ser|Arg|Arg 595|Arg|Val|Asn|Ser|Leu 600|Pro|Glu|Val|Leu|Pro 605|Ile|Leu|Asn|
|Ser|Asp 610|Glu|Pro|Lys|Thr|Ala 615|His|Ile|Asp|Val|His 620|Phe|Leu|Lys|Glu|
|Gly 625|Cys|Gly|Asp|Asp|Asn 630|Val|Cys|Asn|Ser|Asn 635|Leu|Lys|Leu|Glu|Tyr 640|
|Lys|Phe|Cys|Thr|Arg 645|Glu|Gly|Asn|Gln 650|Asp|Lys|Phe|Ser|Tyr|Leu 655|Pro|
|Ile|Gln|Lys|Gly 660|Val|Pro|Glu|Leu|Val 665|Leu|Lys|Asp|Gln|Lys 670|Asp|Ile|
|Ala|Leu|Glu 675|Ile|Thr|Val|Thr|Asn 680|Ser|Pro|Ser|Asn|Pro 685|Arg|Asn|Pro|
|Thr|Lys 690|Asp|Gly|Asp|Asp|Ala 695|His|Glu|Ala|Lys|Leu 700|Ile|Ala|Thr|Phe|
|Pro 705|Asp|Thr|Leu|Thr|Tyr 710|Ser|Ala|Tyr|Arg|Glu 715|Leu|Arg|Ala|Phe|Pro 720|
|Glu|Lys|Gln|Leu|Ser 725|Cys|Val|Ala|Asn|Gln 730|Asn|Gly|Ser|Gln|Ala 735|Asp|
|Cys|Glu|Leu|Gly 740|Asn|Pro|Phe|Lys|Arg 745|Asn|Ser|Asn|Val|Thr 750|Phe|Tyr|
|Leu|Val|Leu 755|Ser|Thr|Thr|Glu|Val 760|Thr|Phe|Asp|Thr|Pro 765|Tyr|Leu|Asp|
|Ile|Asn 770|Leu|Lys|Leu|Glu|Thr 775|Thr|Ser|Asn|Gln|Asp 780|Asn|Leu|Ala|Pro|
|Ile 785|Thr|Ala|Lys|Ala|Lys 790|Val|Val|Ile|Glu|Leu 795|Leu|Leu|Ser|Val|Ser 800|
|Gly|Val|Ala|Lys|Pro 805|Ser|Gln|Val|Tyr|Phe 810|Gly|Gly|Thr|Val|Val 815|Gly|
|Glu|Gln|Ala|Met 820|Lys|Ser|Glu|Asp|Glu 825|Val|Gly|Ser|Leu|Ile 830|Glu|Tyr|
|Glu|Phe|Arg 835|Val|Ile|Asn|Leu|Gly 840|Lys|Pro|Leu|Thr|Asn 845|Leu|Gly|Thr|
|Ala|Thr 850|Leu|Asn|Ile|Gln|Trp 855|Pro|Lys|Glu|Ile|Ser 860|Asn|Gly|Lys|Trp|
|Leu 865|Leu|Tyr|Leu|Val|Lys 870|Val|Glu|Ser|Lys|Gly 875|Leu|Glu|Lys|Val|Thr 880|
|Cys|Glu|Pro|Gln|Lys 885|Glu|Ile|Asn|Ser|Leu 890|Asn|Leu|Thr|Glu|Ser 895|His|
|Asn|Ser|Arg|Lys 900|Lys|Arg|Glu|Ile|Thr 905|Glu|Lys|Gln|Ile|Asp 910|Asp|Asn|
|Arg|Lys|Phe 915|Ser|Leu|Phe|Ala|Glu 920|Arg|Lys|Tyr|Gln|Thr 925|Leu|Asn|Cys|
|Ser|Val 930|Asn|Val|Asn|Cys|Val 935|Asn|Ile|Arg|Cys|Pro 940|Leu|Arg|Gly|Leu|
|Asp 945|Ser|Lys|Ala|Ser|Leu 950|Ile|Leu|Arg|Ser|Arg 955|Leu|Trp|Asn|Ser|Thr 960|
|Phe|Leu|Glu|Glu|Tyr 965|Ser|Lys|Leu|Asn|Tyr 970|Leu|Asp|Ile|Leu|Met 975|Arg|
|Ala|Phe|Ile|Asp 980|Val|Thr|Ala|Ala|Ala 985|Glu|Asn|Ile|Arg|Leu 990|Pro|Asn|

-continued

| Ala | Gly | Thr 995 | Gln | Val | Arg | Val 1000 | Thr | Val | Phe | Pro | Ser 1005 | Lys | Thr | Val | Ala |
| Gln | Tyr 1010 | Ser | Gly | Val | Pro | Trp 1015 | Trp | Ile | Ile | Leu | Val 1020 | Ala | Ile | Leu | Ala |
| Gly 1025 | Ile | Leu | Met | Leu 1030 | Ala | Leu | Leu | Val | Phe 1035 | Ile | Leu | Trp | Lys | Cys | Gly 1040 |
| Phe | Phe | Lys | Arg | Asn 1045 | Lys | Lys | Asp | His | Tyr 1050 | Asp | Ala | Thr | Tyr | His 1055 | Lys |
| Ala | Glu | Ile | His 1060 | Ala | Gln | Pro | Ser | Asp 1065 | Lys | Glu | Arg | Leu | Thr 1070 | Ser | Asp |
| Ala |

(2) INFORMATION FOR SEQ ID NO:2:

(i) SEQUENCE CHARACTERISTICS:
    (A) LENGTH: 5629 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Homo sapiens (ix) FEATURE:
    (A) NAME/KEY: miscfeature
    (B) LOCATION: 1..5629
    (D) OTHER INFORMATION: /product="Human ALPHA 6A"
        / note="SEQ ID NO: 2 is the 5629 base nucleotide
        sequence of the human ALPHA 6A cDNA."

(ix) FEATURE:
    (A) NAME/KEY: miscfeature
    (B) LOCATION: 147..149
    (D) OTHER INFORMATION: /function="Transcription
        initiator"

(ix) FEATURE:
    (A) NAME/KEY: matpeptide
    (B) LOCATION: 216..3365
    (D) OTHER INFORMATION: /product="Human ALPHA 6A"

(ix) FEATURE:
    (A) NAME/KEY: miscfeature
    (B) LOCATION: 3264..3278
    (D) OTHER INFORMATION: /product="The cytoplasmic sequence
        GFFKR."

(ix) FEATURE:
    (A) NAME/KEY: miscfeature
    (B) LOCATION: 3261..3390
    (D) OTHER INFORMATION: /note="The 130 nucleotide sequence
        present in SEQ ID NO: 2 but deleted from SEQ ID
        NO:4."

(ix) FEATURE:
    (A) NAME/KEY: miscfeature
    (B) LOCATION: 2924..3455
    (D) OTHER INFORMATION: /note="The sequence of the ALPHA
        6A cDNA amplified using primers 1156/1157."

(xi) SEQUENCE DESCRIPTION: SEQ ID NO:2:

```
GCGCGACCGT CCCGGGGGTG GGGCCGGGCG CAGCGGCGAG AGGAGGCGAA GGTGGCTGCG      60
GTAGCAGCAG CGCGGCAGCC TCGGACCCAG CCCGGAGCGC AGGGCGGCCG CTGCAGGTCC     120
CCGCTCCCCT CCCCGTGCGT CCGCCCATGG CCGCCGCCGG GCAGCTGTGC TTGCTCTACC     180
TGTCGGCGGG GCTCCTGTCC CGGCTCGGCG CAGCCTTCAA CTTGGACACT CGGGAGGACA     240
```

-continued

| | | | | | |
|---|---|---|---|---|---|
| ACGTGATCCG | GAAATATGGA | GACCCCGGGA | GCCTCTTCGG | CTTCTCGCTG | GCCATGCACT | 300
| GGCAACTGCA | GCCCGAGGAC | AAGCGGCTGT | TGCTCGTGGG | GGCCCCGCGC | GGAGAAGCGC | 360
| TTCCACTGCA | GAGAGCCTTC | AGAACGGGAG | GGCTGTACAG | CTGCGACATC | ACCGCCCGGG | 420
| GGCCATGCAC | GCGGATCGAG | TTTGATAACG | ATGCTGACCC | CACGTCAGAA | AGCAAGGAAG | 480
| ATCAGTGGAT | GGGGGTCACC | GTCCAGAGCC | AAGGTCCAGG | GGGCAAGGTC | GTGACATGTG | 540
| CTCACCGATA | TGAAAAAGG | CAGCATGTTA | ATACGAAGCA | GGAATCCCGA | GACATCTTTG | 600
| GGCGGTGTTA | TGTCCTGAGT | CAGAATCTCA | GGATTGAAGA | CGATATGGAT | GGGGAGATT | 660
| GGAGCTTTTG | TGATGGGCGA | TTGAGAGGCC | ATGAGAAATT | TGGCTCTTGC | CAGCAAGGTG | 720
| TAGCAGCTAC | TTTTACTAAA | GACTTTCATT | ACATTGTATT | TGGAGCCCCG | GGTACTTATA | 780
| ACTGGAAAGG | GATTGTTCGT | GTAGAGCAAA | AGAATAACAC | TTTTTTTGAC | ATGAACATCT | 840
| TTGAAGATGG | GCCTTATGAA | GTTGGTGGAG | AGACTGAGCA | TGATGAAAGT | CTCGTTCCTG | 900
| TTCCTGCTAA | CAGTTACTTA | GGTTTTTCTT | TGGACTCAGG | GAAAGGTATT | GTTTCTAAAG | 960
| ATGAGATCAC | TTTTGTATCT | GGTGCTCCCA | GAGCCAATCA | CAGTGGAGCC | GTGGTTTTGC | 1020
| TGAAGAGAGA | CATGAAGTCT | GCACATCTCC | TCCCTGAGCA | CATATTCGAT | GGAGAAGGTC | 1080
| TGGCCTCTTC | ATTTGGCTAT | GATGTGGCGG | TGATGGACCT | CAACAAGGAT | GGGTGGCAAG | 1140
| ATATAGTTAT | TGGAGCCCCA | CAGTATTTTG | ATAGAGATGG | AGAAGTTGGA | GGTGCAGTGT | 1200
| ATGTCTACAT | GAACCAGCAA | GGCAGATGGA | ATAATGTGAA | GCCAATTCGT | CTTAATGGAA | 1260
| CCAAAGATTC | TATGTTTGGC | ATTGCAGTAA | AAATATTGG | AGATATTAAT | CAAGATGGCT | 1320
| ACCCAGATAT | TGCAGTTGGA | GCTCCGTATG | ATGACTTGGG | AAAGGTTTTT | ATCTATCATG | 1380
| GATCTGCAAA | TGGAATAAAT | ACCAAACCAA | CACAGGTTCT | CAAGGGTATA | TCACCTTATT | 1440
| TTGGATATTC | AATTGCTGGA | ACATGGACC | TTGATCGAAA | TTCCTACCCT | GATGTTGCTG | 1500
| TTGGTTCCCT | CTCAGATTCA | GTAACTATTT | TCAGATCCCG | GCCTGTGATT | AATATTCAGA | 1560
| AAACCATCAC | AGTAACTCCT | AACAGAATTG | ACCTCCGCCA | GAAACAGCG | TGTGGGGCGC | 1620
| CTAGTGGGAT | ATGCCTCCAG | GTTAAATCCT | GTTTTGAATA | TACTGCTAAC | CCCGCTGGTT | 1680
| ATAATCCTTC | AATATCAATT | GTGGGCACAC | TTGAAGCTGA | AAAAGAAAGA | AGAAAATCTG | 1740
| GGCTATCCTC | AAGAGTTCAG | TTTCGAAACC | AAGGTTCTGA | GCCCAAATAT | ACTCAAGAAC | 1800
| TAACTCTGAA | GAGGCAGAAA | CAGAAAGTGT | GCATGGAGGA | AACCCTGTGG | CTACAGGATA | 1860
| ATATCAGAGA | TAAACTGCGT | CCCATTCCCA | TAACTGCCTC | AGTGGAGATC | CAAGAGCCAA | 1920
| GCTCTCGTAG | GCGAGTGAAT | TCACTTCCAG | AAGTTCTTCC | AATTCTGAAT | TCAGATGAAC | 1980
| CCAAGACAGC | TCATATTGAT | GTTCACTTCT | TAAAAGAGGG | ATGTGGAGAC | GACAATGTAT | 2040
| GTAACAGCAA | CCTTAAACTA | GAATATAAAT | TTGCACCCG | AGAAGGAAAT | CAAGACAAAT | 2100
| TTTCTTATTT | ACCAATTCAA | AAAGGTGTAC | CAGAACTAGT | TCTAAAGAT | CAGAAGGATA | 2160
| TTGCTTTAGA | AATAACAGTG | ACAAACAGCC | CTTCCAACCC | AAGGAATCCC | ACAAAAGATG | 2220
| GCGATGACGC | CCATGAGGCT | AAACTGATTG | CAACGTTTCC | AGACACTTTA | ACCTATTCTG | 2280
| CATATAGAGA | ACTGAGGGCT | TTCCCTGAGA | AACAGTTGAG | TTGTGTTGCC | AACCAGAATG | 2340
| GCTCGCAAGC | TGACTGTGAG | CTCGGAAATC | CTTTTAAAAG | AAATTCAAAT | GTCACTTTTT | 2400
| ATTTGGTTTT | AAGTACAACT | GAAGTCACCT | TTGACACCCC | ATATCTGGAT | ATTAATCTGA | 2460
| AGTTAGAAAC | AACAAGCAAT | CAAGATAATT | TGGCTCCAAT | TACAGCTAAA | GCAAAAGTGG | 2520
| TTATTGAACT | GCTTTTATCG | GTCTCGGGAG | TTGCTAAACC | TTCCCAGGTG | TATTTTGGAG | 2580
| GTACAGTTGT | TGGCGAGCAA | GCTATGAAAT | CTGAAGATGA | AGTGGGAAGT | TTAATAGAGT | 2640
| ATGAATTCAG | GGTAATAAAC | TTAGGTAAAC | CTCTTACAAA | CCTCGGCACA | GCAACCTTGA | 2700

```
ACATTCAGTG GCCAAAAGAA ATTAGCAATG GGAAATGGTT GCTTTATTTG GTGAAAGTAG    2760
AATCCAAAGG ATTGGAAAAG GTAACTTGTG AGCCACAAAA GGAGATAAAC TCCCTGAACC    2820
TAACGGAGTC TCACAACTCA AGAAAGAAAC GGGAAATTAC TGAAAAACAG ATAGATGATA    2880
ACAGAAAATT TTCTTTATTT GCTGAAAGAA AATACCAGAC TCTTAACTGT AGCGTGAACG    2940
TGAACTGTGT GAACATCAGA TGCCCGCTGC GGGGGCTGGA CAGCAAGGCG TCTCTTATTT    3000
TGCGCTCGAG GTTATGGAAC AGCACATTTC TAGAGGAATA TTCCAAACTG AACTACTTGG    3060
ACATTCTCAT GCGAGCCTTC ATTGATGTGA CTGCTGCTGC CGAAAATATC AGGCTGCCAA    3120
ATGCAGGCAC TCAGGTTCGA GTGACTGTGT TTCCCTCAAA GACTGTAGCT CAGTATTCGG    3180
GAGTACCTTG GTGGATCATC CTAGTGGCTA TTCTCGCTGG GATCTTGATG CTTGCTTTAT    3240
TAGTGTTTAT ACTATGGAAG TGTGGTTTCT TCAAGAGAAA TAAGAAAGAT CATTATGATG    3300
CCACATATCA CAAGGCTGAG ATCCATGCTC AGCCATCTGA TAAAGAGAGG CTTACTTCTG    3360
ATGCATAGTA TTGATCTACT TCTGTAATTG TGTGGATTCT TTAAACGCTC TAGGTACGAT    3420
GACAGTGTTC CCCGATACCA TGCTGTAAGG ATCCGGAAAG AAGAGCGAGA GATCAAAGAT    3480
GAAAGTATA TTGATAACCT TGAAAAAAAA CAGTGGATCA CAAAGTGGAA CAGAAATGAA    3540
AGCTACTCAT AGCGGGGGCC TAAAAAAAAA AAAGCTTCAC AGTACCCAAA CTGCTTTTC     3600
CAACTCAGAA ATTCAATTTG GATTTAAAAG CCTGCTCAAT CCCTGAGGAC TGATTTCAGA    3660
GTGACTACAC ACAGTACGAA CCTACAGTTT TAACTGTGGA TATTGTTACG TAGCCTAAGG    3720
CTCCTGTTTT GCACAGCCAA ATTTAAAACT GTTGGAATGG ATTTTTCTTT AACTGCCGTA    3780
ATTTAACTTT CTGGGTTGCC TTTGTTTTTG GCGTGGCTGA CTTACATCAT GTGTTGGGGA    3840
AGGGCCTGCC CAGTTGCACT CAGGTGACAT CCTCCAGATA GTGTAGCTGA GGAGGCACCT    3900
ACACTCACCT GCACTAACAG AGTGGCCGTC CTAACCTCGG GCCTGCTGCG CAGACGTCCA    3960
TCACGTTAGC TGTCCCACAT CACAAGACTA TGCCATTGGG GTAGTTGTGT TTCAACGGAA    4020
AGTGCTGTCT TAAACTAAAT GTGCAATAGA AGGTGATGTT GCCATCCTAC CGTCTTTTCC    4080
TGTTTCCTAG CTGTGTGAAT ACCTGCTCAC GTCAAATGCA TACAAGTTTC ATTCTCCCTT    4140
TCACTAAAAA CACACAGGTG CAACAGACTT GAATGCTAGT TATACTTATT TGTATATGGT    4200
ATTTATTTTT TCTTTCTTT ACAAACCATT TTGTTATTGA CTAACAGGCC AAAGAGTCTC     4260
CAGTTTACCC TTCAGGTTGG TTTAATCAAT CAGAATTAGA ATTAGAGCAT GGGAGGGTCA    4320
TCACTATGAC CTAAATTATT TACTGCAAAA AGAAAATCTT TATAAATGTA CCAGAGAGAG    4380
TTGTTTTAAT AACTTATCTA TAAACTATAA CCTCTCCTTC ATGACAGCCT CCACCCCACA    4440
ACCCAAAAGG TTTAAGAAAT AGAATTATAA CTGTAAAGAT GTTTATTTCA GGCATTGGAT    4500
ATTTTTACT TTAGAAGCCT GCATAATGTT TCTGGATTTA CATACTGTAA CATTCAGGAA     4560
TTCTTGGAGA AGATGGGTTT ATTCACTGAA CTCTAGTGCG GTTACTCAC TGCTGCAAAT     4620
ACTGTATATT CAGGACTTGA AAGAAATGGT GAATGCCTAT GGAACTAGTG ATCCAAACT     4680
GATCCAGTAT AAGACTACTG AATCTGCTAC CAAAACAGTT AATCAGTGAG TCGAGTGTTC    4740
TATTTTTGT TTGTTCCT CCCCTATCTG TATTCCCAAA AATTACTTTG GGCTAATTT        4800
AACAAGAACT TTAAATTGTG TTTTAATTGT AAAAATGGCA GGGGGTGGAA TTATTACTCT    4860
ATACATTCAA CAGAGACTGA ATAGATATGA AAGCTGATTT TTTTAATTA CCATGCTTCA     4920
CAATGTTAAG TTATATGGGG AGCAACAGCA AACAGGTGCT AATTTGTTTT GGATATAGTA    4980
TAAGCAGTGT CTGTGTTTTG AAAGAATAGA ACACAGTTTG TAGTGCCACT GTTGTTTTGG    5040
GGGGGGCTTT TTTTCTTTTT CCGGAAAATC CTTAAACCTT AAGATACTAA GGACGTTGTT    5100
TTGGTTGTAC TTGGAATTCT TAGTCACAAA ATATATTTTG TTTACAAAAA TTTCTGTAAA    5160
```

-continued

| ACAGGTTATA | ACAGTGTTTA | AAGTCTCAGT | TTCTTGCTTG | GGGAACTTGT | GTCCCTAATG | 5220 |
| TGTTAGATTG | CTAGATTGCT | AAGGAGCTGA | TACTTGACAG | TTTTTTAGAC | CTGTGTTACT | 5280 |
| AAAAAAAAGA | TGAATGTCGG | AAAAGGGTGT | TGGGAGGGTG | GTCAACAAAG | AAACAAAGAT | 5340 |
| GTTATGGTGT | TTAGACTTAT | GGTTGTTAAA | AATGTCATCT | CAAGTCAAGT | CACTGGTCTG | 5400 |
| TTTGCATTTG | ATACATTTTT | GTACTAACTA | GCATTGTAAA | ATTATTTCAT | GATTAGAAAT | 5460 |
| TACCTGTGGA | TATTTGTATA | AAAGTGTGAA | ATAAATTTTT | TATAAAAGTG | TTCATTGTTT | 5520 |
| CGTAACACAG | CATTGTATAT | GTGAAGCAAA | CTCTAAAATT | ATAAATGACA | ACCTGAATTA | 5580 |
| TCTATTTCAT | CAAAAAAAAA | AAAAAAAAAA | ACTTTATGGG | CACAACTGG | | 5629 |

( 2 ) INFORMATION FOR SEQ ID NO:3:

( i ) SEQUENCE CHARACTERISTICS:
        ( A ) LENGTH: 1091 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: Region
        ( B ) LOCATION: 1..1091
        ( D ) OTHER INFORMATION: /note="SEQ ID NO:3 is the 1091
            residue amino acid sequence of the human ALPHA 6B
            protein."

( i x ) FEATURE:
        ( A ) NAME/KEY: Region
        ( B ) LOCATION: 1..1044
        ( D ) OTHER INFORMATION: /note="The sequence of SEQ ID NO:3
            is identical to SEQ ID NO:1 between amino acids 1
            and 1044."

( i x ) FEATURE:
        ( A ) NAME/KEY: Region
        ( B ) LOCATION: 927..1060
        ( D ) OTHER INFORMATION: /note="Encompasses the sequence
            encoded by the fragment of ALPHA 6B cDNA amplified
            using primers 1156/1157."

( x i ) SEQUENCE DESCRIPTION: SEQ ID NO:3:

```
Met Ala Ala Ala Gly Gln Leu Cys Leu Leu Tyr Leu Ser Ala Gly Leu
 1               5                  10                  15

Leu Ser Arg Leu Gly Ala Ala Phe Asn Leu Asp Thr Arg Glu Asp Asn
                20                  25                  30

Val Ile Arg Lys Tyr Gly Asp Pro Gly Ser Leu Phe Gly Phe Ser Leu
            35                  40                  45

Ala Met His Trp Gln Leu Gln Pro Glu Asp Lys Arg Leu Leu Leu Val
        50                  55                  60

Gly Ala Pro Arg Gly Glu Ala Leu Pro Leu Gln Arg Ala Phe Arg Thr
65                  70                  75                  80

Gly Gly Leu Tyr Ser Cys Asp Ile Thr Ala Arg Gly Pro Cys Thr Arg
                85                  90                  95

Ile Glu Phe Asp Asn Asp Ala Asp Pro Thr Ser Glu Ser Lys Glu Asp
               100                 105                 110

Gln Trp Met Gly Val Thr Val Gln Ser Gln Gly Pro Gly Gly Lys Val
           115                 120                 125

Val Thr Cys Ala His Arg Tyr Glu Lys Arg Gln His Val Asn Thr Lys
        130                 135                 140
```

```
Gln Glu Ser Arg Asp Ile Phe Gly Arg Cys Tyr Val Leu Ser Gln Asn
145                 150                 155                 160

Leu Arg Ile Glu Asp Asp Met Asp Gly Gly Asp Trp Ser Phe Cys Asp
                165                 170                 175

Gly Arg Leu Arg Gly His Glu Lys Phe Gly Ser Cys Gln Gln Gly Val
            180                 185                 190

Ala Ala Thr Phe Thr Lys Asp Phe His Tyr Ile Val Phe Gly Ala Pro
        195                 200                 205

Gly Thr Tyr Asn Trp Lys Gly Ile Val Arg Val Glu Gln Lys Asn Asn
    210                 215                 220

Thr Phe Phe Asp Met Asn Ile Phe Glu Asp Gly Pro Tyr Glu Val Gly
225                 230                 235                 240

Gly Glu Thr Glu His Asp Glu Ser Leu Val Pro Val Pro Ala Asn Ser
                245                 250                 255

Tyr Leu Gly Phe Ser Leu Asp Ser Gly Lys Gly Ile Val Ser Lys Asp
            260                 265                 270

Glu Ile Thr Phe Val Ser Gly Ala Pro Arg Ala Asn His Ser Gly Ala
        275                 280                 285

Val Val Leu Leu Lys Arg Asp Met Lys Ser Ala His Leu Leu Pro Glu
290                 295                 300

His Ile Phe Asp Gly Glu Gly Leu Ala Ser Ser Phe Gly Tyr Asp Val
305                 310                 315                 320

Ala Val Met Asp Leu Asn Lys Asp Gly Trp Gln Asp Ile Val Ile Gly
                325                 330                 335

Ala Pro Gln Tyr Phe Asp Arg Asp Gly Glu Val Gly Gly Ala Val Tyr
            340                 345                 350

Val Tyr Met Asn Gln Gln Gly Arg Trp Asn Asn Val Lys Pro Ile Arg
        355                 360                 365

Leu Asn Gly Thr Lys Asp Ser Met Phe Gly Ile Ala Val Lys Asn Ile
370                 375                 380

Gly Asp Ile Asn Gln Asp Gly Tyr Pro Asp Ile Ala Val Gly Ala Pro
385                 390                 395                 400

Tyr Asp Asp Leu Gly Lys Val Phe Ile Tyr His Gly Ser Ala Asn Gly
                405                 410                 415

Ile Asn Thr Lys Pro Thr Gln Val Leu Lys Gly Ile Ser Pro Tyr Phe
            420                 425                 430

Gly Tyr Ser Ile Ala Gly Asn Met Asp Leu Asp Arg Asn Ser Tyr Pro
        435                 440                 445

Asp Val Ala Val Gly Ser Leu Ser Asp Ser Val Thr Ile Phe Arg Ser
450                 455                 460

Arg Pro Val Ile Asn Ile Gln Lys Thr Ile Thr Val Thr Pro Asn Arg
465                 470                 475                 480

Ile Asp Leu Arg Gln Lys Thr Ala Cys Gly Ala Pro Ser Gly Ile Cys
                485                 490                 495

Leu Gln Val Lys Ser Cys Phe Glu Tyr Thr Ala Asn Pro Ala Gly Tyr
            500                 505                 510

Asn Pro Ser Ile Ser Ile Val Gly Thr Leu Glu Ala Glu Lys Glu Arg
        515                 520                 525

Arg Lys Ser Gly Leu Ser Ser Arg Val Gln Phe Arg Asn Gln Gly Ser
530                 535                 540

Glu Pro Lys Tyr Thr Gln Glu Leu Thr Leu Lys Arg Gln Lys Gln Lys
545                 550                 555                 560

Val Cys Met Glu Glu Thr Leu Trp Leu Gln Asp Asn Ile Arg Asp Lys
                565                 570                 575
```

| | | | | | | | | | | | | | | |
|---|---|---|---|---|---|---|---|---|---|---|---|---|---|---|
| Leu | Arg | Pro | Ile<br>580 | Pro | Ile | Thr | Ala | Ser<br>585 | Val | Glu | Ile | Gln<br>590 | Glu | Pro | Ser |
| Ser | Arg | Arg<br>595 | Arg | Val | Asn | Ser | Leu<br>600 | Pro | Glu | Val | Leu | Pro<br>605 | Ile | Leu | Asn |
| Ser | Asp<br>610 | Glu | Pro | Lys | Thr | Ala<br>615 | His | Ile | Asp | Val | His<br>620 | Phe | Leu | Lys | Glu |
| Gly<br>625 | Cys | Gly | Asp | Asp<br>630 | Asn | Val | Cys | Asn | Ser<br>635 | Asn | Leu | Lys | Leu | Glu | Tyr<br>640 |
| Lys | Phe | Cys | Thr | Arg<br>645 | Glu | Gly | Asn | Gln | Asp<br>650 | Lys | Phe | Ser | Tyr | Leu<br>655 | Pro |
| Ile | Gln | Lys | Gly<br>660 | Val | Pro | Glu | Leu | Val<br>665 | Leu | Lys | Asp | Gln | Lys<br>670 | Asp | Ile |
| Ala | Leu | Glu<br>675 | Ile | Thr | Val | Thr | Asn<br>680 | Ser | Pro | Ser | Asn | Pro<br>685 | Arg | Asn | Pro |
| Thr | Lys<br>690 | Asp | Gly | Asp | Asp<br>695 | Ala | His | Glu | Ala | Lys<br>700 | Leu | Ile | Ala | Thr | Phe |
| Pro<br>705 | Asp | Thr | Leu | Thr | Tyr<br>710 | Ser | Ala | Tyr | Arg | Glu<br>715 | Leu | Arg | Ala | Phe | Pro<br>720 |
| Glu | Lys | Gln | Leu | Ser<br>725 | Cys | Val | Ala | Asn | Gln<br>730 | Asn | Gly | Ser | Gln | Ala<br>735 | Asp |
| Cys | Glu | Leu | Gly<br>740 | Asn | Pro | Phe | Lys | Arg<br>745 | Asn | Ser | Asn | Val | Thr<br>750 | Phe | Tyr |
| Leu | Val | Leu<br>755 | Ser | Thr | Thr | Glu | Val<br>760 | Thr | Phe | Asp | Thr | Pro<br>765 | Tyr | Leu | Asp |
| Ile | Asn<br>770 | Leu | Lys | Leu | Glu | Thr<br>775 | Thr | Ser | Asn | Gln | Asp<br>780 | Asn | Leu | Ala | Pro |
| Ile<br>785 | Thr | Ala | Lys | Ala | Lys<br>790 | Val | Val | Ile | Glu | Leu<br>795 | Leu | Leu | Ser | Val | Ser<br>800 |
| Gly | Val | Ala | Lys | Pro<br>805 | Ser | Gln | Val | Tyr | Phe<br>810 | Gly | Gly | Thr | Val | Val<br>815 | Gly |
| Glu | Gln | Ala | Met<br>820 | Lys | Ser | Glu | Asp | Glu<br>825 | Val | Gly | Ser | Leu | Ile<br>830 | Glu | Tyr |
| Glu | Phe | Arg<br>835 | Val | Ile | Asn | Leu | Gly<br>840 | Lys | Pro | Leu | Thr | Asn<br>845 | Leu | Gly | Thr |
| Ala | Thr<br>850 | Leu | Asn | Ile | Gln | Trp<br>855 | Pro | Lys | Glu | Ile | Ser<br>860 | Asn | Gly | Lys | Trp |
| Leu<br>865 | Leu | Tyr | Leu | Val | Lys<br>870 | Val | Glu | Ser | Lys | Gly<br>875 | Leu | Glu | Lys | Val | Thr<br>880 |
| Cys | Glu | Pro | Gln | Lys<br>885 | Glu | Ile | Asn | Ser | Leu<br>890 | Asn | Leu | Thr | Glu | Ser<br>895 | His |
| Asn | Ser | Arg | Lys<br>900 | Lys | Arg | Glu | Ile | Thr<br>905 | Glu | Lys | Gln | Ile | Asp<br>910 | Asp | Asn |
| Arg | Lys | Phe<br>915 | Ser | Leu | Phe | Ala | Glu<br>920 | Arg | Lys | Tyr | Gln | Thr<br>925 | Leu | Asn | Cys |
| Ser | Val<br>930 | Asn | Val | Asn | Cys | Val<br>935 | Asn | Ile | Arg | Cys | Pro<br>940 | Leu | Arg | Gly | Leu |
| Asp<br>945 | Ser | Lys | Ala | Ser | Leu<br>950 | Ile | Leu | Arg | Ser | Arg<br>955 | Leu | Trp | Asn | Ser | Thr<br>960 |
| Phe | Leu | Glu | Glu | Tyr<br>965 | Ser | Lys | Leu | Asn | Tyr<br>970 | Leu | Asp | Ile | Leu | Met<br>975 | Arg |
| Ala | Phe | Ile | Asp<br>980 | Val | Thr | Ala | Ala | Glu<br>985 | Asn | Ile | Arg | Leu | Pro<br>990 | Asn |  |
| Ala | Gly | Thr<br>995 | Gln | Val | Arg | Val | Thr<br>1000 | Val | Phe | Pro | Ser | Lys<br>1005 | Thr | Val | Ala |
| Gln | Tyr | Ser | Gly | Val | Pro | Trp | Trp | Ile | Ile | Leu | Val | Ala | Ile | Leu | Ala |

|  |  | 1010 |  |  |  |  | 1015 |  |  |  |  | 1020 |  |  |

Gly Ile Leu Met Leu Ala Leu Leu Val Phe Ile Leu Trp Lys Cys Gly
1025                     1030                1035                     1040

Phe Phe Lys Arg Ser Arg Tyr Asp Asp Ser Val Pro Arg Tyr His Ala
                1045                    1050                1055

Val Arg Ile Arg Lys Glu Glu Arg Glu Ile Lys Asp Glu Lys Tyr Ile
            1060                    1065                1070

Asp Asn Leu Glu Lys Lys Gln Trp Ile Thr Lys Trp Asn Arg Asn Glu
        1075                    1080                    1085

Ser Tyr Ser
1090

(2) INFORMATION FOR SEQ ID NO:4:

(i) SEQUENCE CHARACTERISTICS:
  (A) LENGTH: 5499 base pairs
  (B) TYPE: nucleic acid
  (C) STRANDEDNESS: double
  (D) TOPOLOGY: linear (ii) MOLECULE TYPE: cDNA (iii) HYPOTHETICAL: NO (iv) ANTI-SENSE: NO (vi) ORIGINAL SOURCE:
  (A) ORGANISM: Homo sapiens (ix) FEATURE:
  (A) NAME/KEY: miscfeature
  (B) LOCATION: 1..5499
  (D) OTHER INFORMATION: /product="Human ALPHA 6B"

(ix) FEATURE:
  (A) NAME/KEY: miscfeature
  (B) LOCATION: 1..3260
  (D) OTHER INFORMATION: /note="The sequence of SEQ ID NO:4
   is identical to SEQ ID NO:2 between nucleotides 1
   and 3260."

(ix) FEATURE:
  (A) NAME/KEY: miscfeature
  (B) LOCATION: 3261..5499
  (D) OTHER INFORMATION: /note="Nucleotides 3261-5499 of
   SEQ ID NO:4 are identical to nucleotides 3391-5629
   of SEQ ID NO:2. SEQ ID NO:4 has a 130 nucleotide
   deletion in relation to SEQ ID NO:2."

(ix) FEATURE:
  (A) NAME/KEY: miscfeature
  (B) LOCATION: 2924..3325
  (D) OTHER INFORMATION: /note="Encompasses the sequence of
   the ALPHA 6B cDNA amplified using primers
   1156/1157."

(xi) SEQUENCE DESCRIPTION: SEQ ID NO:4:

```
GCGCGACCGT CCCGGGGGTG GGGCCGGGCG CAGCGGCGAG AGGAGGCGAA GGTGGCTGCG     60
GTAGCAGCAG CGCGGCAGCC TCGGACCCAG CCCGGAGCGC AGGGCGGCCG CTGCAGGTCC    120
CCGCTCCCCT CCCCGTGCGT CCGCCCATGG CCGCCGCCGG GCAGCTGTGC TTGCTCTACC    180
TGTCGGCGGG GCTCCTGTCC CGGCTCGGCG CAGCCTTCAA CTTGGACACT CGGGAGGACA    240
ACGTGATCCG GAAATATGGA GACCCCGGGA GCCTCTTCGG CTTCTCGCTG GCCATGCACT    300
GGCAACTGCA GCCCGAGGAC AAGCGGCTGT TGCTCGTGGG GGCCCCGCGC GGAGAAGCGC    360
TTCCACTGCA GAGAGCCTTC AGAACGGGAG GGCTGTACAG CTGCGACATC ACCGCCCGGG    420
GGCCATGCAC GCGGATCGAG TTTGATAACG ATGCTGACCC CACGTCAGAA AGCAAGGAAG    480
ATCAGTGGAT GGGGGTCACC GTCCAGAGCC AAGGTCCAGG GGGCAAGGTC GTGACATGTG    540
```

```
CTCACCGATA  TGAAAAAAGG  CAGCATGTTA  ATACGAAGCA  GGAATCCCGA  GACATCTTTG   600
GGCGGTGTTA  TGTCCTGAGT  CAGAATCTCA  GGATTGAAGA  CGATATGGAT  GGGGGAGATT   660
GGAGCTTTTG  TGATGGGCGA  TTGAGAGGCC  ATGAGAAATT  TGGCTCTTGC  CAGCAAGGTG   720
TAGCAGCTAC  TTTTACTAAA  GACTTTCATT  ACATTGTATT  TGGAGCCCCG  GGTACTTATA   780
ACTGGAAAGG  GATTGTTCGT  GTAGAGCAAA  AGAATAACAC  TTTTTTTGAC  ATGAACATCT   840
TTGAAGATGG  GCCTTATGAA  GTTGGTGGAG  AGACTGAGCA  TGATGAAAGT  CTCGTTCCTG   900
TTCCTGCTAA  CAGTTACTTA  GGTTTTTCTT  TGGACTCAGG  GAAAGGTATT  GTTTCTAAAG   960
ATGAGATCAC  TTTTGTATCT  GGTGCTCCCA  GAGCCAATCA  CAGTGGAGCC  GTGGTTTTGC  1020
TGAAGAGAGA  CATGAAGTCT  GCACATCTCC  TCCCTGAGCA  CATATTCGAT  GGAGAAGGTC  1080
TGGCCTCTTC  ATTTGGCTAT  GATGTGGCGG  TGATGGACCT  CAACAAGGAT  GGGTGGCAAG  1140
ATATAGTTAT  TGGAGCCCCA  CAGTATTTTG  ATAGAGATGG  AGAAGTTGGA  GGTGCAGTGT  1200
ATGTCTACAT  GAACCAGCAA  GGCAGATGGA  ATAATGTGAA  GCCAATTCGT  CTTAATGGAA  1260
CCAAAGATTC  TATGTTTGGC  ATTGCAGTAA  AAAATATTGG  AGATATTAAT  CAAGATGGCT  1320
ACCCAGATAT  TGCAGTTGGA  GCTCCGTATG  ATGACTTGGG  AAAGGTTTTT  ATCTATCATG  1380
GATCTGCAAA  TGGAATAAAT  ACCAAACCAA  CACAGGTTCT  CAAGGGTATA  TCACCTTATT  1440
TTGGATATTC  AATTGCTGGA  ACATGGACC   TTGATCGAAA  TTCCTACCCT  GATGTTGCTG  1500
TTGGTTCCCT  CTCAGATTCA  GTAACTATTT  TCAGATCCCG  GCCTGTGATT  AATATTCAGA  1560
AAACCATCAC  AGTAACTCCT  AACAGAATTG  ACCTCCGCCA  GAAAACAGCG  TGTGGGGCGC  1620
CTAGTGGGAT  ATGCCTCCAG  GTTAAATCCT  GTTTTGAATA  TACTGCTAAC  CCCGCTGGTT  1680
ATAATCCTTC  AATATCAATT  GTGGGCACAC  TTGAAGCTGA  AAAAGAAAGA  AGAAAATCTG  1740
GGCTATCCTC  AAGAGTTCAG  TTTCGAAACC  AAGGTTCTGA  GCCCAAATAT  ACTCAAGAAC  1800
TAACTCTGAA  GAGGCAGAAA  CAGAAAGTGT  GCATGGAGGA  AACCCTGTGG  CTACAGGATA  1860
ATATCAGAGA  TAAACTGCGT  CCCATTCCCA  TAACTGCCTC  AGTGGAGATC  AAGAGCCAA   1920
GCTCTCGTAG  GCGAGTGAAT  TCACTTCCAG  AAGTTCTTCC  AATTCTGAAT  TCAGATGAAC  1980
CCAAGACAGC  TCATATTGAT  GTTCACTTCT  TAAAAGAGGG  ATGTGGAGAC  GACAATGTAT  2040
GTAACAGCAA  CCTTAAACTA  GAATATAAAT  TTTGCACCCG  AGAAGGAAAT  CAAGACAAAT  2100
TTTCTTATTT  ACCAATTCAA  AAAGGTGTAC  CAGAACTAGT  TCTAAAAGAT  CAGAAGGATA  2160
TTGCTTTAGA  ATAACAGTG   ACAAACAGCC  CTTCCAACCC  AAGGAATCCC  ACAAAAGATG  2220
GCGATGACGC  CCATGAGGCT  AAACTGATTG  CAACGTTTCC  AGACACTTTA  ACCTATTCTG  2280
CATATAGAGA  ACTGAGGGCT  TTCCCTGAGA  AACAGTTGAG  TTGTGTTGCC  AACCAGAATG  2340
GCTCGCAAGC  TGACTGTGAG  CTCGGAAATC  CTTTTAAAAG  AAATTCAAAT  GTCACTTTTT  2400
ATTTGGTTTT  AAGTACAACT  GAAGTCACCT  TTGACACCCC  ATATCTGGAT  ATTAATCTGA  2460
AGTTAGAAAC  AACAAGCAAT  CAAGATAATT  TGGCTCCAAT  TACAGCTAAA  GCAAAAGTGG  2520
TTATTGAACT  GCTTTTATCG  GTCTCGGGAG  TTGCTAAACC  TTCCCAGGTG  TATTTTGGAG  2580
GTACAGTTGT  TGGCGAGCAA  GCTATGAAAT  CTGAAGATGA  AGTGGAAGT   TTAATAGAGT  2640
ATGAATTCAG  GGTAATAAAC  TTAGGTAAAC  CTCTTACAAA  CCTCGGCACA  GCAACCTTGA  2700
ACATTCAGTG  GCCAAAAGAA  ATTAGCAATG  GAAATGGTT   GCTTTATTTG  GTGAAAGTAG  2760
AATCCAAAGG  ATTGGAAAAG  GTAACTTGTG  AGCCACAAAA  GGAGATAAAC  TCCCTGAACC  2820
TAACGGAGTC  TCACAACTCA  AGAAGAAAC   GGGAATTAC   TGAAAAACAG  ATAGATGATA  2880
ACAGAAAATT  TTCTTTATTT  GCTGAAAGAA  AATACCAGAC  TCTTAACTGT  AGCGTGAACG  2940
TGAACTGTGT  GAACATCAGA  TGCCCGCTGC  GGGGGCTGGA  CAGCAAGGCG  TCTCTTATTT  3000
```

```
TGCGCTCGAG GTTATGGAAC AGCACATTTC TAGAGGAATA TTCCAAACTG AACTACTTGG   3060
ACATTCTCAT GCGAGCCTTC ATTGATGTGA CTGCTGCTGC CGAAAATATC AGGCTGCCAA   3120
ATGCAGGCAC TCAGGTTCGA GTGACTGTGT TTCCCTCAAA GACTGTAGCT CAGTATTCGG   3180
GAGTACCTTG GTGGATCATC CTAGTGGCTA TTCTCGCTGG GATCTTGATG CTTGCTTTAT   3240
TAGTGTTTAT ACTATGGAAG TGTGGATTCT TTAAACGCTC TAGGTACGAT GACAGTGTTC   3300
CCCGATACCA TGCTGTAAGG ATCCGGAAAG AAGAGCGAGA GATCAAAGAT GAAAAGTATA   3360
TTGATAACCT TGAAAAAAAA CAGTGGATCA CAAAGTGGAA CAGAAATGAA AGCTACTCAT   3420
AGCGGGGGCC TAAAAAAAAA AAAGCTTCAC AGTACCCAAA CTGCTTTTTC CAACTCAGAA   3480
ATTCAATTTG GATTTAAAAG CCTGCTCAAT CCCTGAGGAC TGATTTCAGA GTGACTACAC   3540
ACAGTACGAA CCTACAGTTT TAACTGTGGA TATTGTTACG TAGCCTAAGG CTCCTGTTTT   3600
GCACAGCCAA ATTTAAAACT GTTGGAATGG ATTTTTCTTT AACTGCCGTA ATTTAACTTT   3660
CTGGGTTGCC TTTGTTTTTG GCGTGGCTGA CTTACATCAT GTGTTGGGGA AGGGCCTGCC   3720
CAGTTGCACT CAGGTGACAT CCTCCAGATA GTGTAGCTGA GGAGGCACCT ACACTCACCT   3780
GCACTAACAG AGTGGCCGTC CTAACCTCGG GCCTGCTGCG CAGACGTCCA TCACGTTAGC   3840
TGTCCCACAT CACAAGACTA TGCCATTGGG GTAGTTGTGT TCAACGGAA AGTGCTGTCT    3900
TAAACTAAAT GTGCAATAGA AGGTGATGTT GCCATCCTAC CGTCTTTTCC TGTTTCCTAG   3960
CTGTGTGAAT ACCTGCTCAC GTCAAATGCA TACAAGTTTC ATTCTCCCTT TCACTAAAAA   4020
CACACAGGTG CAACAGACTT GAATGCTAGT TATACTTATT TGTATATGGT ATTTATTTTT   4080
TCTTTTCTTT ACAAACCATT TTGTTATTGA CTAACAGGCC AAAGAGTCTC CAGTTACCC    4140
TTCAGGTTGG TTTAATCAAT CAGAATTAGA ATTAGAGCAT GGGAGGGTCA TCACTATGAC   4200
CTAAATTATT TACTGCAAAA AGAAATCTT TATAAATGTA CCAGAGAGAG TTGTTTTAAT    4260
AACTTATCTA TAAACTATAA CCTCTCCTTC ATGACAGCCT CCACCCCACA ACCCAAAGG    4320
TTTAAGAAAT AGAATTATAA CTGTAAAGAT GTTTATTTCA GGCATTGGAT ATTTTTTACT   4380
TTAGAAGCCT GCATAATGTT TCTGGATTTA CATACTGTAA CATTCAGGAA TTCTTGGAGA   4440
AGATGGGTTT ATTCACTGAA CTCTAGTGCG GTTACTCAC TGCTGCAAAT ACTGTATATT    4500
CAGGACTTGA AAGAAATGGT GAATGCCTAT GGAACTAGTG GATCCAAACT GATCCAGTAT   4560
AAGACTACTG AATCTGCTAC CAAAACAGTT AATCAGTGAG TCGAGTGTTC TATTTTTGT    4620
TTTGTTTCCT CCCCTATCTG TATTCCCAAA AATTACTTTG GGCTAATTT AACAAGAACT    4680
TTAAATTGTG TTTTAATTGT AAAAATGGCA GGGGGTGGAA TTATTACTCT ATACATTCAA   4740
CAGAGACTGA ATAGATATGA AAGCTGATTT TTTTTAATTA CCATGCTTCA CAATGTTAAG   4800
TTATATGGGG AGCAACAGCA AACAGGTGCT AATTTGTTTT GGATATAGTA TAAGCAGTGT   4860
CTGTGTTTTG AAAGAATAGA ACACAGTTTG TAGTGCCACT GTTGTTTTGG GGGGGCTTT    4920
TTTTCTTTTT CCGGAAAATC CTTAAACCTT AAGATACTAA GGACGTTGTT TTGGTTGTAC   4980
TTGGAATTCT TAGTCACAAA ATATATTTTG TTTACAAAAA TTTCTGTAAA ACAGGTTATA   5040
ACAGTGTTTA AAGTCTCAGT TTCTTGCTTG GGAACTTGT GTCCCTAATG TGTTAGATTG    5100
CTAGATTGCT AAGGAGCTGA TACTTGACAG TTTTTTAGAC CTGTGTTACT AAAAAAAGA    5160
TGAATGTCGG AAAAGGGTGT TGGGAGGGTG GTCAACAAAG AAACAAAGAT GTTATGGTGT   5220
TTAGACTTAT GGTTGTTAAA AATGTCATCT CAAGTCAAGT CACTGGTCTG TTTGCATTTG   5280
ATACATTTTT GTACTAACTA GCATTGTAAA ATTATTTCAT GATTAGAAAT TACCTGTGGA   5340
TATTTGTATA AAAGTGTGAA ATAAATTTTT TATAAAGTG TTCATTGTTT CGTAACACAG    5400
CATTGTATAT GTGAAGCAAA CTCTAAAATT ATAAATGACA ACCTGAATTA TCTATTTCAT   5460
```

CAAAAAAAAA AAAAAAAAA ACTTTATGGG CACAACTGG                    5499

(2) INFORMATION FOR SEQ ID NO:5:

(i) SEQUENCE CHARACTERISTICS:
        (A) LENGTH: 141 amino acids
        (B) TYPE: amino acid
        (D) TOPOLOGY: unknown (ii) MOLECULE TYPE: protein (iii) HYPOTHETICAL: YES (iv) ANTI-SENSE: NO (v) FRAGMENT TYPE: internal (ix) FEATURE:
        (A) NAME/KEY: Region
        (B) LOCATION: 1..141
        (D) OTHER INFORMATION: /note="The 141 amino acid sequence
            predicted from the nucleic acid product which
            results from amplification of the mouse ALPHA 6B
            cDNA with primers 1157/1156."

(ix) FEATURE:
        (A) NAME/KEY: Domain
        (B) LOCATION: 88..113
        (D) OTHER INFORMATION: /note="The putative transmembrane
            domain."

(ix) FEATURE:
        (A) NAME/KEY: Region
        (B) LOCATION: 1..120
        (D) OTHER INFORMATION: /note="SEQ ID NO:5 is identical to
            SEQ ID NO:7 at amino acid position 1 through 120;
            the two sequences diverge at amino acid 121."

(xi) SEQUENCE DESCRIPTION: SEQ ID NO:5:

```
Thr Leu Asn Cys Ser Val Asn Val Arg Cys Val Asn Ile Arg Cys Pro
 1               5                  10                  15

Leu Arg Gly Leu Asp Ser Lys Ala Ser Leu Val Leu Arg Ser Arg Leu
            20                  25                  30

Trp Asn Ser Thr Phe Leu Glu Glu Tyr Ser Lys Leu Asn Tyr Leu Asp
        35                  40                  45

Ile Leu Leu Arg Ala Ser Ile Asp Val Thr Ala Ala Ala Gln Asn Ile
    50                  55                  60

Lys Leu Leu Thr Ala Gly Thr Gln Val Arg Val Thr Val Phe Pro Ser
65                      70                  75                  80

Lys Thr Val Ala Gln Tyr Ser Gly Val Ala Trp Trp Ile Ile Leu Leu
                85                  90                  95

Ala Val Leu Ala Gly Ile Leu Met Leu Ala Leu Leu Val Phe Leu Leu
                100                 105                 110

Trp Lys Cys Gly Phe Phe Lys Arg Ser Arg Tyr Asp Asp Ser Ile Pro
        115                 120                 125

Arg Tyr His Ala Val Arg Ile Arg Lys Glu Glu Arg Glu
        130                 135                 140
```

(2) INFORMATION FOR SEQ ID NO:6:

(i) SEQUENCE CHARACTERISTICS:
        (A) LENGTH: 426 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO ( i x ) FEATURE:
    ( A ) NAME/KEY: miscfeature
    ( B ) LOCATION: 1..426
    ( D ) OTHER INFORMATION: /product="Mouse ALPHA 6B amino
        acid sequence in SEQ ID NO:5."

( i x ) FEATURE:
    ( A ) NAME/KEY: miscfeature
    ( B ) LOCATION: 262..337
    ( D ) OTHER INFORMATION: /function="Putative transmembrane
        region."

( i x ) FEATURE:
    ( A ) NAME/KEY: miscfeature
    ( B ) LOCATION: (342 343)
    ( D ) OTHER INFORMATION: /note="SEQ ID NO:6 is identical to
        SEQ ID NO:8 except for 130 nucleotides present in
        SEQ ID NO:8 but deleted between nucleotides 342
        and 343 of SEQ ID NO:6."

( x i ) SEQUENCE DESCRIPTION: SEQ ID NO:6:

| | | | | | | |
|---|---|---|---|---|---|---|
| GACTCTTAAC | TGTAGCGTGA | ACGTGAGGTG | TGTGAACATC | AGGTGCCCAC | TGCGAGGGCT | 60 |
| GGACAGCAAG | GCCTCTCTCG | TTCTTCGTTC | CAGGTTGTGG | AACAGCACAT | TTCTAGAGGA | 120 |
| ATATTCCAAA | CTGAACTACT | TGGACATTCT | CCTGAGGGCT | TCCATAGATG | TCACCGCTGC | 180 |
| TGCTCAGAAT | ATCAAGCTCC | TCACCGCCGG | CACTCAGGTT | CGAGTGACGG | TGTTTCCCTC | 240 |
| AAAGACTGTA | GCTCAGTATT | CAGGAGTAGC | TTGGTGGATC | ATCCTCCTGG | CTGTTCTTGC | 300 |
| CGGGATTCTG | ATGCTGGCTC | TATTAGTGTT | TTTACTGTGG | AAGTGTGGAT | TCTTTAAGCG | 360 |
| CTCTAGGTAC | GATGACAGCA | TTCCCCGATA | CCATGCGGTG | CGGATCCGGA | AAGAAGAGCG | 420 |
| AGAGAT | | | | | | 426 |

( 2 ) INFORMATION FOR SEQ ID NO:7:

( i ) SEQUENCE CHARACTERISTICS:
        ( A ) LENGTH: 149 amino acids
        ( B ) TYPE: amino acid
        ( D ) TOPOLOGY: unknown ( i i ) MOLECULE TYPE: protein ( i i i ) HYPOTHETICAL: YES ( i v ) ANTI-SENSE: NO ( v ) FRAGMENT TYPE: internal ( i x ) FEATURE:
        ( A ) NAME/KEY: Region
        ( B ) LOCATION: 1..149
        ( D ) OTHER INFORMATION: /note="The 149 amino acid sequence
            predicted from the product which results from
            amplification of the mouse ALPHA 6A cDNA with
            primers 1157/1156."

( i x ) FEATURE:
        ( A ) NAME/KEY: Region
        ( B ) LOCATION: 1..120
        ( D ) OTHER INFORMATION: /note="SEQ ID NO:7 is identical to
            SEQ ID NO:5 at amino acid positions 1 through 120;
            the sequences diverge at amino acid 121."

( x i ) SEQUENCE DESCRIPTION: SEQ ID NO:7:

Thr Leu Asn Cys Ser Val Asn Val Arg Cys Val Asn Ile Arg Cys Pro
1               5                   10                  15

Leu Arg Gly Leu Asp Ser Lys Ala Ser Leu Val Leu Arg Ser Arg Leu
            20                  25                  30

Trp Asn Ser Thr Phe Leu Glu Glu Tyr Ser Lys Leu Asn Tyr Leu Asp
        35                  40                  45

Ile Leu Leu Arg Ala Ser Ile Asp Val Thr Ala Ala Ala Gln Asn Ile

|  | 50 |  |  |  |  | 55 |  |  |  |  | 60 |  |  |  |
|---|---|---|---|---|---|---|---|---|---|---|---|---|---|---|
| Lys<br>65 | Leu | Leu | Thr | Ala | Gly<br>70 | Thr | Gln | Val | Arg | Val<br>75 | Thr | Val | Phe | Pro | Ser<br>80 |
| Lys | Thr | Val | Ala | Gln<br>85 | Tyr | Ser | Gly | Val | Ala<br>90 | Trp | Trp | Ile | Ile | Leu<br>95 | Leu |
| Ala | Val | Leu | Ala<br>100 | Gly | Ile | Leu | Met<br>105 | Ala | Leu | Leu | Val<br>110 | Phe | Leu | Leu |
| Trp | Lys | Cys<br>115 | Gly | Phe | Phe | Lys<br>120 | Arg | Asn | Lys | Lys | Asp<br>125 | His | Tyr | Asp | Ala |
| Thr | Tyr<br>130 | His | Lys | Ala | Glu | Ile<br>135 | His | Thr | Gln | Pro | Ser<br>140 | Asp | Lys | Glu | Arg |
| Leu<br>145 | Thr | Ser | Asp | Ala |

(2) INFORMATION FOR SEQ ID NO:8:

(i) SEQUENCE CHARACTERISTICS:
(A) LENGTH: 556 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: miscfeature
(B) LOCATION: 1..556
(D) OTHER INFORMATION: /product="Mouse ALPHA 6A amino
acid sequence in SEQ ID NO:7."
/ note="SEQ ID NO:8 is the 556 base nucleotide
sequence corresponding to the mouse ALPHA 6A amino
acid sequence SEQ ID NO:7, plus the first 109
nucleotides in the 3'noncoding region."

(ix) FEATURE:
(A) NAME/KEY: miscfeature
(B) LOCATION: 342..472
(D) OTHER INFORMATION: /note="SEQ ID NO:8 is identical to
SEQ ID NO:6 except it has a 130 base insertion
(nucleotides 342-472 of SEQ ID NO:8) between
nucleotides 352 and 353 of SEQ ID NO:6."

(xi) SEQUENCE DESCRIPTION: SEQ ID NO:8:

```
GACTCTTAAC TGTAGCGTGA ACGTGAGGTG TGTGAACATC AGGTGCCCAC TGCGAGGGCT      60
GGACAGCAAG GCCTCTCTCG TTCTTCGTTC CAGGTTGTGG AACAGCACAT TTCTAGAGGA     120
ATATTCCAAA CTGAACTACT TGGACATTCT CCTGAGGGCT TCCATAGATG TCACCGCTGC     180
TGCTCAGAAT ATCAAGCTCC TCACCGCCGG CACTCAGGTT CGAGTGACGG TGTTTCCCTC     240
AAAGACTGTA GCTCAGTATT CAGGAGTAGC TTGGTGGATC ATCCTCCTGG CTGTTCTTGC     300
CGGGATTCTG ATGCTGGCTC TATTAGTGTT TTTACTGTGG AAGTGTGGCT TCTTCAAGAG     360
AAATAAGAAA GATCATTACG ATGCCACCTA TCACAAGGCT GAGATCCATA CTCAGCCGTC     420
TGATAAAGAG AGGCTTACTT CCGATGCATA GTATTGATCT ACTTCCATAA TTGTGTGGAT     480
TCTTTAAGCG CTCTAGGTAC GATGACAGCA TTCCCCGATA CCATGCGGTG CGGATCCGGA     540
AAGAAGAGCG AGAGAT                                                     556
```

(2) INFORMATION FOR SEQ ID NO:9:

(i) SEQUENCE CHARACTERISTICS:
(A) LENGTH: 153 amino acids
(B) TYPE: amino acid
(D) TOPOLOGY: unknown (i i) MOLECULE TYPE: protein (i i i) HYPOTHETICAL: YES (i v) ANTI-SENSE: NO (v) FRAGMENT TYPE: internal (i x) FEATURE:
    (A) NAME/KEY: Region
    (B) LOCATION: 1..153
    (D) OTHER INFORMATION: /note="SEQ ID NO:9 is the 153
        amino acid sequence predicted from the product
        which results from amplification of the mouse
        ALPHA 3B cDNA with primers 2032/2033."

(i x) FEATURE:
    (A) NAME/KEY: Domain
    (B) LOCATION: 108..112
    (D) OTHER INFORMATION: /note="The cytoplasmic sequence
        CDFFK begins at amino acid position 108."

(x i) SEQUENCE DESCRIPTION: SEQ ID NO:9:

```
Ala Arg Cys Val Trp Leu Glu Cys Pro Leu Pro Asp Thr Ser Asn Ile
 1           5                  10                  15

Thr Asn Val Thr Val Lys Ala Arg Val Trp Asn Ser Thr Phe Ile Glu
            20                  25                  30

Asp Tyr Lys Asp Phe Asp Arg Val Arg Val Asp Gly Trp Ala Thr Leu
        35                  40                  45

Phe Leu Arg Thr Ser Ile Pro Thr Ile Asn Met Glu Asn Lys Thr Thr
    50                  55                  60

Cys Phe Ser Val Asn Ile Asp Ser Lys Leu Leu Glu Glu Leu Pro Ala
65                  70                  75                  80

Glu Ile Glu Leu Trp Leu Val Leu Val Ala Val Gly Ala Gly Leu Leu
                85                  90                  95

Leu Leu Gly Leu Ile Ile Ile Leu Leu Trp Lys Cys Asp Phe Phe Lys
            100                 105                 110

Pro Thr Arg Tyr Tyr Arg Ile Met Pro Lys Tyr His Ala Val Arg Ile
        115                 120                 125

Arg Glu Glu Asp Arg Tyr Pro Pro Pro Gly Ser Thr Leu Pro Thr Lys
    130                 135                 140

Lys His Trp Val Thr Ser Trp Gln Ile
145                 150
```

(2) INFORMATION FOR SEQ ID NO:10:

(i) SEQUENCE CHARACTERISTICS:
        (A) LENGTH: 463 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (i x) FEATURE:
    (A) NAME/KEY: miscfeature
    (B) LOCATION: 1..463
    (D) OTHER INFORMATION: /product="Mouse ALPHA 3B amino
        acid sequence in SEQ ID NO:9."
        / note="SEQ ID NO:10 is the 463 base nucleotide
        sequence corresponding to the mouse ALPHA 3B amino
        acid sequence in SEQ ID NO:9."

(i x) FEATURE:
    (A) NAME/KEY: miscfeature
    (B) LOCATION: 324..338

(D) OTHER INFORMATION: /product="The cytoplasmic sequence CDFFK."

(xi) SEQUENCE DESCRIPTION: SEQ ID NO:10:

| | | | | | | |
|---|---|---|---|---|---|---|
| GTGCCCGCTG | TGTGTGGCTG | GAGTGCCCCC | TTCCAGACAC | CTCCAACATT | ACCAATGTGA | 60 |
| CCGTGAAAGC | ACGGGTGTGG | AACAGCACCT | TCATTGAGGA | CTACAAAGAC | TTTGACAGAG | 120 |
| TCAGGGTAGA | TGGCTGGGCT | ACCCTGTTCC | TGAGAACCAG | CATCCCTACC | ATCAACATGG | 180 |
| AGAACAAGAC | CACATGTTTC | TCTGTGAACA | TTGACTCAAA | GCTGTTGGAG | GAGCTGCCCG | 240 |
| CTGAGATTGA | GCTGTGGTTG | GTGCTTGTGG | CCGTGGGTGC | TGGGTTGCTG | CTGCTGGGGC | 300 |
| TCATCATCAT | CCTCTTGTGG | AAGTGTGACT | TCTTTAAGCC | GACCCGCTAC | TACCGGATTA | 360 |
| TGCCCAAGTA | CCATGCAGTG | CGTATCCGGG | AGGAGGACCG | CTACCCACCT | CCAGGGAGCA | 420 |
| CGCTACCCAC | CAAGAAGCAC | TGGGTCACCA | GCTGGCAGAT | TCG | | 463 |

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: miscfeature
        (B) LOCATION: 1..20
        (D) OTHER INFORMATION: /standardname="PCR PRIMER 1157"
        / note="Primer corresponds to bp 2918-2937 of the
        ALPHA 6A cDNA sequence of SEQ ID NO:2."

(xi) SEQUENCE DESCRIPTION: SEQ ID NO:11:

GACTCTTAAC TGTAGCGTGA                                                                                   20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: miscfeature
        (B) LOCATION: 1..20
        (D) OTHER INFORMATION: /standardname="PCR PRIMER 1156"
        / note="The primer corresponds to the complement
        of bp 3454-3473 of the APHA 6A cDNA sequence of
        SEQ ID NO:2."

(xi) SEQUENCE DESCRIPTION: SEQ ID NO:12:

ATCTCTCGCT CTTCTTTCCG                                                                               20

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (i x) FEATURE:
    (A) NAME/KEY: miscfeature
    (B) LOCATION: 1..19
    (D) OTHER INFORMATION: /standardname="PCR PRIMER 1681"
    / note="The primer corresponds to bp 2942-2960 of
    the ALPHA 6A cDNA sequence of SEQ ID NO:2."

(x i) SEQUENCE DESCRIPTION: SEQ ID NO:13:

GAACTGTGTG AACATCAGA 19

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (i x) FEATURE:
        (A) NAME/KEY: miscfeature
        (B) LOCATION: 1..20
        (D) OTHER INFORMATION: /standardname="PCR PRIMER 2002"
        / note="The primer corresponds to the complement
        of bp 3433- 3452 of the ALPHA 6A cDNA sequence of
        SEQ ID NO:2."

(x i) SEQUENCE DESCRIPTION: SEQ ID NO:14:

ATCCTTACAG CATGGTATCG 20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (i x) FEATURE:
        (A) NAME/KEY: miscfeature
        (B) LOCATION: 1..20
        (D) OTHER INFORMATION: /standardname="PCR PRIMER 2032"
        / note="The primer corresponds to the hamster
        ALPHA 3A cDNA sequence of Tsuji et. al., J. Biol.
        Chem., 265:7016-7021 (1990)."

(x i) SEQUENCE DESCRIPTION: SEQ ID NO:15:

AAGCCAAATC TGAGACTGTG 20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

( i i i ) HYPOTHETICAL: NO ( i v ) ANTI-SENSE: NO ( i x ) FEATURE:
    ( A ) NAME/KEY: miscfeature
    ( B ) LOCATION: 1..20
    ( D ) OTHER INFORMATION: /standardname="PCR PRIMER 2033"
    / note="The primer corresponds to the hamster
    ALPHA 3A cDNA sequence of Tsuji et al., J. Biol.
    Chem., 265:7016-7021 (1990)."

( x i ) SEQUENCE DESCRIPTION: SEQ ID NO:16:

GTAGTATCGG TCCCGAATCT           20